United States Patent
Farley et al.

(10) Patent No.: US 11,944,766 B2
(45) Date of Patent: Apr. 2, 2024

(54) INTRAVASCULAR CATHETER INSERTION DEVICE

(71) Applicant: Truecath Inc., Camarillo, CA (US)

(72) Inventors: Sean S. Farley, Hidden Hills, CA (US); Hunter Cordeiro, Monrovia, CA (US)

(73) Assignee: Truecath Inc, Camarillo, CA (US)

( * ) Notice: Subject to any disclaimer, the term of this patent is extended or adjusted under 35 U.S.C. 154(b) by 775 days.

(21) Appl. No.: 17/247,395

(22) Filed: Dec. 9, 2020

(65) Prior Publication Data

US 2021/0113817 A1 Apr. 22, 2021

Related U.S. Application Data

(63) Continuation-in-part of application No. 16/192,756, filed on Nov. 15, 2018, now Pat. No. 10,881,833, which is a continuation-in-part of application No. 15/230,333, filed on Aug. 5, 2016, now Pat. No. 10,136,917, which is a continuation-in-part of application No. 14/326,088, filed on Jul. 8, 2014, now Pat. No. 9,433,758.

(60) Provisional application No. 61/844,349, filed on Jul. 9, 2013.

(51) Int. Cl.
  *A61M 25/06* (2006.01)
  *A61M 25/00* (2006.01)

(52) U.S. Cl.
  CPC .... *A61M 25/0693* (2013.01); *A61M 25/0023* (2013.01)

(58) Field of Classification Search
  CPC .............. A61M 25/0023; A61M 25/06; A61M 25/0612; A61M 25/0618; A61M 25/0625; A61M 25/065; A61M 25/0097; A61M 2025/0175; A61M 25/0693; A61M 25/0631; A61M 25/0606; A61M 2025/0004
  See application file for complete search history.

(56) References Cited

U.S. PATENT DOCUMENTS

| | | | |
|---|---|---|---|
| 4,487,605 A | 12/1984 | McGaughey |
| 4,906,236 A | 3/1990 | Alberts |
| 1,944,728 A | 7/1990 | Carrell |
| 4,966,589 A | 10/1990 | Kaufman |
| 5,186,712 A | 2/1993 | Kelso |
| 5,195,985 A | 3/1993 | Hall |

(Continued)

*Primary Examiner* — Robert J Utama
*Assistant Examiner* — Leah J Swanson
(74) *Attorney, Agent, or Firm* — Orbit IP

(57) ABSTRACT

A catheter insertion device includes a hollow needle attached to a needle base. A compression spring mechanically biases the needle base away from a plunger. A catheter is configured to be contactable by the plunger when the plunger moves in a forward direction. An expandable chamber is in fluidic and/or pneumatic communication with the hollow needle. The plunger inserts the catheter when a vacuum formed in the expandable chamber by the compression spring pushing the plunger away from the needle base is released by a fluid and/or a gas entering the hollow needle at a distal skin-piercing end as it punctures a vein or artery. A generally hollow housing includes an annularly-shaped seal relief formed as an inside surface where in a stored position a second circumferential seal captured by the plunger is not in contact with the inside surface of the generally hollow housing.

12 Claims, 41 Drawing Sheets

(56) References Cited

U.S. PATENT DOCUMENTS

| | | | |
|---|---|---|---|
| 5,300,046 | A | 4/1994 | Scarfone |
| 5,312,361 | A * | 5/1994 | Zadini .................. A61M 5/158 |
| | | | 604/233 |
| 5,313,361 | A | 5/1994 | Martin |
| 5,334,159 | A | 8/1994 | Turkel |
| 5,336,176 | A | 8/1994 | Yoon |
| 5,407,431 | A | 4/1995 | Botich |
| 5,411,486 | A | 5/1995 | Zadini |
| 5,415,177 | A * | 5/1995 | Zadini ................ A61M 25/0116 |
| | | | 600/585 |
| 5,423,760 | A | 6/1995 | Yoon |
| 5,423,770 | A | 6/1995 | Yoon |
| 5,480,388 | A | 1/1996 | Zadini et al. |
| 5,527,290 | A | 6/1996 | Zadini |
| 5,527,291 | A | 6/1996 | Zadini |
| 5,591,138 | A | 1/1997 | Vaillancourt |
| 5,676,658 | A | 10/1997 | Erksine |
| 5,690,619 | A | 11/1997 | Erksine |
| 5,700,250 | A | 12/1997 | Erksine |
| 5,749,371 | A | 5/1998 | Zadini |
| 5,749,856 | A | 5/1998 | Zadini |
| 5,755,709 | A | 5/1998 | Cuppy |
| 5,795,339 | A | 8/1998 | Erksine |
| 5,865,806 | A | 2/1999 | Howell |
| 5,879,338 | A | 3/1999 | Mahurkar |
| 5,897,337 | A | 3/1999 | Kuracina |
| 5,911,705 | A | 6/1999 | Howell |
| 6,001,080 | A | 12/1999 | Kuracina |
| 6,086,563 | A | 7/2000 | Moulton |
| 6,090,078 | A | 7/2000 | Erskine |
| 6,165,136 | A | 12/2000 | Nishtala |
| 6,197,001 | B1 | 3/2001 | Wilson |
| 6,210,375 | B1 | 4/2001 | Moulton |
| 6,217,558 | B1 | 4/2001 | Zadini |
| 6,273,861 | B1 | 8/2001 | Bates |
| 6,277,100 | B1 | 8/2001 | Raulerson |
| 6,280,401 | B1 | 8/2001 | Mahurkar |
| 6,287,322 | B1 | 9/2001 | Zhu |
| 6,379,337 | B1 | 4/2002 | Mohammad |
| 6,398,743 | B1 | 6/2002 | Halseth |
| 6,443,929 | B1 | 9/2002 | Kuracina |
| 6,582,402 | B1 | 6/2003 | Erksine |
| 6,626,859 | B2 | 9/2003 | von Segesser |
| 6,629,959 | B2 | 10/2003 | Kuracina |
| 6,786,875 | B2 | 9/2004 | Barker |
| 6,796,963 | B2 | 9/2004 | Carpenter |
| 6,835,193 | B2 | 12/2004 | Epstein |
| 6,860,871 | B2 | 3/2005 | Kuracina |
| 6,878,129 | B2 | 4/2005 | Donaldson |
| 6,979,317 | B2 | 12/2005 | Galt |
| 7,153,276 | B2 | 12/2006 | Barker |
| 7,294,118 | B2 | 11/2007 | Saulenas |
| 7,344,516 | B2 | 3/2008 | Erksine |
| 7,422,572 | B2 | 9/2008 | Popov |
| 7,481,797 | B2 | 1/2009 | Mahurkar |
| 7,534,231 | B2 | 5/2009 | Kuracina |
| 7,691,083 | B2 | 4/2010 | Botich |
| 7,731,692 | B2 | 6/2010 | Moos |
| 7,846,132 | B2 | 12/2010 | Gravesen |
| 7,850,650 | B2 | 12/2010 | Breitweiser |
| 7,927,314 | B2 | 4/2011 | Kuracina |
| 7,967,776 | B2 | 6/2011 | Von Segesser |
| 8,062,261 | B2 | 11/2011 | Adams |
| 8,133,237 | B2 | 3/2012 | Oostman, Jr. |
| 8,157,835 | B2 | 4/2012 | Taylor |
| RE43,473 | E | 6/2012 | Newby |
| 8,292,849 | B2 | 10/2012 | Bobroff |
| 8,308,685 | B2 | 11/2012 | Botich |
| 8,313,493 | B2 | 11/2012 | Fischer |
| 8,414,539 | B1 | 4/2013 | Kuracina |
| 8,444,605 | B2 | 5/2013 | Kuracina |
| 2003/0028172 | A1 | 2/2003 | Epstein |
| 2003/0120223 | A1 | 6/2003 | Von Segesser |
| 2004/0116855 | A1 | 6/2004 | Popov |
| 2006/0184105 | A1 | 8/2006 | Townsend |
| 2010/0004558 | A1 | 1/2010 | Frankhouser |
| 2010/0010499 | A1 | 1/2010 | Fischer |
| 2011/0166526 | A1 | 7/2011 | Kuracina |
| 2012/0016307 | A1 | 1/2012 | Burkholz |
| 2012/0209303 | A1 | 8/2012 | Frankhouser |
| 2012/0238966 | A1 | 9/2012 | Kuracina |
| 2013/0066200 | A1 | 3/2013 | Frankhouser |

* cited by examiner

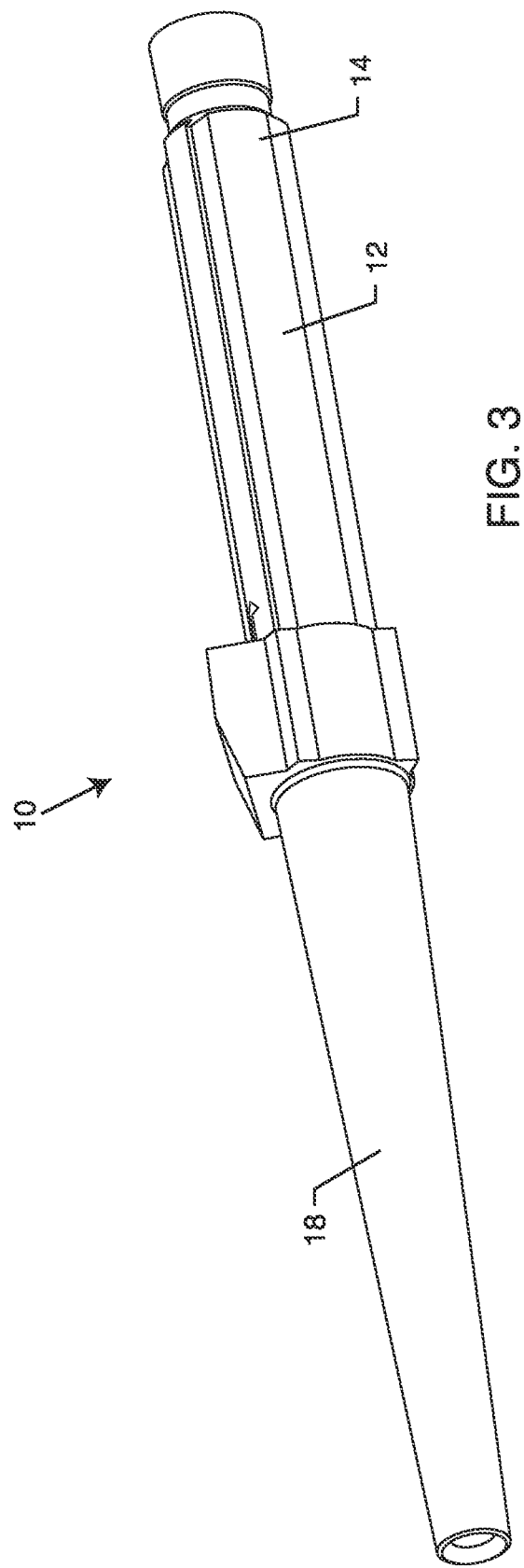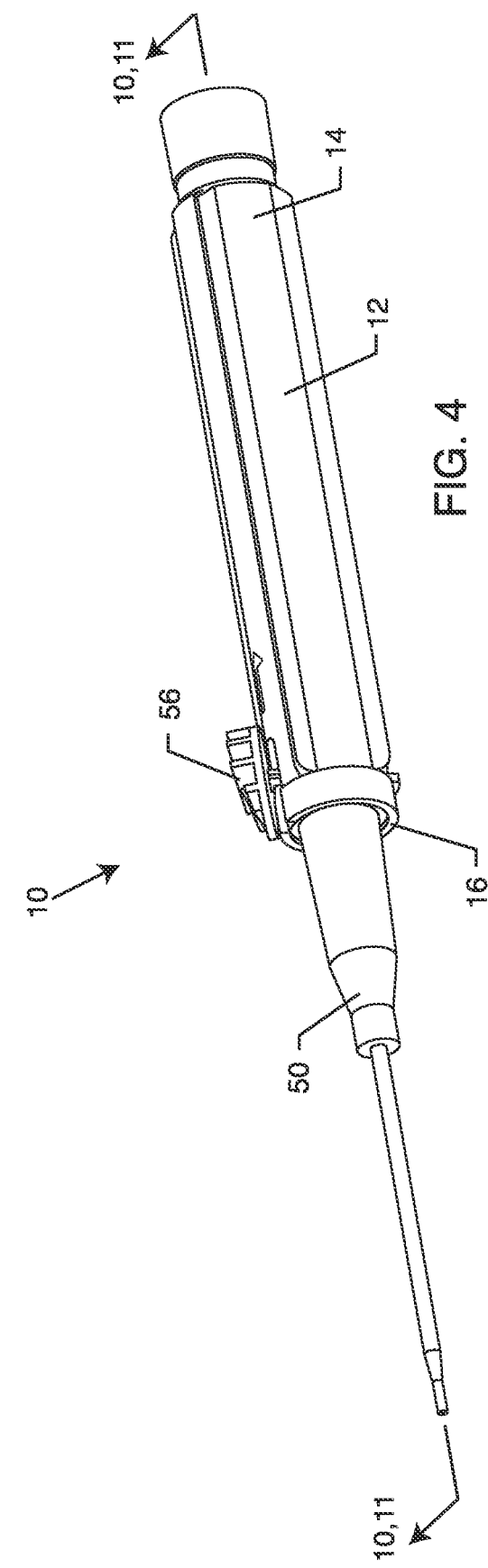

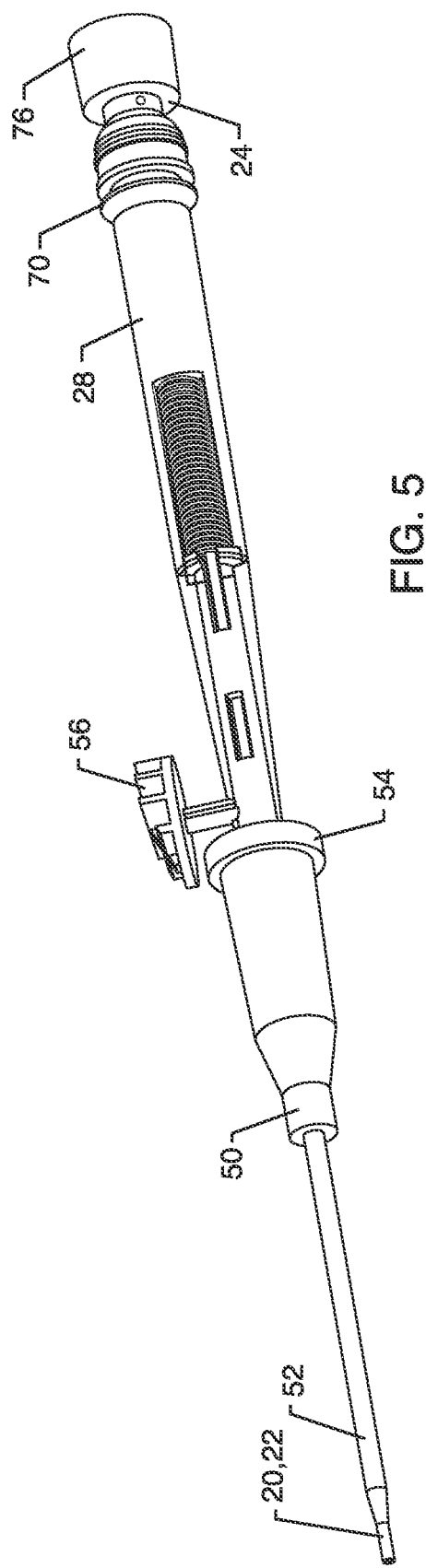
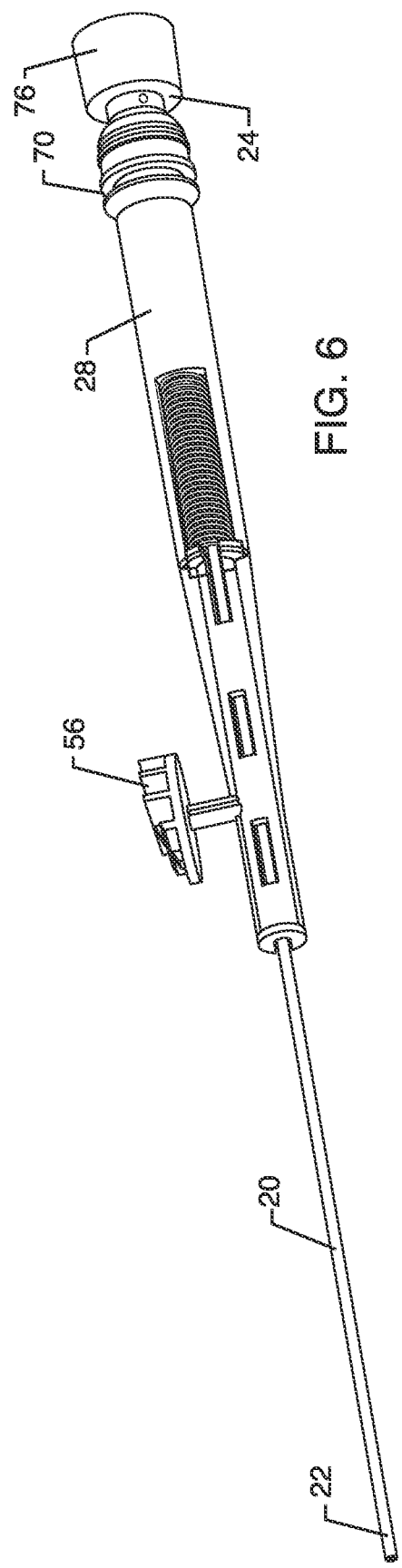

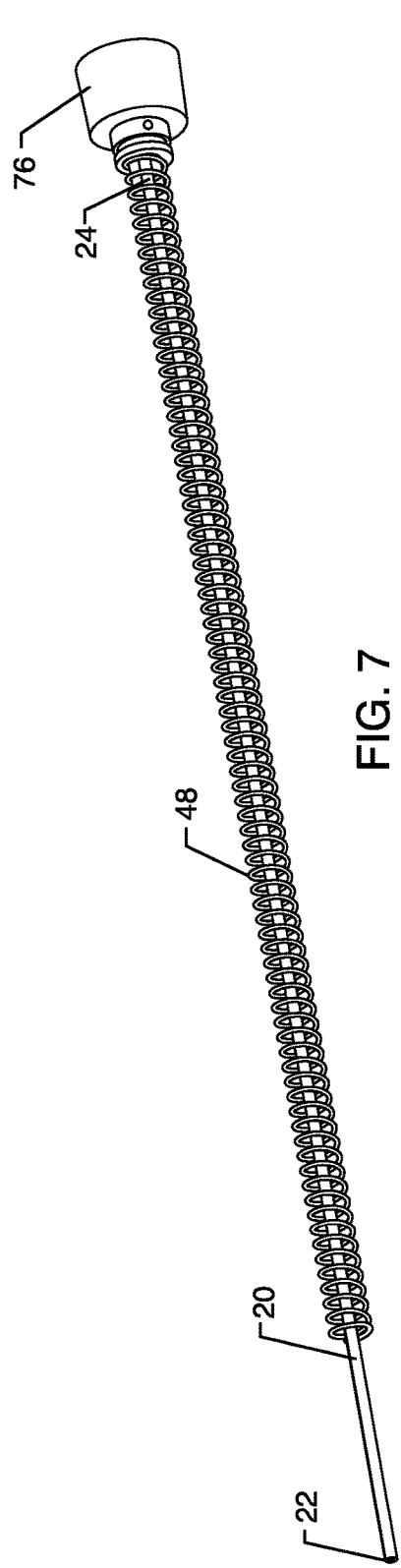
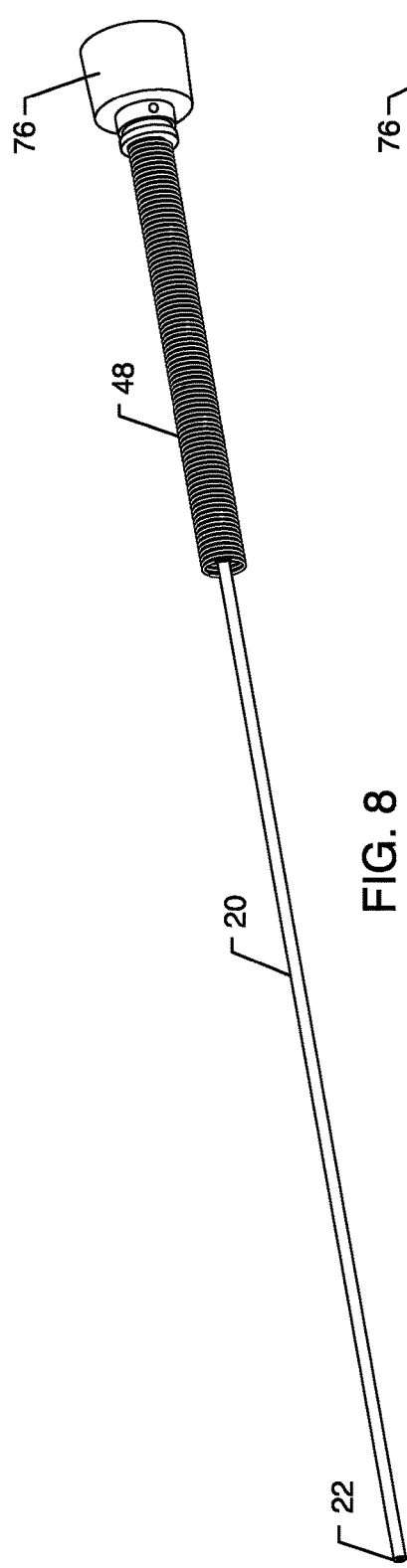
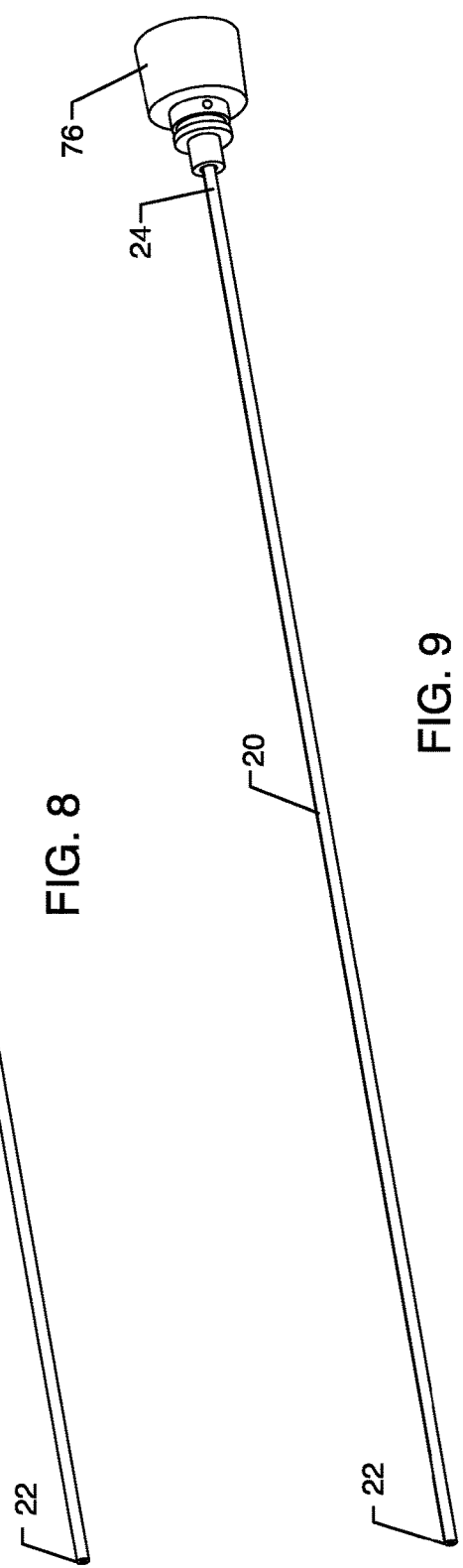
FIG. 7
FIG. 8
FIG. 9

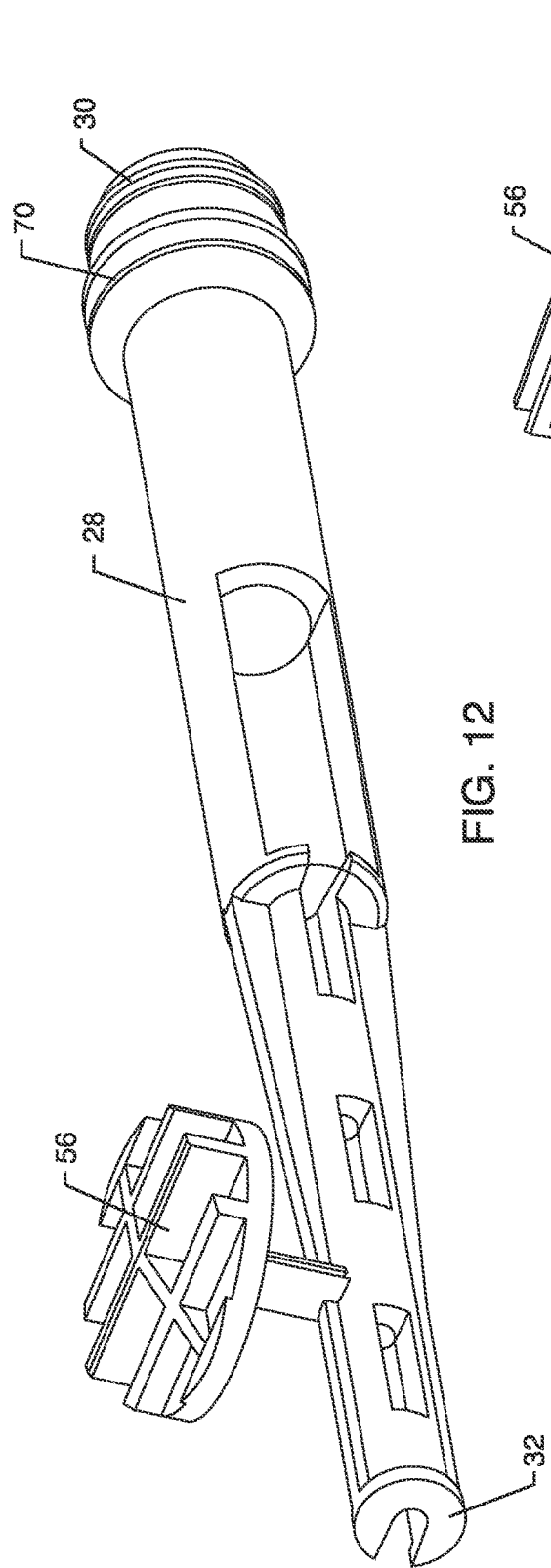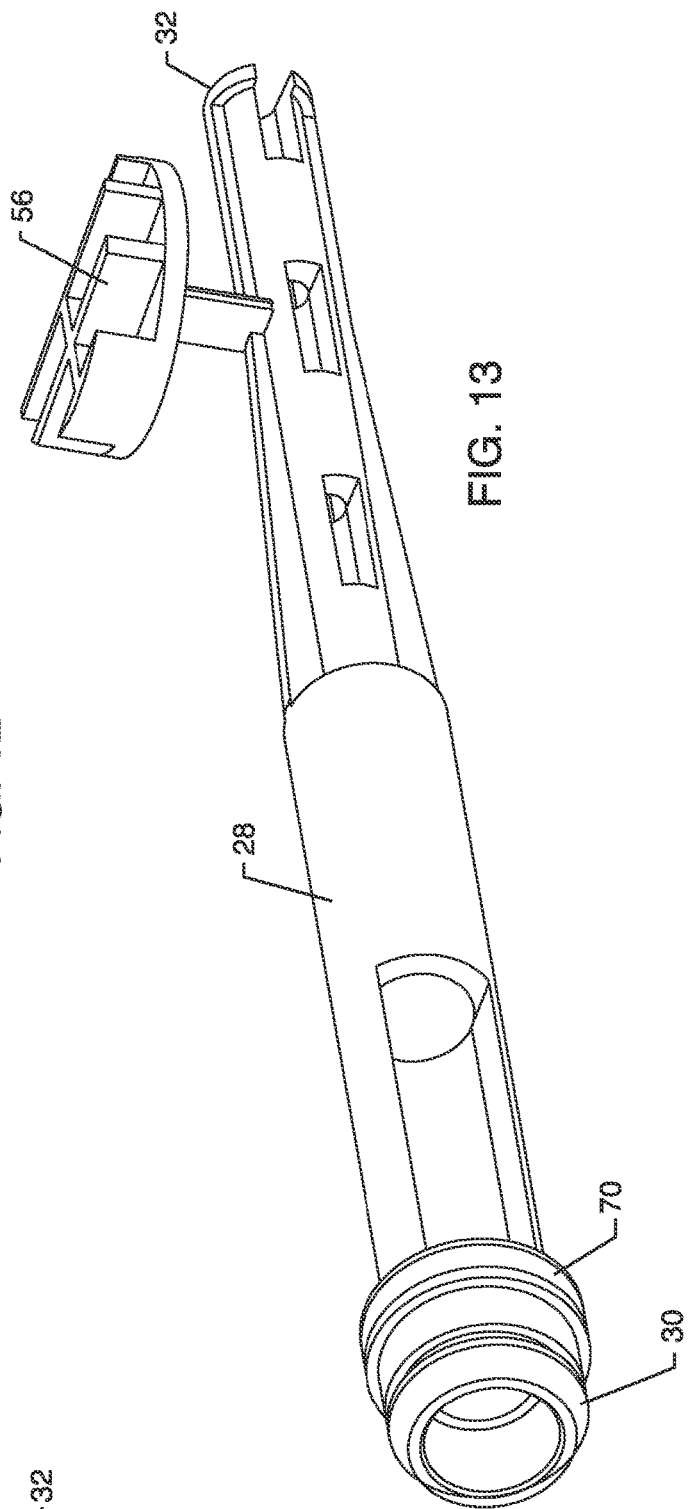

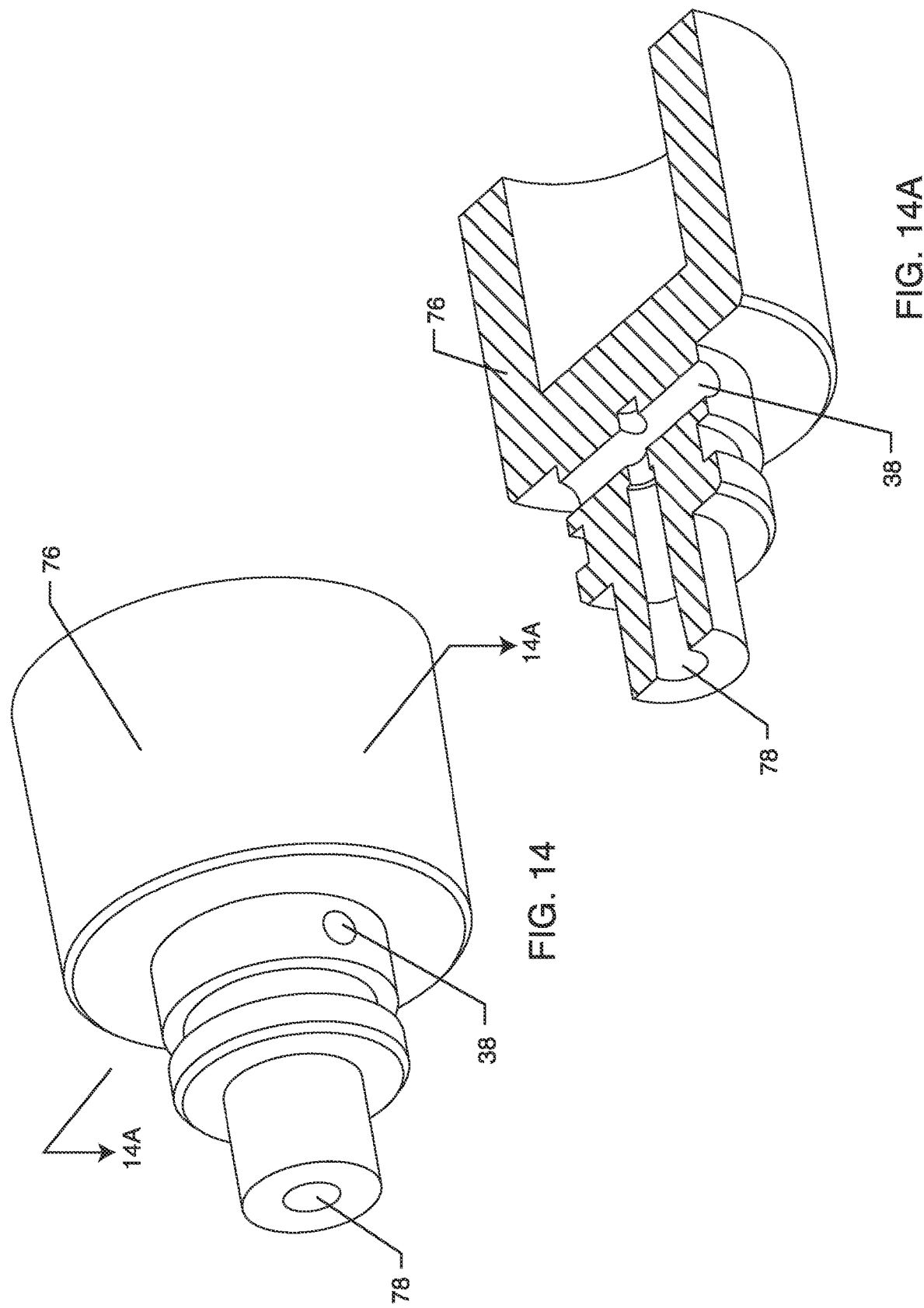

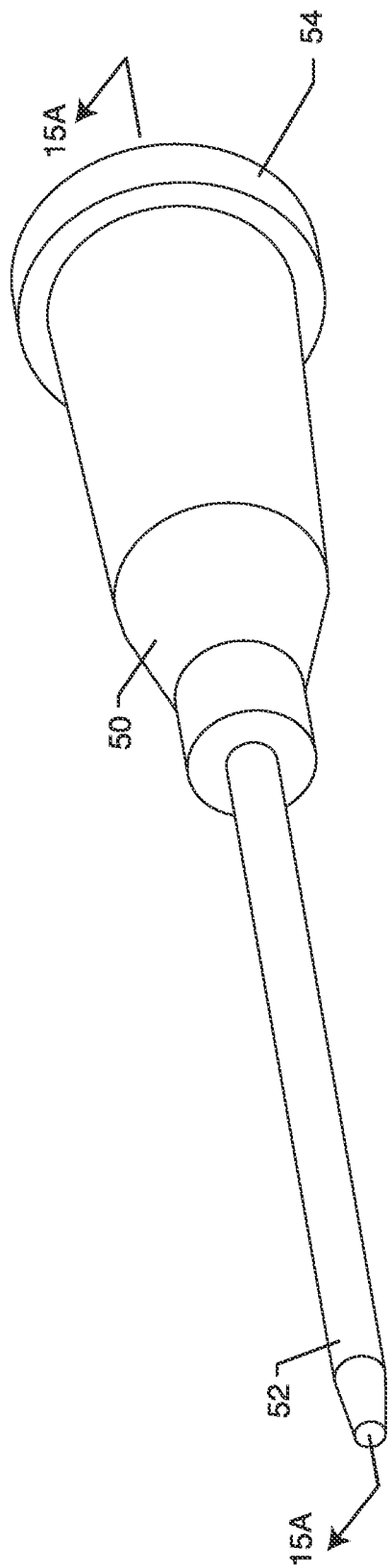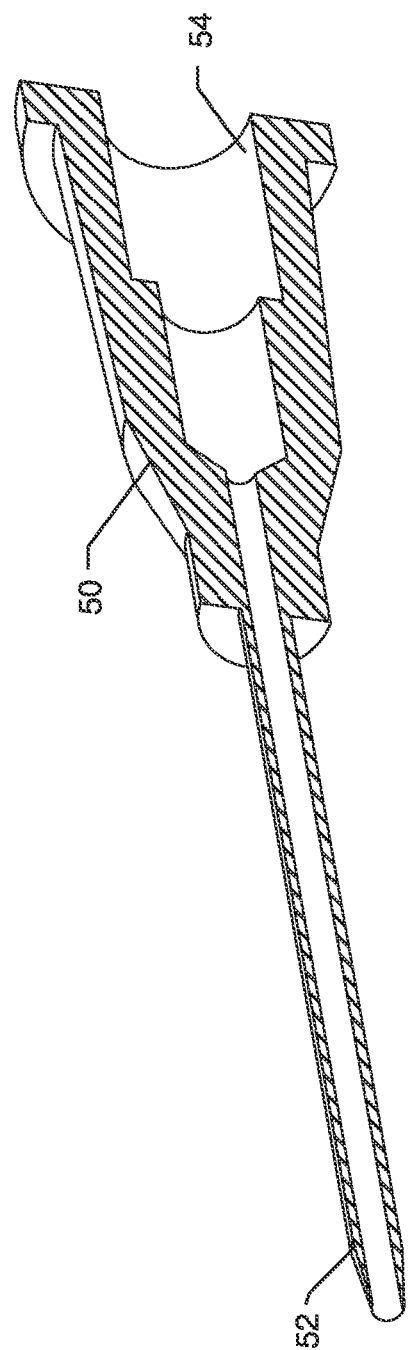

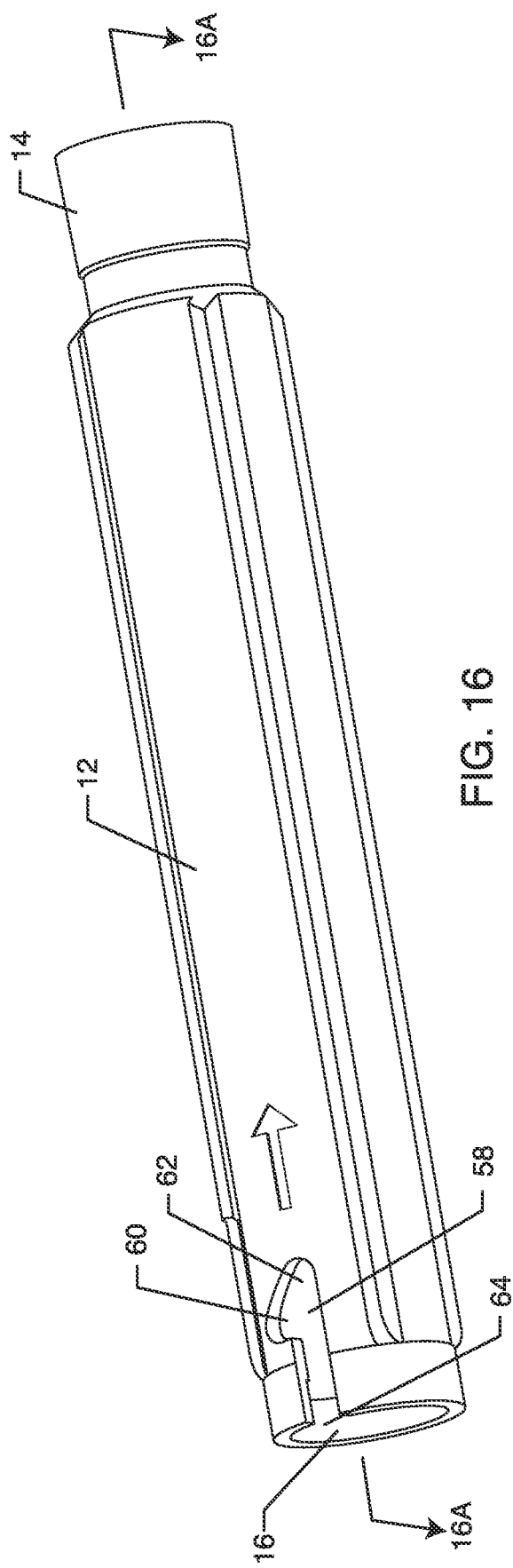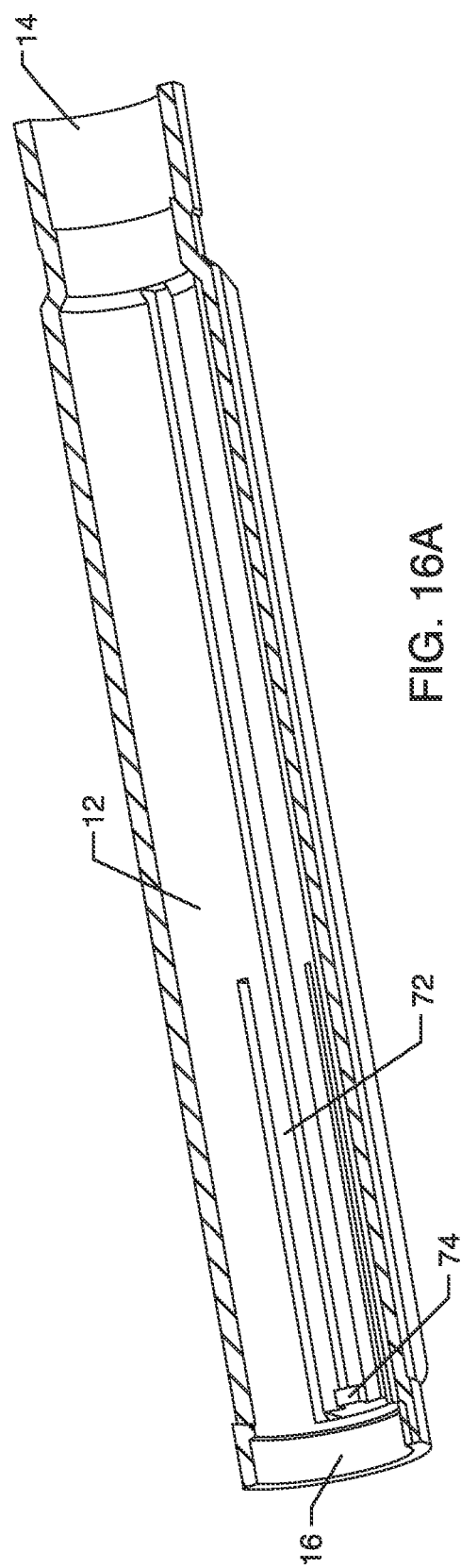

(STORED POSITION)

(ARMED POSITION)

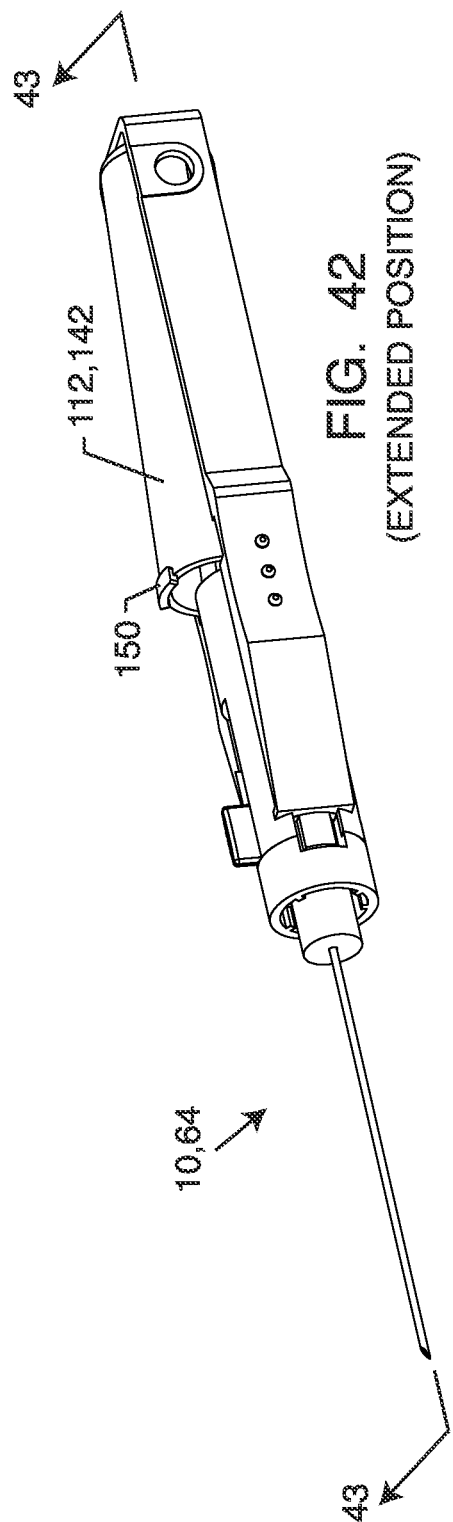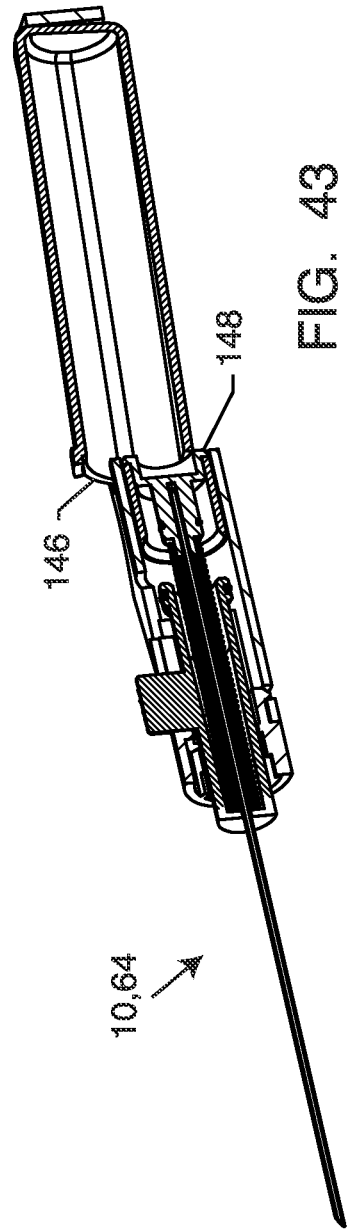

(RETRACTED POSITION)

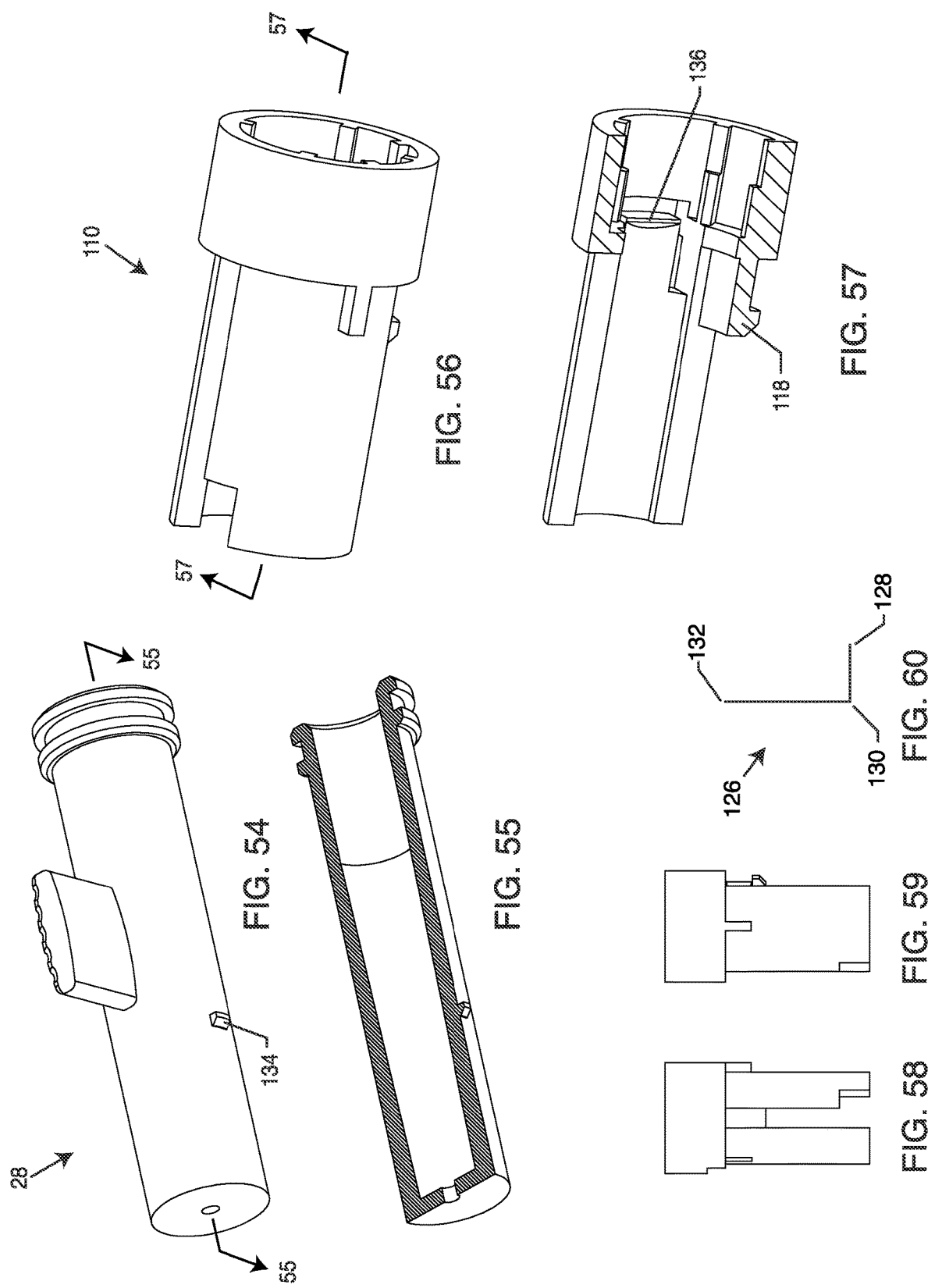

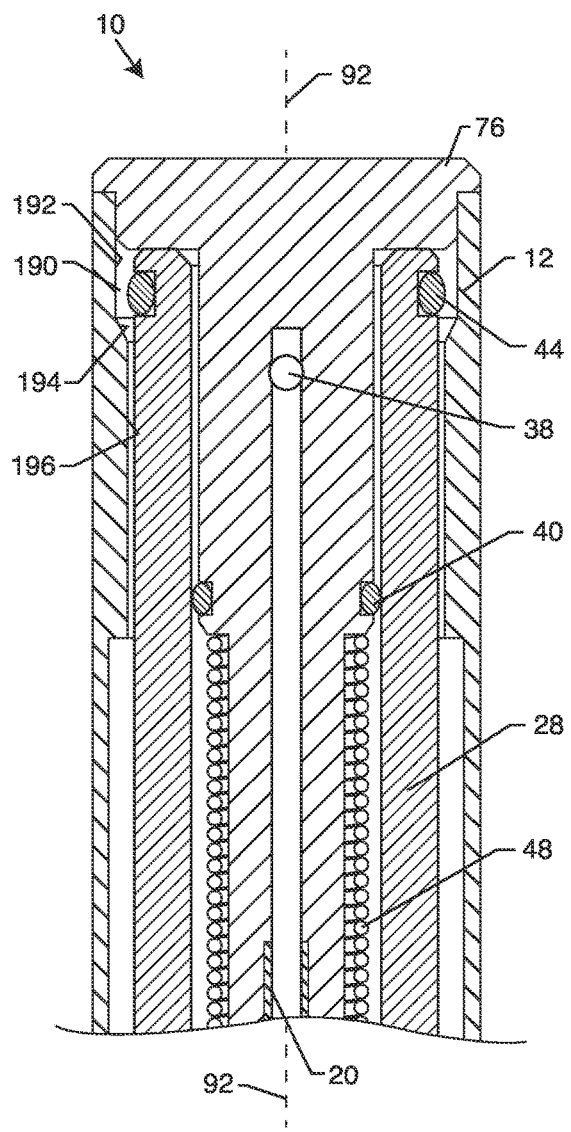
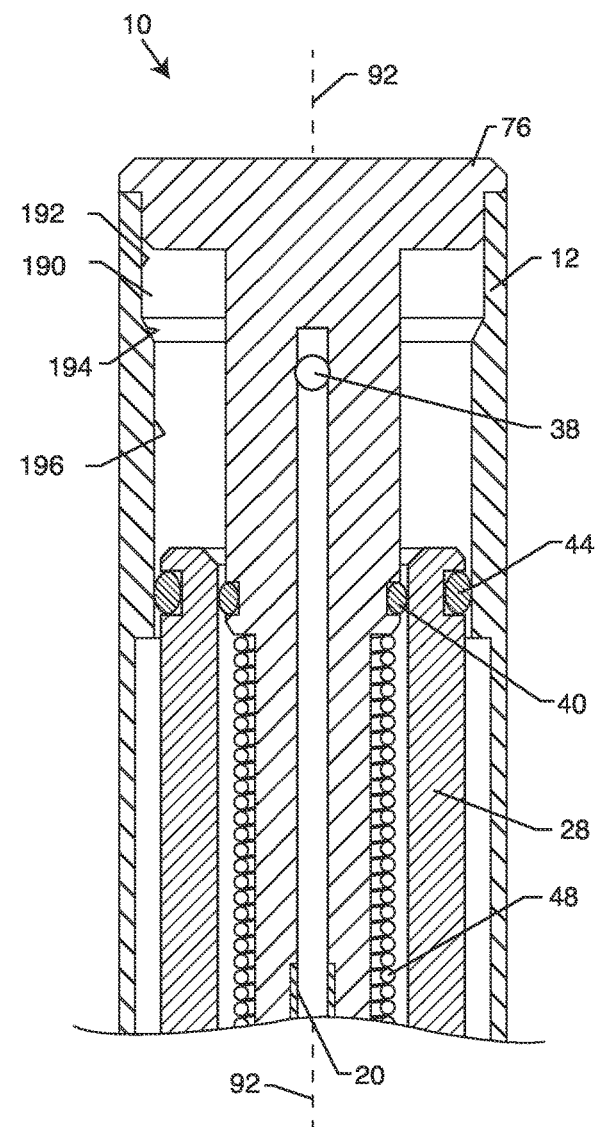
FIG. 64A
FIG. 64B

INTRAVASCULAR CATHETER INSERTION DEVICE

CROSS-REFERENCE TO RELATED APPLICATIONS

This continuation-in-part application claims priority to application Ser. No. 16/192,756 filed on Nov. 15, 2018, which itself was a continuation-in-part application claiming priority to application Ser. No. 15/230,333 filed on Aug. 5, 2016 and is now U.S. Pat. No. 10,136,917, which itself was a continuation-in-part application claiming priority to non-provisional application Ser. No. 14/326,088 filed on Jul. 8, 2014 and is now U.S. Pat. No. 9,433,758 issued on Sep. 6, 2016, which itself claimed priority to provisional application 61/844,349 filed on Jul. 9, 2013, the entire contents of which all applications are hereby fully incorporated by these references.

DESCRIPTION

Field of the Invention

The present invention generally relates to intravascular catheters. More particularly, the present invention relates to an intravascular catheter insertion device that automatically inserts a catheter upon a vacuum seal being broken that utilizes just one spring and two seals. Furthermore, this particular embodiment is configured to remove or overcome permanent deformation or stiction of a seal through the use of an annularly-shaped seal relief.

Background of the Invention

Properly inserting a catheter into a vein or artery is a very difficult process. It is not always easy for a technician, nurse or doctor to properly locate a vein or artery. Furthermore, it is also difficult to know how much pressure to apply to the needle. Many people have different densities of body tissue. Body tissue density can also change with a person's age. On top of these problems, the vein or artery the technician is trying to reach cannot be punctured on both sides. The vein may be very thin and it is easy to go through both sides of a vein. If the vein or artery is pierced on both sides it is no longer a proper vein or artery to use for the intended purpose. The technician must repeat the process adding significant discomfort and pain into the patient.

Typically, proper insertion of a catheter takes years of trial and error and skill. However, even the most experienced technicians, nurses or doctors are not able to consistently insert a catheter on the first try especially under stress or unstable conditions. Accordingly, there is a need for a new device that removes much of the guess work and skill of inserting a catheter into the vein or artery. The present invention fulfills these needs and provides other related advantages by inserting the catheter when the first side of a vein is pierced but before the second side of the vein is pierced.

SUMMARY OF THE INVENTION

An exemplary embodiment of a catheter insertion device (10) is best seen in FIGS. 64A and 64B. The catheter insertion device (10), includes: a hollow needle (20) having a distal skin-piercing end (22) opposite a proximal needle end (24), the hollow needle defining a channel (26) in fluidic and/or pneumatic communication between the distal skin-piercing end and the proximal needle end; a needle base (76), wherein the proximal needle end is attached to the needle base; a plunger (28) slidably disposed over at least a portion of the hollow needle, wherein the distal skin-piercing end of the hollow needle extends through a plunger distal end (32), the plunger having a plunger proximal end (30) opposite the plunger distal end; a compression spring (48) disposed concentric with and over at least a second portion of the hollow needle, the compression spring mechanically engaged directly and/or indirectly between at least a portion of the needle base and a portion of the plunger, the compression spring biasing the plunger away from the needle base; a catheter (50) slidably disposed over at least a third portion of the hollow needle, wherein the distal skin-piercing end of the hollow needle extends through a distal insertion end (52) of the catheter, the catheter comprising the distal insertion end opposite a proximal connection end (54), wherein a catheter surface (68) is configured to be contactable by the plunger distal end when the plunger moves in a forward direction; an expandable chamber (34) in fluidic and/or pneumatic communication with the channel of the hollow needle by an aperture (38) in the needle base, the expandable chamber at least partially delimited by the needle base and the plunger proximal end, wherein the expandable chamber is configured to increase in volume as the plunger moves towards the distal skin-piercing end of the hollow needle; wherein a longitudinal axis (92) is defined as extending along the hollow needle, the needle base, the plunger, the compression spring and the catheter, wherein the plunger is configured to move between a stored position, an armed position and an extended position, wherein the plunger at least rotates about the longitudinal axis between the stored position and armed position, and wherein the plunger at least translates along the longitudinal axis between the armed position and the extended position; a generally hollow housing (12), wherein the needle base, the plunger and the compression spring are at least partially disposed within the generally hollow housing in the stored position; a first circumferential seal (40) of the expandable chamber disposed between the needle base and the plunger, the first circumferential seal configured to seal the needle base to the plunger for a distance when the plunger moves away from the needle base; a second circumferential seal (44) of the expandable chamber disposed between the plunger and the generally hollow housing, wherein the second circumferential seal is configured to seal the generally hollow housing to the plunger for the distance when the plunger moves away from the needle base; wherein the generally hollow housing includes an annularly-shaped seal relief (190) formed as an inside surface (192) of the generally hollow housing, wherein the second circumferential seal in the stored position is aligned along the longitudinal axis with the annularly-shaped seal relief where the second circumferential seal is not in contact with the inside surface (192) of the generally hollow housing. In further embodiments, the inside surface (192) may be adjacent to a transition surface (194) which itself may be adjacent to a second inside surface (196), wherein the inside surface (192) has a larger diameter in comparison to the second inside surface (196).

An exemplary embodiment of a catheter insertion device (10) is best seen in FIGS. 34-60. A hollow needle (20) has a distal skin-piercing end (22) opposite a proximal needle end (24). The hollow needle defines a channel (26) in fluidic and/or pneumatic communication between the distal skin-piercing end and the proximal needle end. A proximal needle end is attached to a needle base (76). A plunger (28) is slidably disposed over at least a portion of the hollow needle, wherein the distal skin-piercing end of the hollow needle extends through a plunger distal end (32). The plunger has a plunger proximal end (30) opposite the plunger distal end. A compression spring (48) is disposed concentric with and over at least a second portion of the hollow needle. The compression spring mechanically engages directly and/or indirectly between at least a portion of the needle base and a portion of the plunger, the compression spring biasing the plunger away from the needle base. A catheter (50) is slidably disposed over at least a third portion of the hollow needle, wherein the distal skin-piercing end of the hollow needle extends through a distal insertion end (52) of the catheter, the catheter comprising the distal insertion end opposite a proximal connection end (54). A catheter surface (68) is configured to be contactable by the plunger distal end when the plunger moves in a forward direction. An expandable chamber (34) is in fluidic and/or pneumatic communication with the channel of the hollow needle by an aperture (38) in the needle base, the expandable chamber at least partially delimited by the needle base and the plunger proximal end (30). The expandable chamber is configured to increase in volume as the plunger moves towards the distal skin-piercing end of the hollow needle.

In other exemplary embodiments, a longitudinal axis (92) may be defined as extending along the hollow needle, the needle base, the plunger, the compression spring and the catheter, wherein the plunger is configured to move between a stored position, an armed position and an extended position. The plunger rotates about the longitudinal axis between the stored position and armed position, and the plunger translates along the longitudinal axis between the armed position and the extended position.

In other exemplary embodiments a main housing (116) may be included, wherein the needle base, the plunger and the compression spring are at least partially disposed within the main housing in the stored position.

In other exemplary embodiments, a first circumferential seal (40) of the expandable chamber may be disposed between the needle base and the plunger, the first circumferential seal configured to seal the needle base to the plunger for a distance when the plunger moves away from the needle base. A second circumferential seal (44) of the expandable chamber may be disposed between the plunger and either of the main housing or a housing sleeve (114). The housing sleeve may be disposed within the main housing. The second circumferential seal may be configured to seal the housing or the housing sleeve to the plunger for the distance when the plunger moves away from the needle base. The housing sleeve may be a separately manufactured part in relation to the main housing.

In other exemplary embodiments, the main housing may include a front housing (110) and a rear housing (112), wherein the front housing is fixedly attached to a front portion (122) the main housing and wherein the rear housing is pivotably attached to a rear portion (124) of the main housing. The front housing may be a separately manufactured part in relation to the main housing, and wherein the rear housing may be a separately manufactured part in relation to the main housing.

In other exemplary embodiments, the catheter may be temporarily captured at the proximal connection end by the front housing with an interference fit.

In other exemplary embodiments, the front housing may be attached to the main housing by the use of a flexural snap feature (118) formed in the front housing that locks to a recess feature (120) formed in the main housing.

In other exemplary embodiments, a button (56) may be non-movably attached to the plunger and extending outwardly beyond the housing, wherein the button is configured to be manipulated by the user.

In other exemplary embodiments, the main housing and/or front housing may include an L-shaped slot (126), wherein the button of the plunger extends through and is movable within the L-shaped slot between the stored position, the armed position and the extended position. In the stored position the button is located at a distal lower end (128) of the L-shaped slot. In the armed position the button is located at a corner (130) of the L-shaped slot. In the extended position the button is located at a distal upper end (132) of the L-shaped slot.

In other exemplary embodiments, the button may move within the L-shaped slot between the distal lower end and the corner as it rotates about the longitudinal axis moving between the stored position and the armed position. The button may also move within the L-shaped slot between the corner and the distal upper end as it translates along the longitudinal axis moving between the armed position and the extended position.

In other exemplary embodiments, the plunger may translates along the longitudinal axis when a vacuum formed in the expandable chamber by the compression spring pushing the plunger away from the needle base is released by a fluid and/or a gas entering the channel of the hollow needle at the distal skin-piercing end.

In other exemplary embodiments, in the stored position a gap (66) may exists between the proximal connection end of the catheter and the plunger distal end.

In other exemplary embodiments, the plunger may include an outwardly extending tab (134) configured to be captured by a flexural lock feature (136) formed in the front housing when the plunger is in the extended position preventing the plunger moving backwards into the armed position.

In other exemplary embodiments, in the extended position a portion (138) of the plunger may contact a portion (140) of the front housing and/or main housing preventing the plunger from moving furthermore forwards beyond the front portion of the main housing.

In other exemplary embodiments, the expandable chamber may comprise a substantially zero volume when the plunger is in the stored and/or armed position.

In other exemplary embodiments, the rear housing may be movable from a needle start position (142) to a needle retracted position (144). In the needle start position a portion (146) of the rear housing abuts a portion (148) of the needle base preventing the compression spring from moving the needle base backwards towards the rear housing. In the needle retracted position the portion of the rear housing no longer abuts the portion of the needle base and the needle base and hollow needle are moved by the compression spring backwards into the rear housing wherein the distal skin-piercing end of the hollow needle is retracted within the plunger and/or front housing, thereby preventing the distal skin-piercing end of the hollow needle from inadvertent punctures.

Another exemplary embodiment of a catheter insertion device includes a hollow needle having a distal skin-piercing end opposite a proximal base end. The hollow needle defines a channel in fluidic or pneumatic communication between the distal skin-piercing end and the proximal base end. A plunger is slidably disposed over at least a portion of the hollow needle, where the distal skin-piercing end of the hollow needle extends through a distal end of the plunger. A spring is mechanically engaged between at least a portion of the proximal base end of the hollow needle and a portion of the plunger. The spring biases the plunger towards the distal skin-piercing end of the hollow needle. A catheter is slidably disposed over at least a second portion of the hollow needle where the distal skin-piercing end of the hollow needle extends through a distal insertion end of the catheter. The catheter includes the distal insertion end opposite a proximal connection end, where the proximal connection end of the catheter is configured to be disposed next to the distal end of the plunger. An expandable chamber has a first opening in fluidic or pneumatic communication with the channel of the hollow needle. The expandable chamber is at least partially formed by the proximal base end of the hollow needle and a proximal end of the plunger. The expandable chamber is configured to increase in volume as the plunger moves towards the distal skin-piercing end of the hollow needle.

In other exemplary embodiments a first circumferential seal of the expandable chamber may be disposed about the proximal base end of the hollow needle. The first circumferential seal may be configured to seal the proximal base end to the plunger when the plunger is moved to its furthest proximal position. A second circumferential seal of the expandable chamber may be disposed about the plunger, the second circumferential seal configured to seal the plunger to the housing when the plunger is moved to its furthest proximal position. A button may be non-movably attached to the plunger and extending outside of the housing. The seals can be either separate O-rings or separate seals, or alternatively, could be part of the structure and molded into the housing or plunger.

In other exemplary embodiments a housing may be attached to the proximal base end of the hollow needle. The housing may include a J-shaped slot, where the button is configured to be moveable within the J-shaped slot between a stored position, an armed position and an extended position. The stored position is when the button is located at a lower end of the J-shaped slot. The armed position is when the plunger is moved to its furthest proximal position or to a more proximal position. The extended position is when the plunger is moved to its furthest distal position. When in the armed position a small gap may be disposed between the proximal connection end of the catheter and the distal end of the plunger. This also allows the device to be reloadable as a medical technician can reload the device manually.

In other exemplary embodiments the plunger may include a circumferential recess and the housing may include a needle guard flexure having a distal engagement tip. When the plunger is in the extended position the distal engagement tip of the housing is captured within the circumferential recess of the plunger and the plunger is fixedly secured in relation to the hollow needle. The distal end of the plunger is then beyond the distal skin-piercing end of the hollow needle.

The first and second circumferential seals may be each configured to abut only one of either the plunger or the housing when the plunger is in the extended position and stored position.

The expandable chamber may have a substantially zero volume when the plunger is in the armed position.

Another exemplary embodiment of a catheter insertion device has a generally hollow housing having a closed base end opposite an open distal end. A hollow needle has a distal skin-piercing end opposite a proximal needle end. The distal skin-piercing end would typically have a sharp beveled end that is designed to easily penetrate bodily tissue such as the skin. The proximal needle end is non-movably attached to the closed base end of the generally hollow housing and the proximal needle end is disposed within the generally hollow housing. The distal skin-piercing end of the hollow needle extends beyond the open distal end of the generally hollow housing. The hollow needle defines a channel in fluidic or pneumatic communication between the distal skin-piercing end and the proximal needle end. A plunger is slidably disposed over at least a portion of the hollow needle. The plunger includes a plunger proximal chamber end opposite a plunger distal end. The distal skin-piercing end of the hollow needle extends through the plunger distal end. An expandable chamber is at least partially formed by the plunger proximal chamber end and at least an inside surface of the closed based end of the generally hollow needle, where the expandable chamber is in fluidic or pneumatic communication with the channel of the hollow needle through the proximal needle end. The expandable chamber is configured to increase in volume as the plunger moves towards the distal skin-piercing end of the hollow needle. A first seal is attached to either an inside surface of the plunger or the generally hollow housing. A second seal is attached to either an outside surface of the plunger and the generally hollow housing. The first seal is configured to seal between the inside surface of the plunger and the generally hollow housing when the plunger is at its furthest proximal position and the second seal is configured to seal between the outside surface of the plunger and the generally hollow housing when the plunger is at its furthest proximal position. A spring is mechanically engaged between the generally hollow housing and the plunger. The spring biases the plunger towards the distal skin-piercing end of the hollow needle. A catheter is slidably disposed over at least a second portion of the hollow needle where the distal skin-piercing end of the hollow needle extends through a distal insertion end of the catheter. The catheter includes the distal insertion end opposite a proximal connection end, where the proximal connection end of the catheter is configured to be disposed next to the plunger distal end.

In other exemplary embodiments a button may be non-movably attached to the plunger and extends outside of the generally hollow housing. The housing may include a J-shaped slot, where the button is configured to be moveable within the J-shaped slot between a stored position, an armed position and an extended position. The stored position is when the button is located at a lower end of the J-shaped slot. The armed position is when the plunger is moved to its furthest proximal position. The extended position is when the plunger is moved to its furthest distal position. The armed position has a small gap is disposed between the proximal connection end of the catheter and the plunger distal end.

The plunger may have a circumferential recess where then the generally hollow housing has a needle guard flexure having a distal engagement tip, wherein when the plunger is in the extended position the distal engagement tip of the generally hollow housing is captured within the circumferential recess of the plunger. The plunger is then fixedly secured in relation to the hollow needle. The plunger distal end is positioned beyond and covers the distal skin-piercing end of the hollow needle.

The first and second circumferential seals may each be configured to abut only one of either the plunger or the housing when the plunger is in the stored and extended position.

The proximal connection end of the catheter may engage the open distal end of the generally hollow housing, where movement of the catheter towards the closed base end of the generally hollow housing is prevented when the plunger moves towards the closed base end of the generally hollow housing when the plunger moves from the stored position to the armed position.

Another exemplary embodiment of a catheter insertion device includes an elongated hollow needle having a distal skin-piercing end opposite a proximal needle end. The proximal needle end is non-movably fixed to a needle base, where the elongated hollow needle defines a channel in fluidic or pneumatic communication between the distal skin-piercing end and the proximal needle end. A generally hollow housing has an open distal end opposite a housing proximal end. The needle base is non-movably attached to the housing proximal end. A plunger is translatably disposed over at least a portion of the elongated hollow needle, where the distal skin-piercing end extends through a plunger distal end. A spring is mechanically engaged between the plunger and either the housing proximal end or the needle base. The spring is configured to bias the plunger towards the distal skin-piercing end. A catheter is translatably disposed over at least a second portion of the elongated hollow needle. The catheter includes a distal insertion end opposite a proximal connection end, where the distal skin-piercing end extends through the distal insertion end of the catheter. The proximal connection end of the catheter is configured to be disposed next to the plunger distal end. An expandable chamber is formed by a proximal plunger end of the plunger, an outside surface of the needle base and an inside surface of the housing proximal end. The expandable chamber varies in volume according to translational movement of the plunger A first seal is disposed around the outside surface of the needle base and a second seal is disposed around an outside surface of the plunger.

In other exemplary embodiments the plunger may be manually moveable between a stored position and an armed position, where the armed position includes the chamber having a substantially zero (or very low) volume as the plunger is in its furthest proximal position. When the plunger is in the armed position, the first seal may be disposed between the outside surface of the needle base and an inside surface of the plunger, and the second seal may be disposed between the outside surface of the plunger and the inside surface of the housing proximal end.

Another exemplary embodiment of a catheter insertion device includes a generally hollow housing having an open distal end opposite a housing base end. A hollow needle has a distal skin-piercing end opposite a proximal needle end. The hollow needle defines a channel in fluidic or pneumatic communication between the distal skin-piercing end and the proximal needle end. The proximal needle end is non-movably attached to the housing base end and the distal skin-piercing end of the hollow needle extends beyond the open distal end of the generally hollow housing. A plunger is slidably disposed over at least a portion of the hollow needle. The plunger includes a plunger proximal end opposite a plunger distal end, where the distal skin-piercing end of the hollow needle extends through the plunger distal end. A spring is mechanically engaged between the generally hollow housing and the plunger. The spring biases the plunger towards the distal skin-piercing end of the hollow needle. An expandable chamber is defined at least partially by the plunger proximal end and an inside surface of the housing base end. The expandable chamber is in fluidic or pneumatic communication with the channel of the hollow needle, where the expandable chamber is configured to increase in volume when the vacuum is broken and the plunger move towards the distal skin-piercing end of the hollow needle.

In other exemplary embodiments a first seal may be disposed between an outside surface of the plunger and the housing base end. A second seal may be disposed between an inside surface of the plunger and the housing base end. A catheter may be slidably disposed over at least a second portion of the hollow needle where the distal skin-piercing end of the hollow needle extends through a distal insertion end of the catheter. The catheter may include the distal insertion end opposite a proximal connection end, where the proximal connection end of the catheter is configured to be disposed next to the plunger distal end.

Another exemplary embodiment of the present invention of a catheter insertion device includes a hollow needle having a distal skin-piercing end opposite a proximal base end, the hollow needle defining a channel in fluidic or pneumatic communication between the distal skin-piercing end and the proximal base end, the hollow needle extending along a longitudinal axis. A plunger is slidably disposed over at least a portion of the hollow needle, where the distal skin-piercing end of the hollow needle extends through a distal end of the plunger. A spring is mechanically engaged between at least a portion of the proximal base end of the hollow needle and a portion of the plunger, the spring biasing the plunger towards the distal skin-piercing end of the hollow needle. A catheter is slidably disposed over at least a second portion of the hollow needle where the distal skin-piercing end of the hollow needle extends through a distal insertion end of the catheter, the catheter comprising the distal insertion end opposite a proximal connection end, where a surface of the catheter contacts the distal end of the plunger during catheter insertion. An expandable chamber has a first opening in fluidic or pneumatic communication with the channel of the hollow needle, the expandable chamber at least partially formed by the proximal base end of the hollow needle and a proximal end of the plunger, the expandable chamber configured to increase in volume as the plunger moves towards the distal skin-piercing end of the hollow needle. A housing is attached to the proximal base end of the hollow needle, the housing having an open distal end opposite the proximal base end of the hollow needle. A first circumferential seal of the expandable chamber is disposed about the proximal base end of the hollow needle, the first circumferential seal configured to seal the proximal base end to the plunger when the plunger is moved to its furthest proximal position. A second circumferential seal of the expandable chamber is disposed about the plunger, the second circumferential seal configured to seal the plunger to the housing when the plunger is moved to its furthest proximal position. A button is non-movably attached to the plunger and extending outside of the housing. The housing includes a slot, wherein the slot extends from a slot open end to a slot closed end with a slot turn there between, wherein the slot open end is located at the open distal end of the housing, wherein at least a portion of the slot extending from the slot open end to the slot turn is non-linear with respect to the longitudinal axis of the hollow needle, the slot turn changing direction of the slot between the slot open end and the slot closed end. The plunger moves with the button and a portion of the button is configured to be moveable within the slot between a stored position, an armed position and an extended position, wherein the stored position comprises when the portion of the button is located at the slot closed end, wherein the armed position comprises when the portion of the button is located at the slot turn, and wherein the extended position comprises when the portion of the button is located at and/or past the slot open end. The plunger is configured to rotate about the longitudinal axis of the needle as the portion of the button passes through the non-linear portion of the slot.

In other exemplary embodiments, the plunger at the plunger distal end may comprise a male rotation coupling feature, and wherein the catheter at the proximal connection end comprises a female rotation coupling feature, wherein the male and female rotation coupling features are configured to rotatably move the catheter in unison with the plunger as the plunger rotates about the longitudinal axis of the needle as the portion of the button passes through the non-linear portion of the slot.

In other exemplary embodiments, the plunger at the plunger distal end may comprise a first rotation coupling feature, and wherein the catheter at the proximal connection end comprises a second rotation coupling feature, wherein the first and second rotation coupling features are configured to rotatably move the catheter in unison with the plunger as the plunger rotates about the longitudinal axis of the needle as the portion of the button passes through the non-linear portion of the slot.

In other exemplary embodiments, the plunger and/or the catheter may include a means for rotatably coupling the plunger and the catheter in rotational unison as the plunger rotates as it moves from the armed position to the extended position.

In other exemplary embodiments, the armed position may have a small gap is disposed between the proximal connection end of the catheter and the distal end of the plunger.

In other exemplary embodiments, the plunger may comprise a circumferential recess, and wherein the housing may comprise a needle guard flexure having a distal engagement tip.

In other exemplary embodiments, the first and second circumferential seals may be each configured to abut only one of either the plunger or the housing when the plunger is in the extended position and stored position.

In other exemplary embodiments, the expandable chamber may comprise a substantially zero volume when the plunger is in the armed position.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 3 is another perspective view of the exemplary embodiment of FIG. 1;

FIG. 4 is a perspective view similar to FIG. 3 now with the cap removed;

FIG. 5 is a perspective view similar to FIG. 4 now with the housing removed;

FIG. 6 is a perspective view similar to FIG. 5 now with the catheter removed;

FIG. 7 is a perspective view similar to FIG. 6 now with the plunger removed and showing the spring in the extended position;

FIG. 8 is a perspective view similar to FIG. 7 now with the spring shown in the armed or stored position;

FIG. 9 is a perspective view similar to FIG. 7 or 8 now with the spring removed;

FIG. 12 is a perspective view of the plunger from FIGS. 1-11;

FIG. 13 is another perspective view of the plunger from FIGS. 1-11;

FIG. 14 is a perspective view of an exemplary needle base of the structure of FIGS. 1-13;

FIG. 14A is a sectional view taken along lines 14A-14A from FIG. 14;

FIG. 15 is a perspective view of an exemplary catheter of the structure of FIGS. 1-14;

FIG. 15A is a sectional view taken along lines 15A-15A from FIG. 15;

FIG. 16 is a perspective view of an exemplary housing of the structure of FIGS. 1-15;

FIG. 16A is a sectional view taken along lines 16A-16A from FIG. 16;

FIG. 42 is a perspective view similar to FIG. 34 now showing the button and plunger in the extended position;

FIG. 43 is a sectional perspective view of the structure of FIG. 42 taken along lines 43-43;

FIG. 54 is a perspective view of just a plunger;

FIG. 55 is a sectional perspective view of the structure of FIG. 54 taken along lines 55-55;

FIG. 56 is a perspective view of just a front housing;

FIG. 57 is a sectional perspective view of the structure of FIG. 56 taken along lines 57-57;

FIG. 58 is a side view of the front housing;

FIG. 59 is another side view the front housing;

FIG. 60 is a simplified schematic representation of the L-shaped slot of the present invention;

FIG. 64A is a partial sectional view of a new embodiment of the present invention in the stored position now showing an annularly-shaped seal relief; and FIG. 64B is a partial sectional view of the same structure as FIG. 64A but now in the armed position.

DETAILED DESCRIPTION OF THE PREFERRED EMBODIMENTS

This application discloses a new method and structure of inserting an intravascular (IV) catheter into the organic tissue, such as inserting an IV catheter into a vein or artery for blood withdrawal. This novel invention dramatically simplifies prior catheter designs (such as U.S. Pat. Nos. 5,313,361 and 5,480,388 and 5,527,290 which are fully incorporated herein with this reference) and dramatically increases the ability to properly insert the needle into a vein or artery.

This invention utilizes a single spring to create a vacuum chamber. When the needle is inserted under the skin, a spring is released and biases a plunger to move forward. However, the plunger doesn't move forward because it is held back due to a vacuum chamber formed within the structure of the device and the skin. The skin is non-porous and helps to create part of the vacuum seal. When a vein, artery, potential space, or fluid filled space (examples: epidural, subdural, or sinus space) is reached by the needle, the vacuum created in the vacuum chamber is broken and the spring is able to then propel the plunger forward. As the plunger advances it pushes the catheter into the vein, artery, potentials space, or fluid filled space mentioned above. In this way, a vein or artery is never pierced on both sides. The success rate of a proper insertion of an IV catheter is thereby greatly increased. This leads to less patient discomfort and less time and anxiety in performing a proper catheter insertion.

The embodiments taught herein have been considerably simplified from prior art designs. These novel embodiments includes just two seals and one spring. There are also fewer components that make up the assembly. Furthermore, most of the parts have also been designed to be made in a simple two part mold. The necessary parts comprise a needle, a needle base, a catheter, a housing, a plunger, a spring, two seals and a cap. As will be shown, the needle base could be integrated into the housing further reducing the part count. The improved design is significantly cheaper to manufacture and the reduction in parts increases the reliability of the device. The simplicity in design makes this device feasible to compete against the current products on the market.

Another novel aspect of this invention is that the plunger not only acts a piston advancing the catheter but it also acts as a needle guard once the catheter has been inserted. This novel combination of structure further helps to reduce parts and simplify the design.

Figure 1:
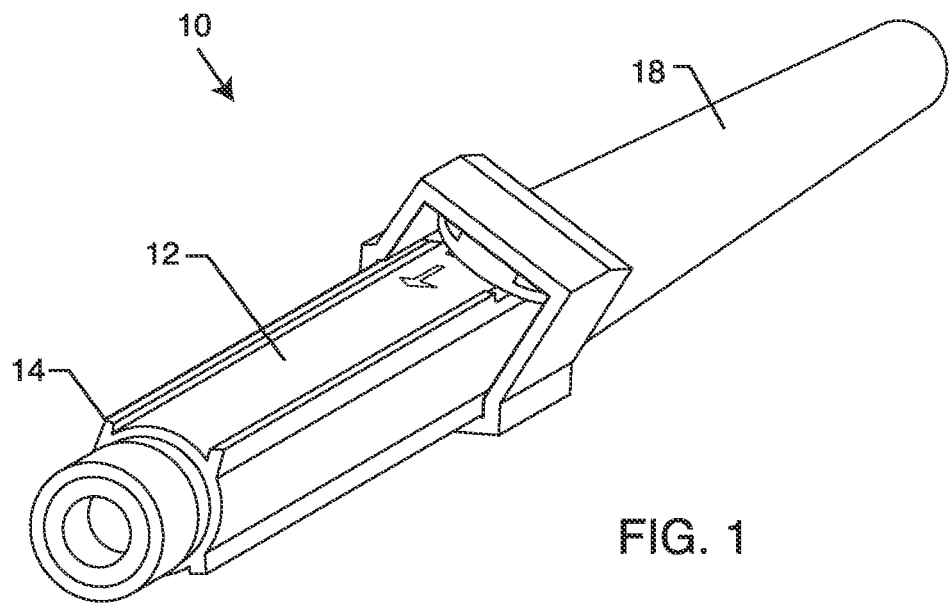
FIG. 1 is a perspective view of an exemplary catheter insertion device of the present invention.
Figure 2:
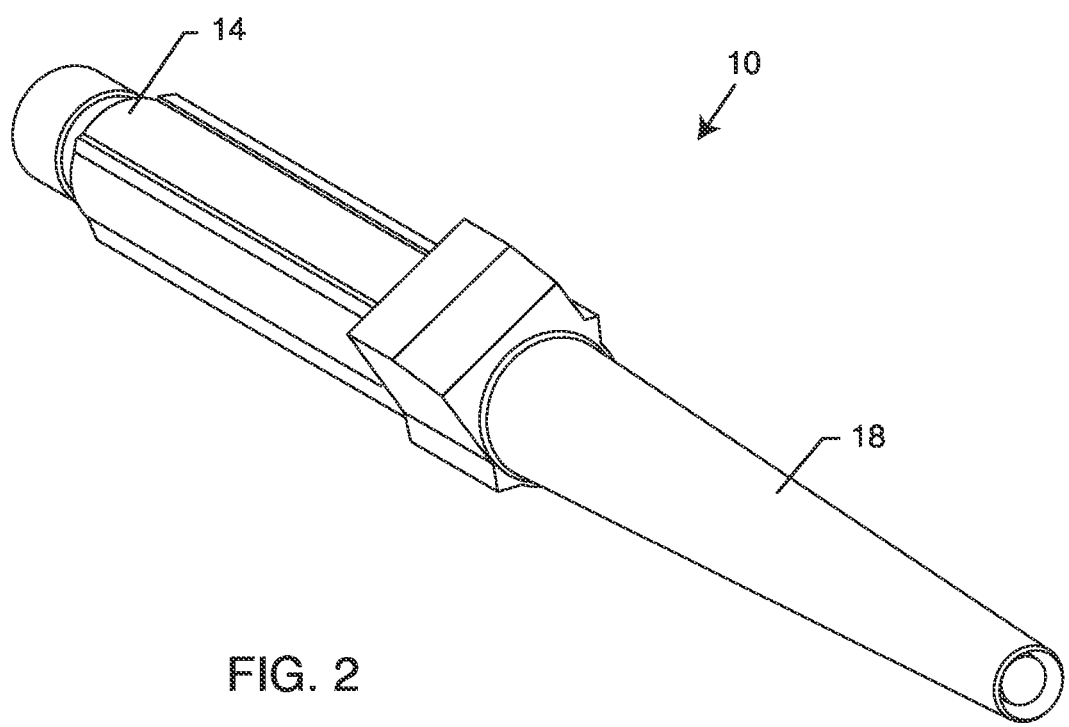
FIG. 2 is another perspective view of the exemplary embodiment of FIG. 1.

As shown in FIGS. 1-16, an exemplary embodiment of a catheter insertion device 10 has a generally hollow housing 12 having a closed base end 14 opposite an open distal end 16. As shown in FIGS. 1-3 a cap 18 is shown connected to the distal end 16. When the device is about to be used, the cap 18 is removed which exposes the hollow needle 20, as is seen in FIG. 4.

Figure 11:
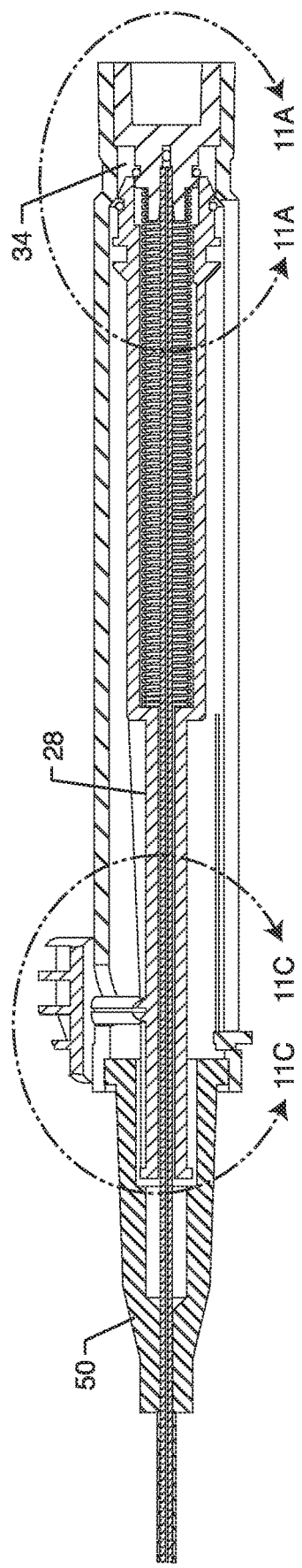
FIG. 11 is sectional side view of the structure of FIG. 4 taken along lines 11-11
Figure 11A:
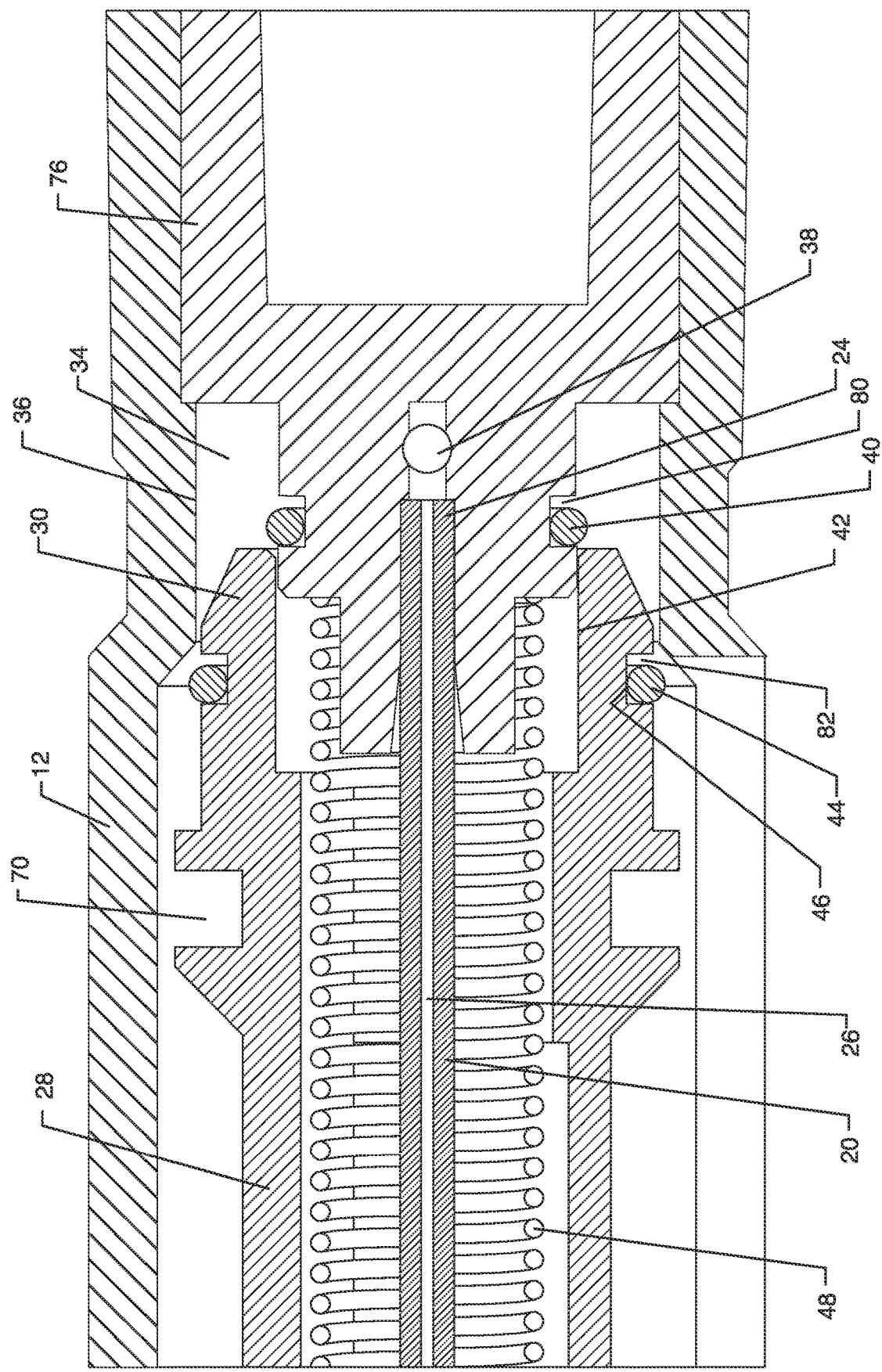
FIG. 11A is an enlarged view of the section taken along lines 11A-11A from FIG. 11 showing the plunger in the stored position.

The hollow needle 20 has a distal skin-piercing end 22 opposite a proximal needle end 24. The proximal needle end 24 is non-movably attached to the closed base end 14 of the generally hollow housing 12 where the proximal needle end 24 is disposed within the generally hollow housing 12, as is best shown in FIG. 11A. In these embodiments, the needle's proximal needle end 24 is inserted into a proximal base end/needle base 76. The needle base 76 may be formed as part of the closed base end 14 of the housing 12 or may be a separate part as shown herein. As shown in FIGS. 14 and 14A the proximal base end/needle base 76 has a hole 78 for the proximal needle end 24 to be secured and fixedly attached. The needle base 76 is then permanently secured within the closed base end 14 of the housing 12 to then close it. The needle base 76 may be glued or bonded to the housing 12, or alternatively could be an interference fit or even as another alternative they could be screwed into each other with a male-female threaded ends. As shown herein, the needle base 76 is constructed as a separate part because it is easier to then place the aperture 38 within the needle base 76. This aperture 38 is an important aspect of the invention as it creates a path for the vacuum to be communicated during operation of the device. Furthermore, the proximal needle end 24 could be glued, bonded, molded, screwed or attached to the needle base 76/closed base end 14 of the housing 12 by an interference fit.

As shown in FIG. 4, the distal skin-piercing end 22 of the hollow needle 20 extends beyond the open distal end 16 of the generally hollow housing 12. The hollow needle 20 defines a channel 26 in fluidic or pneumatic communication between the distal skin-piercing end 22 and the proximal needle end 24. A plunger 28 is then slidably disposed over at least a portion of the hollow needle 20. The plunger 28 slides along the needle 20, or it can be said that the plunger 28 translates or moves along the needle. As shown herein, the plunger 28 can also rotate about the needle 20, yet rotation is not a necessary requirement. For instance, the plunger 28 and housing 12 could be constructed in a square or rectangular manner as compared to the circular version shown herein. It is simply easier to manufacture and assemble the circular version as orientation in assembly and use is not as critical.

Figure 11B:
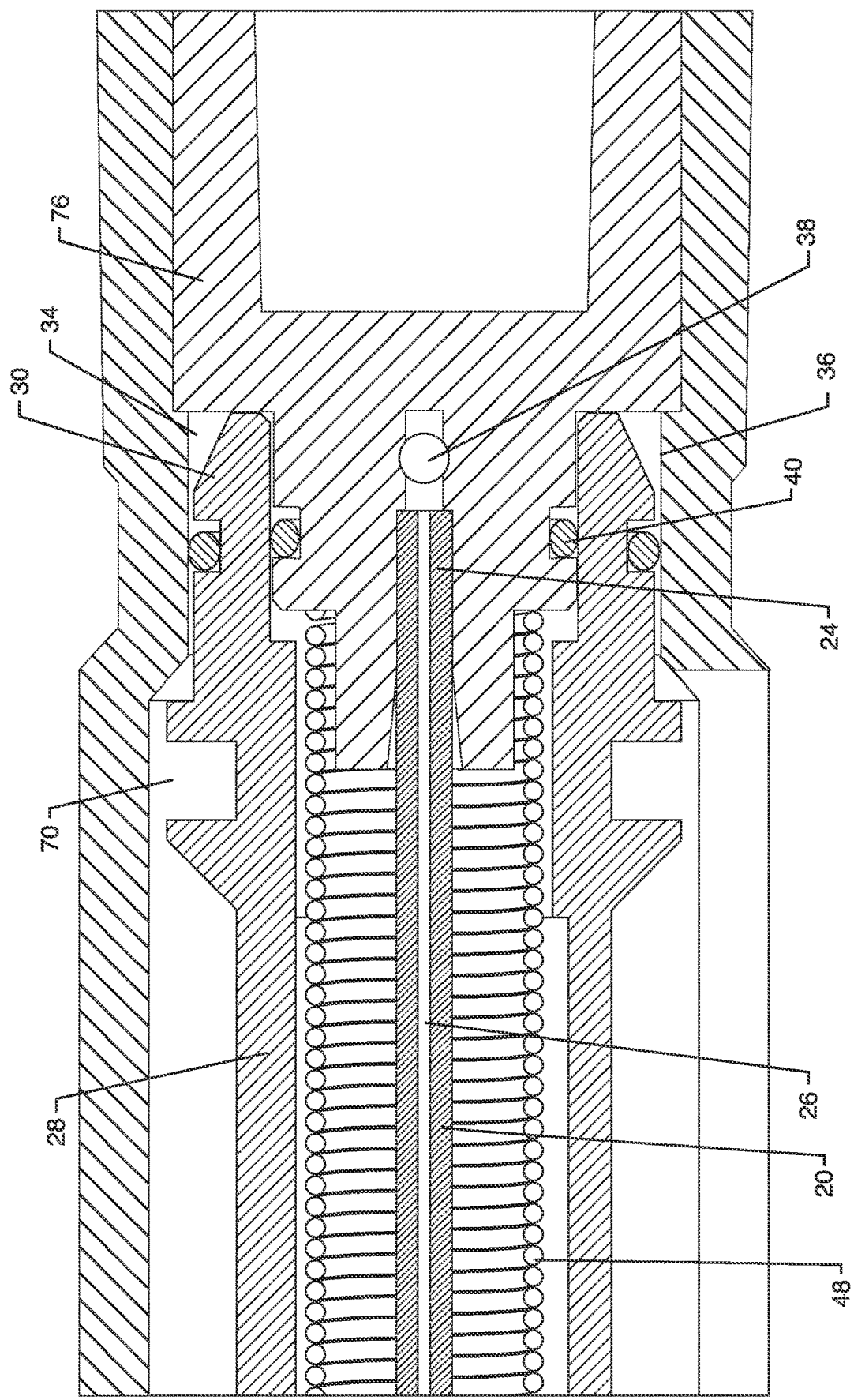
FIG. 11B is a view similar to FIG. 11A now showing the plunger in the armed position.

The plunger 28 includes a plunger proximal chamber end 30 opposite a plunger distal end 32. The distal skin-piercing end 22 of the hollow needle 20 extends through the plunger distal end 32. As best shown in FIGS. 11A and 11B, an expandable chamber 34 is at least partially formed by the plunger proximal chamber end 30 and at least an inside surface 36 of the closed based end of the generally hollow needle 20. The expandable chamber 34 is in fluidic or pneumatic communication with the channel 26 of the hollow needle 20 through the proximal needle end 24, where the aperture/hole 38 may be located. The expandable chamber 34 is configured to increase in volume as the plunger 28 moves towards the distal skin-piercing end 22 of the hollow needle 20.

A first seal 40 is attached to either an inside surface 42 of the plunger 28 or the generally hollow housing 12/needle base 76. A second seal 44 is attached to either an outside surface 46 of the plunger 28 or the generally hollow housing 12. The first seal 40 is configured to seal between the inside surface 42 of the plunger and the generally hollow housing 12/needle base 76 when the plunger 28 is at its furthest proximal position and the second seal 44 is configured to seal between the outside surface 46 of the plunger and the generally hollow housing 12 when the plunger 28 is at its furthest proximal position. As shown herein, each seal may be an O-ring or other suitable structure, whether it be a rectangular, square or circular in section. To keep each seal in its required position, each seal has been assembled into a channel. For instance, the needle base 76 has a circumferential channel 80 that captures the first seal 40. The plunger 28 also has a circumferential channel 82 for capturing the second seal 44. As can be understood by those skilled in the art, the channels 80 and 82 could be formed on the opposing surface and the device would function similarly. Furthermore, the channels could be removed and the device would function similarly.

A spring 48 is mechanically engaged between the generally hollow housing 12/needle base 76 and the plunger 28. The spring 48 biases the plunger 28 towards the distal skin-piercing end 22 of the hollow needle 20. A catheter 50 is slidably disposed over at least a second portion of the hollow needle 20 where the distal skin-piercing end 22 of the hollow needle 20 extends through a distal insertion end 52 of the catheter 50. The catheter 50 includes the distal insertion end 52 opposite a proximal connection end 54, where the proximal connection end 54 of the catheter 50 is configured to be disposed next to the plunger distal end 32.

A button 56 is non-movably attached to the plunger 28 and extends outside of the generally hollow housing 12. The housing 12 may include a J-shaped slot 58, where the button 56 is configured to be moveable within the J-shaped slot 58 between a stored position 60, an armed position 62 and an extended position 64. This is best seen in FIG. 16. The stored position 60 is when the button is located at a lower end of the J-shaped slot 58. The armed position 62 is when the plunger 28 is moved to its furthest proximal position at the very bottom of the J-shaped slot. The extended position 64 is when the plunger 28 is moved to its furthest distal position.

One skilled in the art will understand that the button 56 may be removed altogether or even relocated onto another part while the invention would still be configured to function properly. For instance, the button 56 may be integrated onto the housing 12 and still control the movement of the plunger 28. Furthermore, the shape of the J-shaped slot 58 may also be modified or even removed. For instance, the plunger 28 may be preloaded during manufacture. The user would then press a button 56 or engage some sort of release once the distal skin-piercing end 22 has penetrated the patient's skin. Therefore, in this embodiment the slot has been completely removed.

When the cap 18 is on the device 10 the button 56 has been moved to the stored position 60. This means that the spring 48 has been compressed and an internal bias is already present within the device. The stored position 60 corresponds to the sectional view of FIG. 11A. It is important to note that in the stored position 60, the seals 40 and 44 are not in contact with two surfaces. The structure has been designed such that the seals are only captured within their respective channels. This is important because the seals could create an amount of static friction or stickiness that prevents the device from operating correctly. It was discovered that the seals tends to flow like a fluid even though they are made from rubber or rubberlike materials. If placed between two surfaces for a long period of time they tend to stick and hold the two surfaces together. This would impede proper operation of the device 10 if they were stored for a long period of time between two surfaces. Therefore, in the stored position 60, the seals are not sealing to their second surface but rather are captured in their primary channels ready to be used as a seal.

FIG. 11B then corresponds to the armed position 62 where the cap 18 is removed and the plunger 28 has been retracted by the user through the button 56. The user can then insert into the skin the distal skin-piercing end 22 of the needle 20 and let go of the button 56. As can be seen in FIG. 11B, the expandable chamber 34 has substantially zero-volume or very little volume. The seals 40 and 44 help to create and define the volume of the expandable chamber 34. Air or fluid is in communication, meaning it can flow freely, within the channel 26 of the needle 20 through the aperture 38 in the needle base 76 and to the expandable chamber 34.

As the user advances the needle 20 within the tissue of the patient the distal skin-piercing end 22 will eventually puncture into a vein or artery. When this happens, blood, fluid or air is able to then flow into the channel 26 and allow the expandable chamber 34 to expand. This means then that the plunger 28 is advancing forward. The spring 48 is now able to propel the plunger 28 forward a significant distance because the button 56 is able to slide to the extended position. The top of the J-shaped slot 58 is open, meaning the button 56 can pass through and keep moving forward. The plunger 28 is propelled forward which pushes the catheter 50 forward and into the vein or artery. Then the user can then push the soft catheter 50 all the way in as they withdraw the device 10 and leave the catheter 50 inserted into the patient.

The catheter 50 has a very flexible distal insertion end 52 that is designed to remain within the vein or artery. The proximal connection end 54 of the catheter 50 can then be connected to various other drug delivery devices or sample extraction devices as needed by the medical practitioner.

Figure 11C:
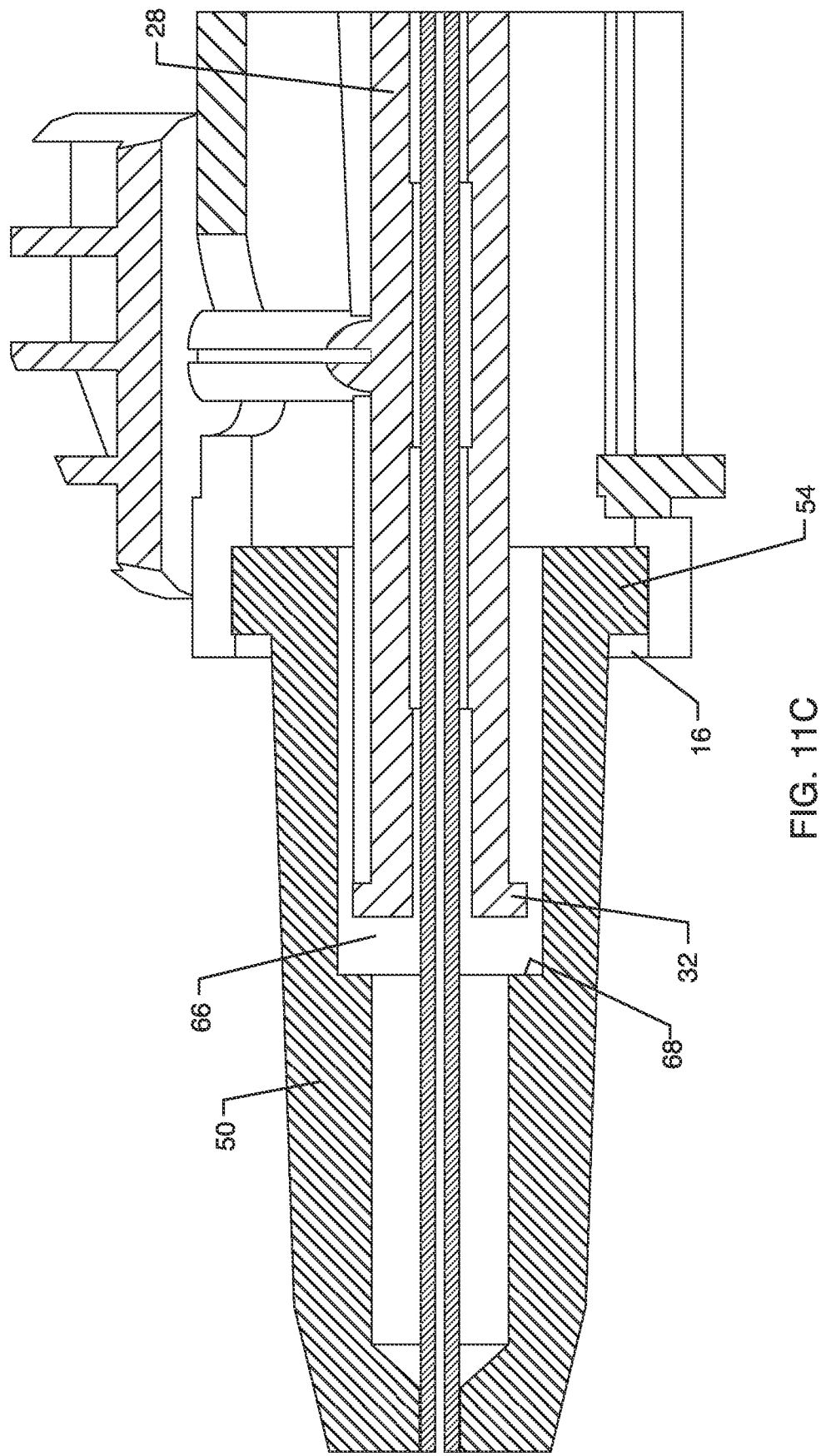
FIG. 11C is an enlarged view of the section taken along lines 11C-11C from FIG. 11.

Referring now to FIG. 11C, it is noted that in the armed position 62 there is a small gap 66 which is created between a catheter inner surface 68 and the plunger distal end 32. This gap 66 is important as it creates a space for the plunger 28 to start movement before it engages to the catheter 50. Momentum of the moving components is preferred for the device to operate optimally. Unrestricted movement is created after the vacuum in the expandable chamber 34 is broken. The plunger 28 is able to propel forward by the spring 48 and create momentum during the gap 66. Then when the plunger 28 strikes the catheter's inner surface 68 it can propel the catheter 50 forward. It is understood by those skilled in the art that the design could be changed where the plunger 28 hits the catheter 50 at a different location, such as at the proximal connection end 54 of the catheter 50.

As can be seen in FIG. 11C, the catheter 50 is loosely held at its proximal connection end 54 to the open distal end 16 of the housing 12. This is to make sure the catheter 50 does not slide and fall off the needle 20 when the cap 18 is removed. This also is used to prevent movement of the catheter 50 towards the closed base end 14 of the housing 12 when the plunger 28 is retracted into the armed position 62.

Figure 10:
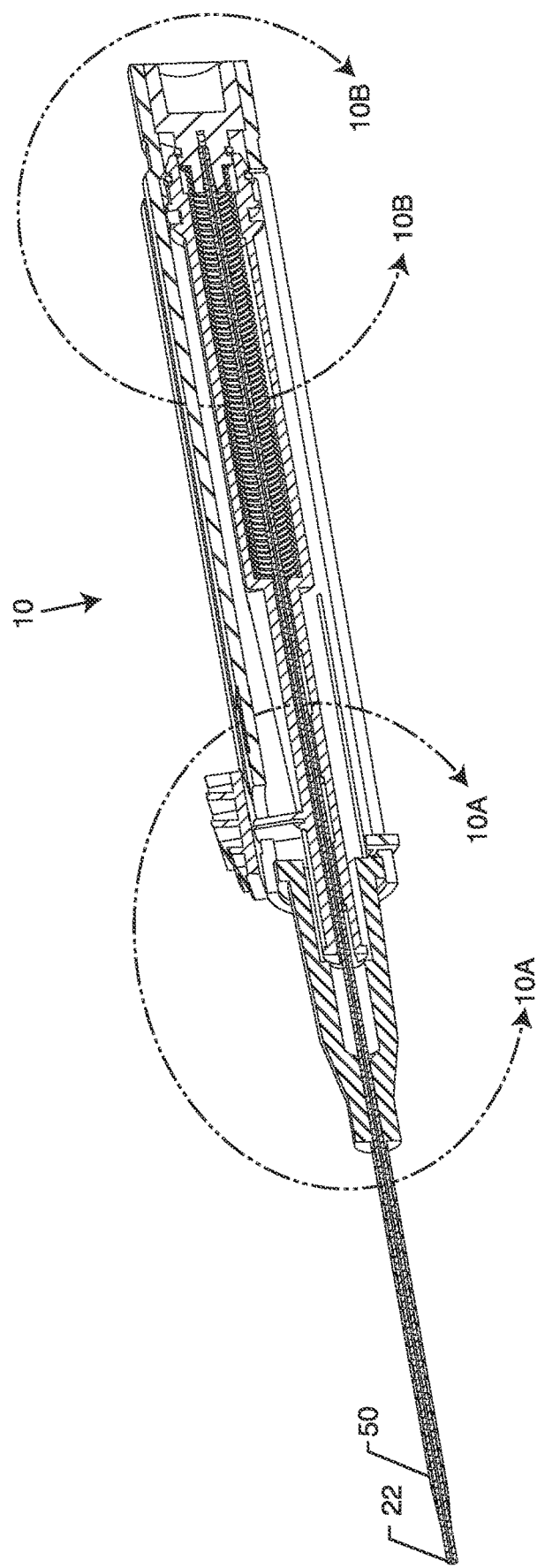
FIG. 10 is a sectional perspective view taken along lines 10-10 from FIG. 4.
Figure 10A:
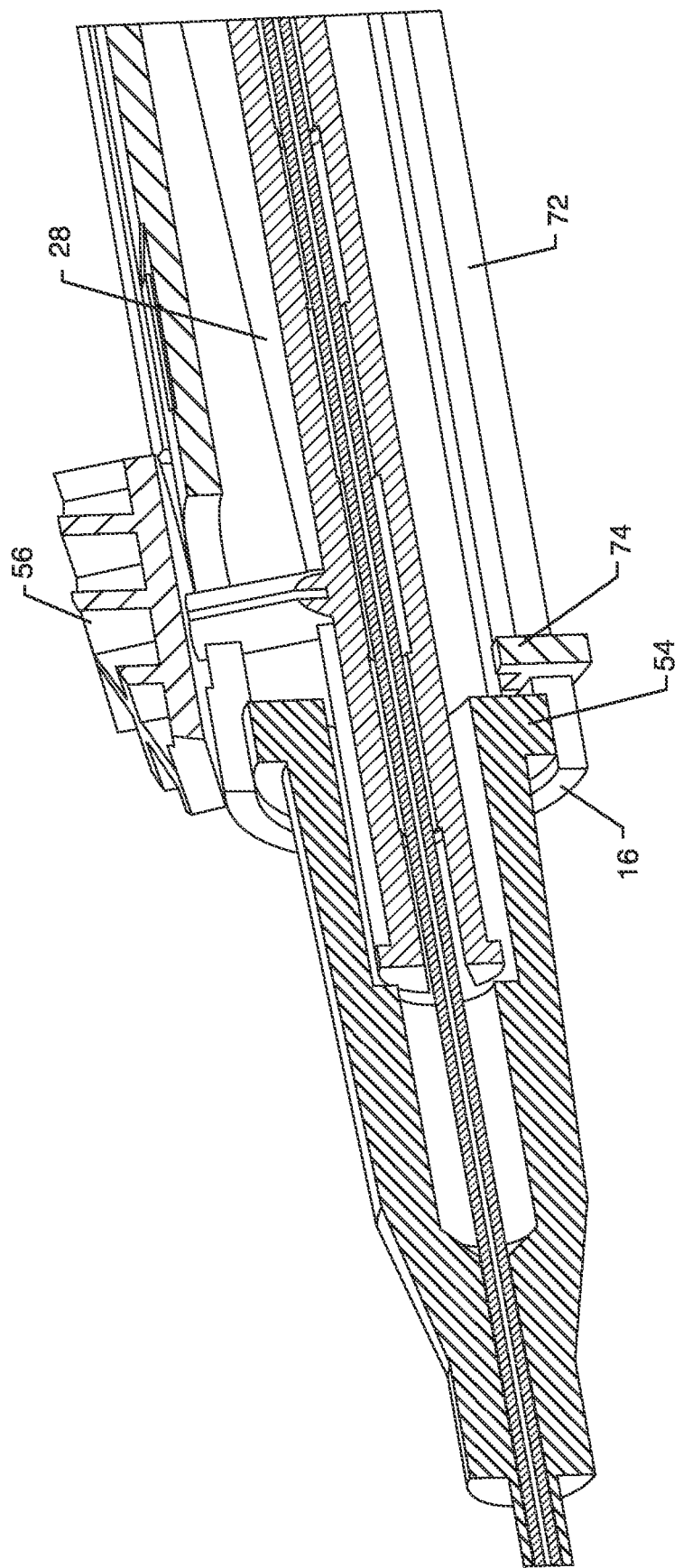
FIG. 10A is an enlarged view of the section taken along lines 10A-10A from FIG. 10.
Figure 10B:
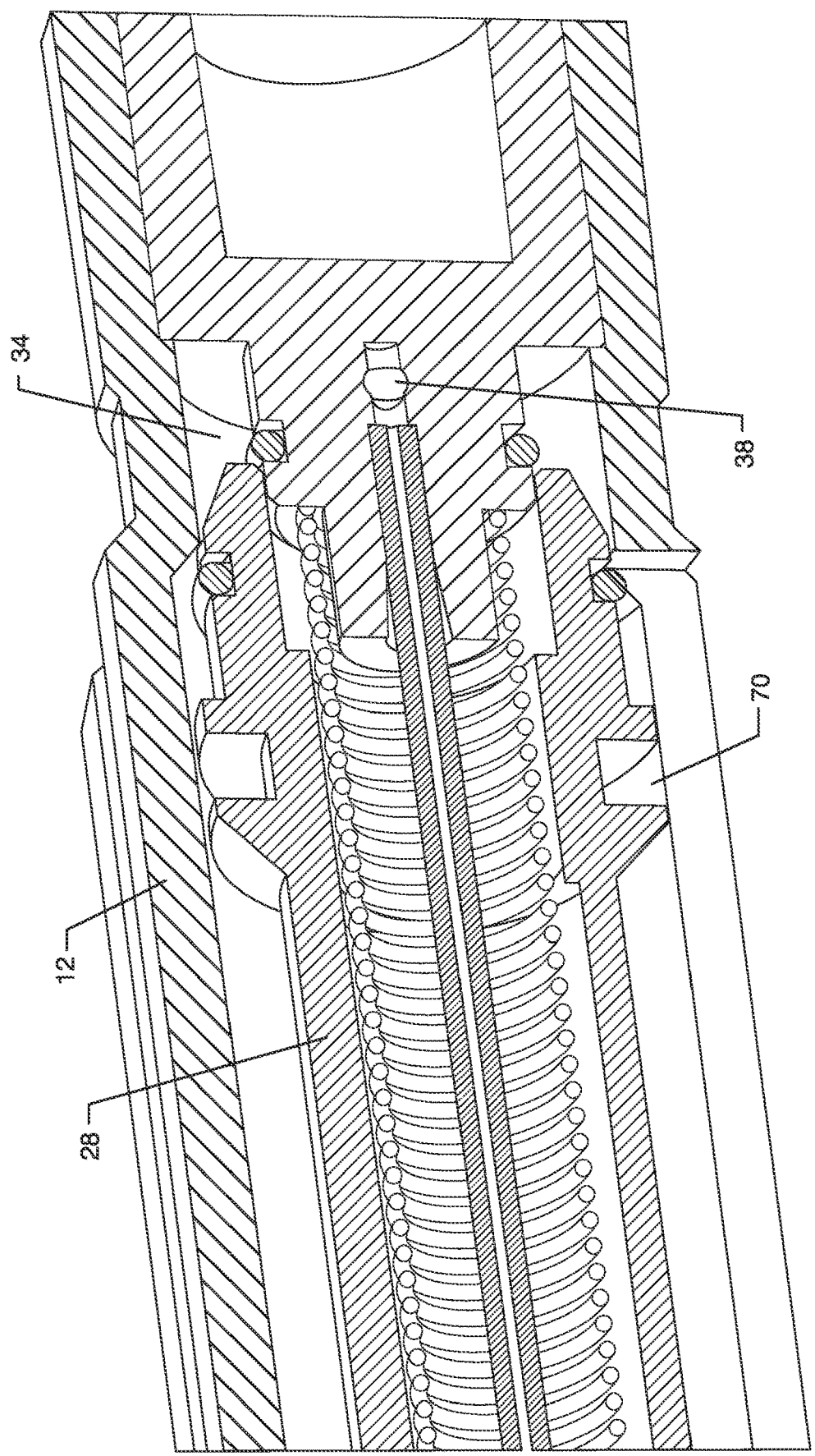
FIG. 10B is an enlarged view of the section taken along lines 10B-10B from FIG. 10.

As best seen in FIGS. 10A and 10B the plunger 28 may have a circumferential recess 70 allowing the plunger 28 to double in function as a needle guard. The generally hollow housing 12 has a needle guard flexure 72 having a distal engagement tip 74. When the plunger 28 is in the extended position 64 the distal engagement tip 74 of the housing 12 is captured within the circumferential recess 70 of the plunger 28. The plunger 28 is then fixedly secured in relation to the hollow needle 20 and the housing 12. The plunger distal end 32 is positioned beyond and covers the distal skin-piercing end 22 of the hollow needle 20.

It will be appreciated that to make the device 10 work properly there must be an optimum balance between all the forces acting within this novel structure. The spring rate must be formed such that it is enough the advance the plunger 28 forward when an artery or vein is reached, but not too strong that it prematurely overpowers the vacuum in the expandable chamber 34 and prematurely deploys the catheter 50. Also, the frictional force of the seals 40, 44 must not be too high that the spring 48 cannot advance the plunger 28 forward when an artery, vein, potential space, or fluid filled cavity is reached. This is why the J-shaped slot 58 allows the seals 40 and 44 to be free during storage in the stored position 60 and then engaged in the armed position 62. This prevents the seals from flowing into the abutting surfaces and sticking. For instance, if the seals were engaged during storage, the longer the product was stored the more the seals would stick, which is referred to herein as stiction. Due the delicate balances of forces for the invention to work properly, storing the seals in the armed position or a similar position could ruin the functionality of the catheter insertion device During testing, a preferred spring used herein had a calculated spring rate when extended of about 0.140 lbs./inch. A calculated maximum safe load was about 0.378 lbs. at 0.801 compressed (solid) height which corresponded to about 2.699 inches of travel. More specifically, another spring used herein had an outer diameter of 0.120 inches with a 0.009 inch thickness of music wire with about a 3.50 inch free length. The spring had about 97.54 total coils which is about a 0.0364 pitch. The spring rate of this preferred spring was 0.0628 lbs./inch. The ends of the spring were closed and not ground. The finish was a plain finish. One skilled in the art will understand that many variations from these preferred spring embodiments are possible for the device 10. The values disclosed herein could range for example by plus or minus ten percent, or even plus or minus twenty-five percent. For example, one skilled in the art could use springs rated at less than 0.50 lbs./inch, or preferably less than 0.25 lbs./inch, or preferably less than 0.125 lbs./inch. Also as an example, the springs may have an outer diameter less than 0.25 inches, or preferably less than 0.125 inches.

A novel feature of the present invention is the simplicity in the design. This structure only requires the use of just one spring 48. Furthermore, there are only two seals 40 and 44 used to create the vacuum within the expandable chamber 34. Furthermore, the plunger 28 also acts as a needle guard further simplifying the structure.

As can be best seen in FIGS. 16 and 16A, the housing has been formed such that the J-shaped slot 58 is formed therein and also the needle guard flexure 72 is formed therein. This simplifies the part count as extra parts are not required. As can best be seen in FIGS. 12 and 13, the plunger 28 has been formed with various slots and cutouts such that it can be made in a simple two part mold. Furthermore, the button 56 and the circumferential recess 70 has been integrated within to further simply the design by reducing the part count.

Figure 17A:
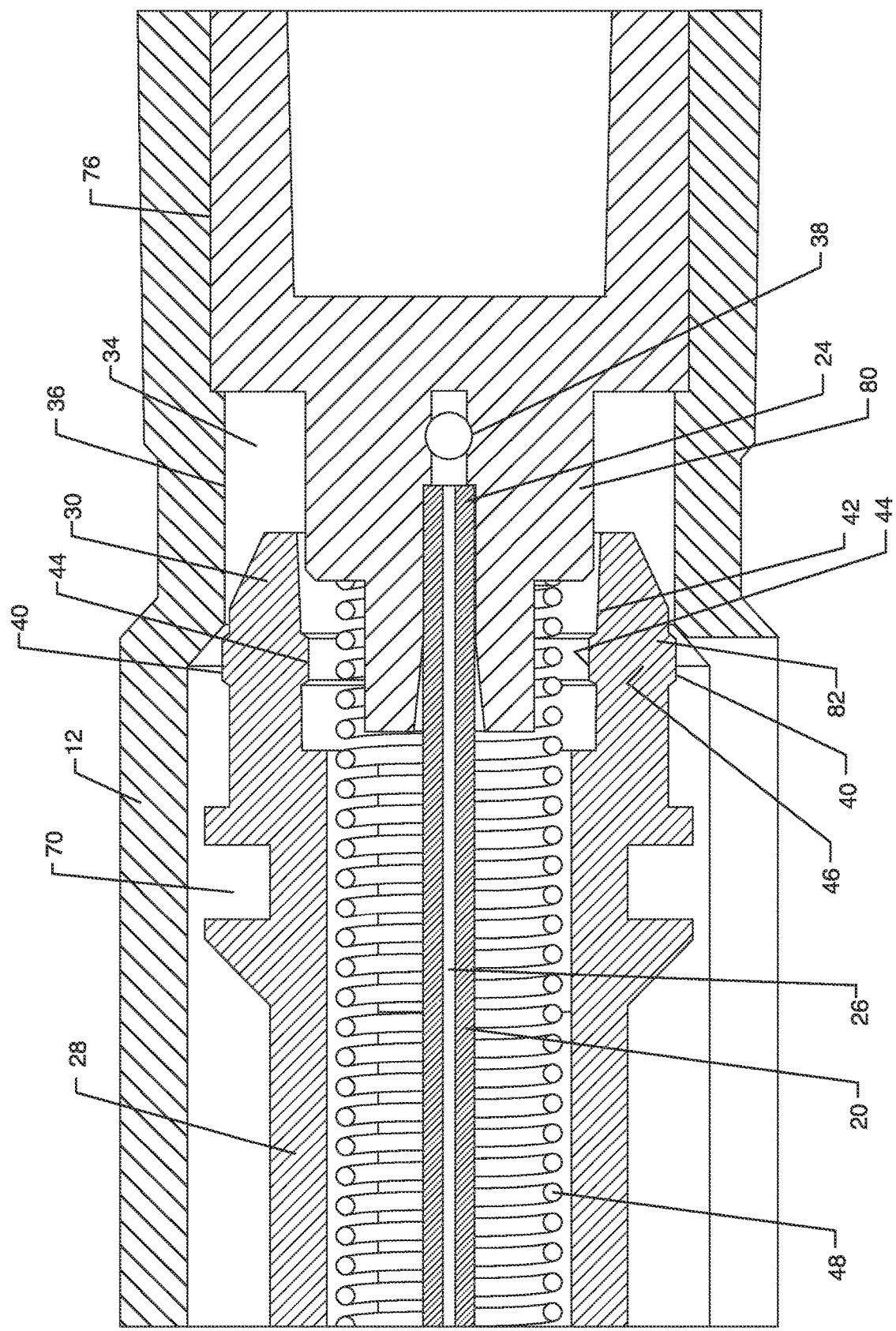
FIG. 17A is a view similar to 11A now showing a new embodiment of a seal design.
Figure 17B:
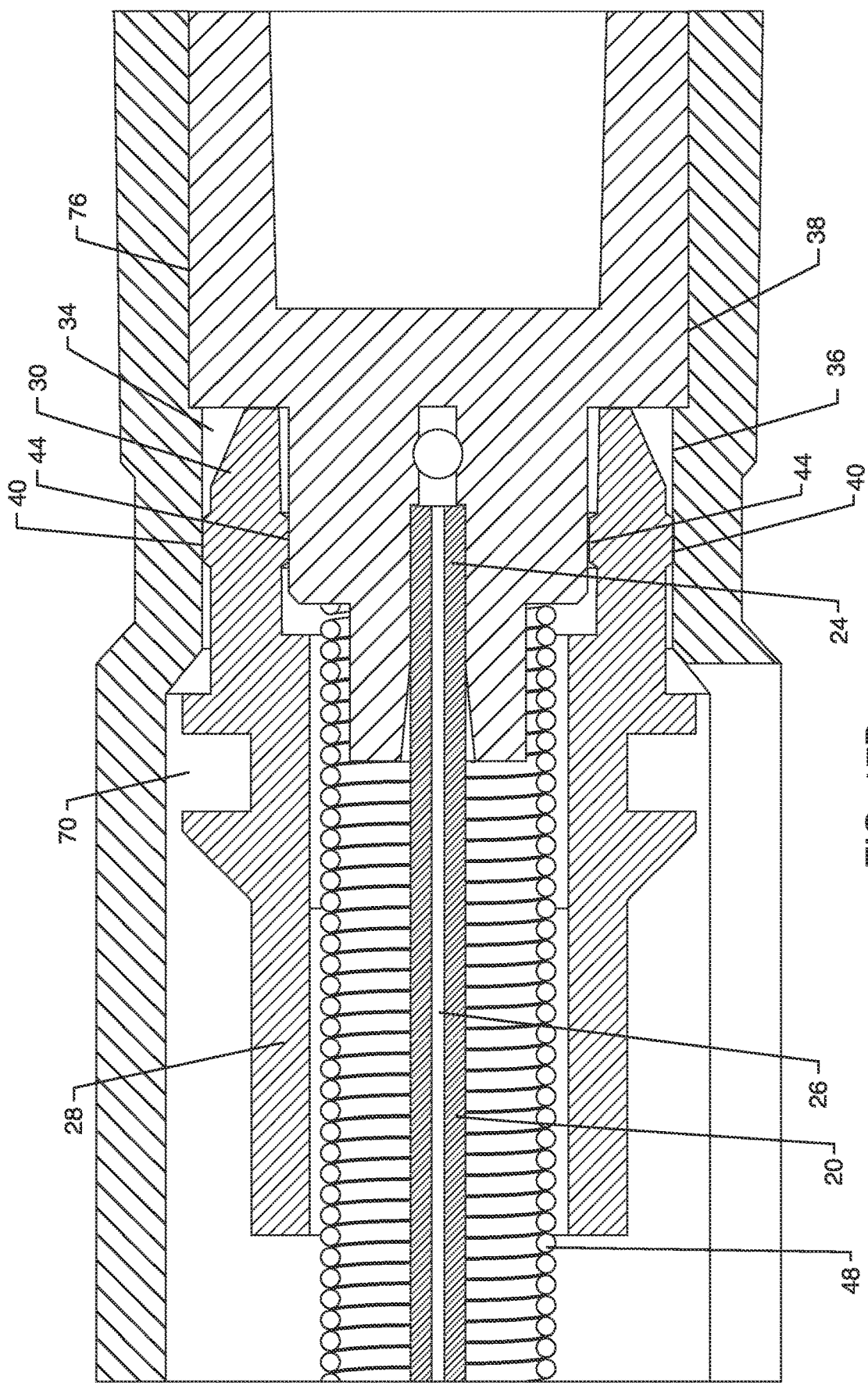
FIG. 17B is a view similar to 11B now showing the new seal design of the structure of FIG. 17A.

FIG. 17A is a view similar to 11A now showing a new embodiment of a seal design. FIG. 17B is a view similar to 11B now showing the new seal design of the structure of FIG. 17A. The end of the plunger 28 is now formed into a first seal 40 and a second seal 44. These seals may be formed as part of the plunger 28 itself or attached to the plunger as a separate piece/part. Rather than having the seals be stationary as in FIG. 11A and 11B, the seals 40 and 44 now move with the plunger 28. The seals 40 and 44 would be formed from a deformable and resilient material such as rubber or a seal-like material.

Figure 18A:
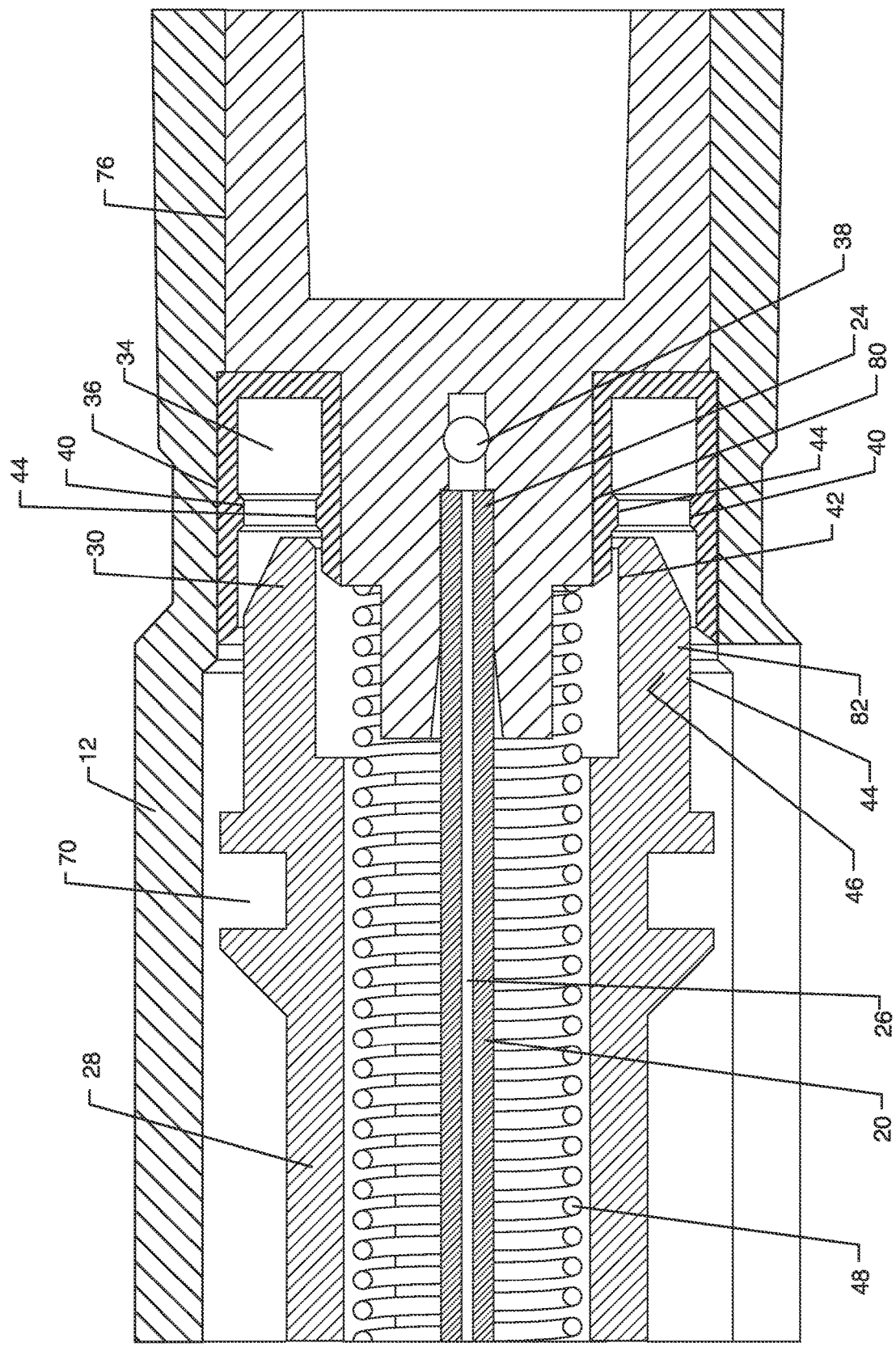
FIG. 18A is a view similar to 11A now showing a new embodiment of a seal design.
Figure 18B:
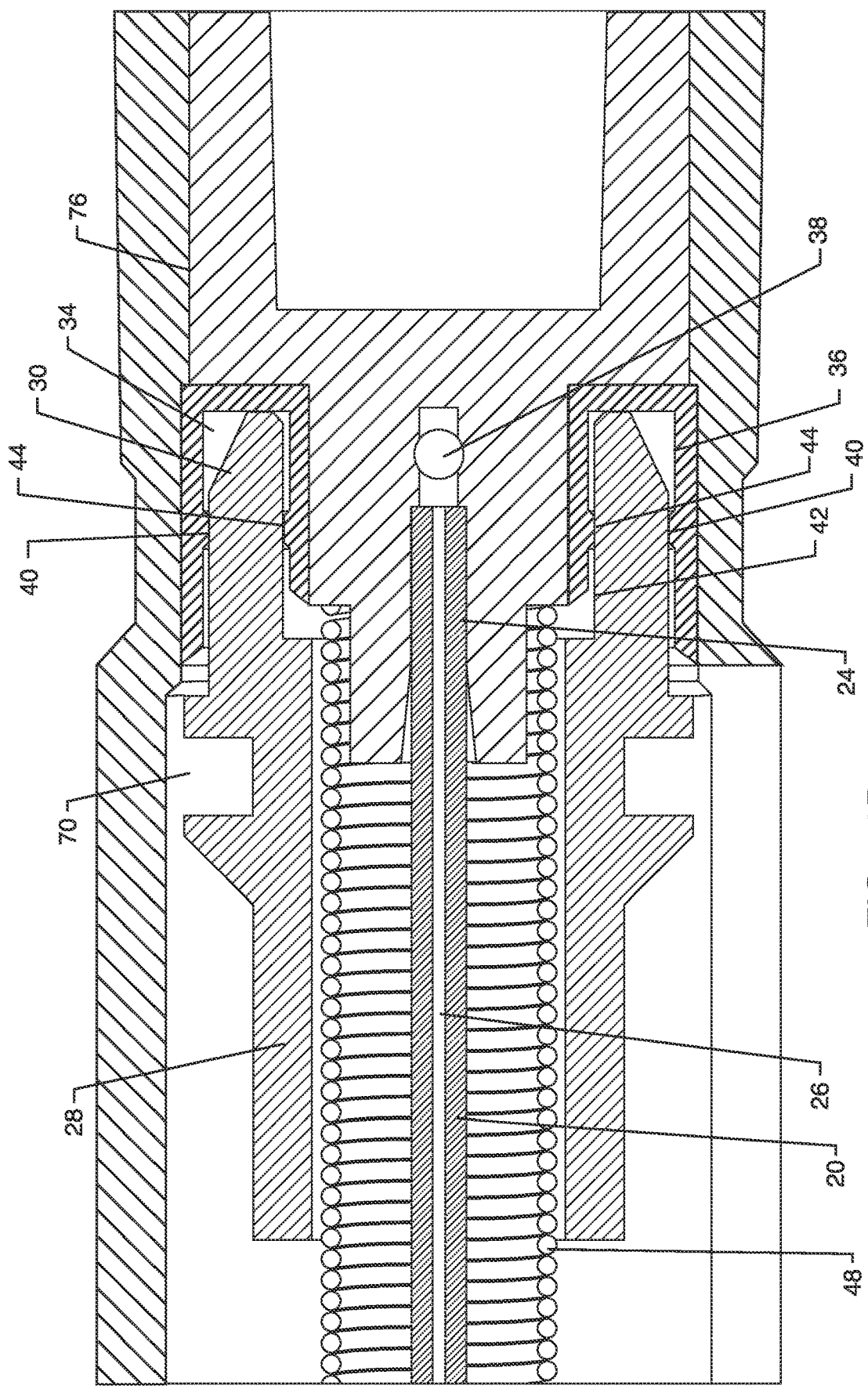
FIG. 18B is a view similar to 11B now showing the new seal design of the structure of FIG. 17A.

FIG. 18A is a view similar to 11A now showing another new embodiment of a seal design. FIG. 18B is a view similar to 11B now showing the new seal design of the structure of FIG. 17B. The end of the plunger 28 is relatively uniform without bumps but now a seal 40 and 44 are formed to engage the end of the plunger 28. The seals 40 and 44 are shown as a separate piece/part that is placed into the end of the needle base 76 and now forms the expandable chamber 34. The seals 40 and 44 may be formed as one part as shown herein or alternatively formed as two separate parts. Again, the seals 40 and 44 would be formed from a deformable and resilient material such as rubber or a seal-like material.

In another embodiment not shown, the plunger end 28 can be smooth and fit tightly into the end expandable chamber without a seal 40 and 44. A grease seal would be formed where a sealing substance such as a sealing paste or viscous fluid would be placed between the tight tolerance of the plunger end 28 and the expandable chamber. The viscosity of the sealing substance is great enough such that a formed (separately manufactured) seal 40 and 44 is not needed. Alternatively, a sealing substance could also be used in any of the earlier shown and discussed embodiments. As can be seen by those skilled in the art, a variety of sealing methods or structures could be used to form the expandable chamber 34.

Figure 19:
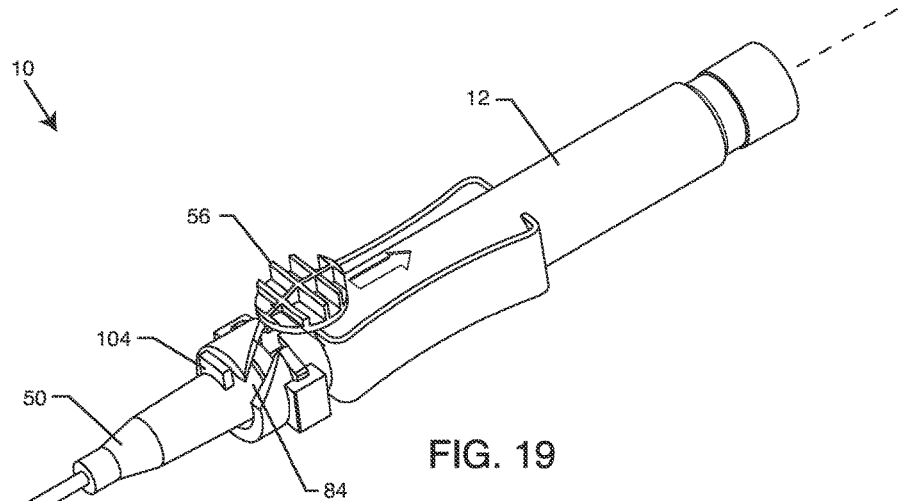
FIG. 19 is a perspective view of an exemplary catheter insertion device of the present invention now including a non-linear slot formed in the housing that rotates the catheter upon insertion.
Figure 22:
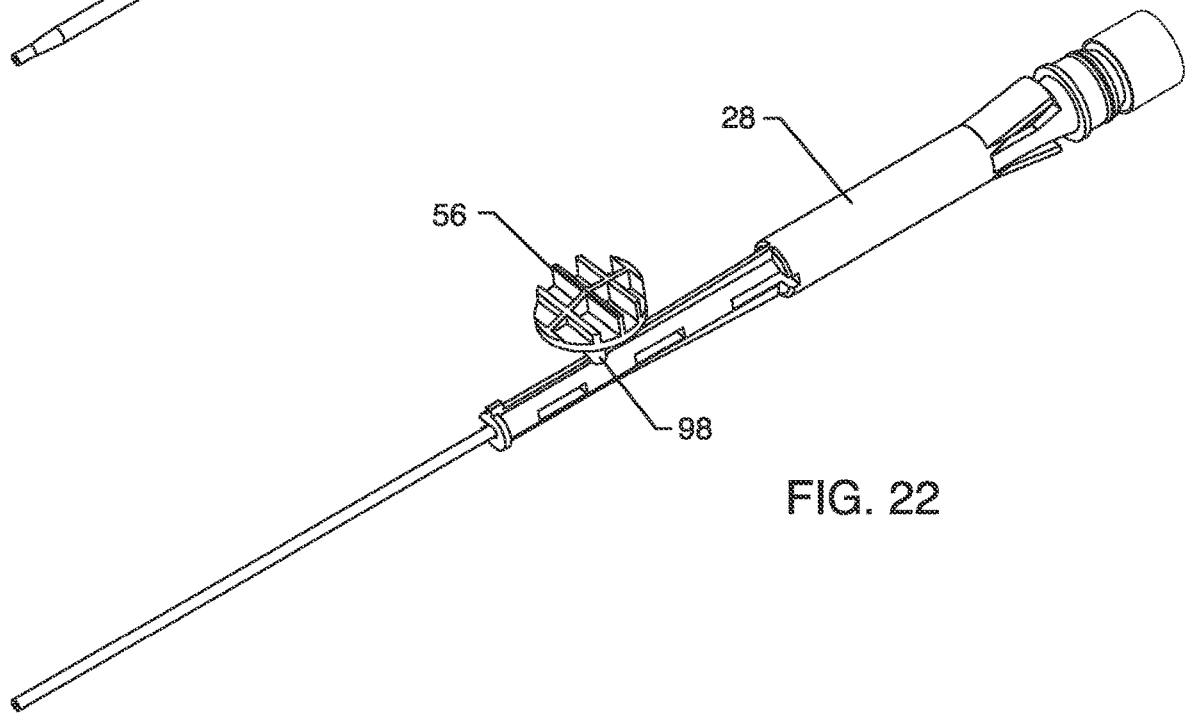
FIG. 22 is the same perspective of the structure of FIG. 21 now with the catheter removed.

Another exemplary embodiment of the present invention is shown in FIGS. 19 through 33. This embodiment is similar to the previous embodiments but now includes various features that allow the catheter 50 to rotate upon insertion. In FIG. 19 the hollow needle 20 can be defined as extending along a longitudinal axis 92. A plunger 28 is still slidably disposed over at least a portion of the hollow needle as shown in FIG. 22, where the distal skin-piercing end 22 of the hollow needle extends through a distal end 32 of the plunger. A spring 48 is still mechanically engaged between at least a portion of the proximal base end of the hollow needle and a portion of the plunger, the spring biasing the plunger towards the distal skin-piercing end of the hollow needle. The catheter 50 is slidably disposed over at least a second portion of the hollow needle where the distal skin-piercing end of the hollow needle extends through a distal insertion end of the catheter, the catheter comprising the distal insertion end opposite a proximal connection end, where a surface of the catheter contacts the distal end of the plunger during catheter insertion. An expandable chamber still has a first opening in fluidic or pneumatic communication with the channel of the hollow needle, the expandable chamber at least partially formed by the proximal base end of the hollow needle and a proximal end of the plunger, the expandable chamber configured to increase in volume as the plunger moves towards the distal skin-piercing end of the hollow needle.

Figure 25:
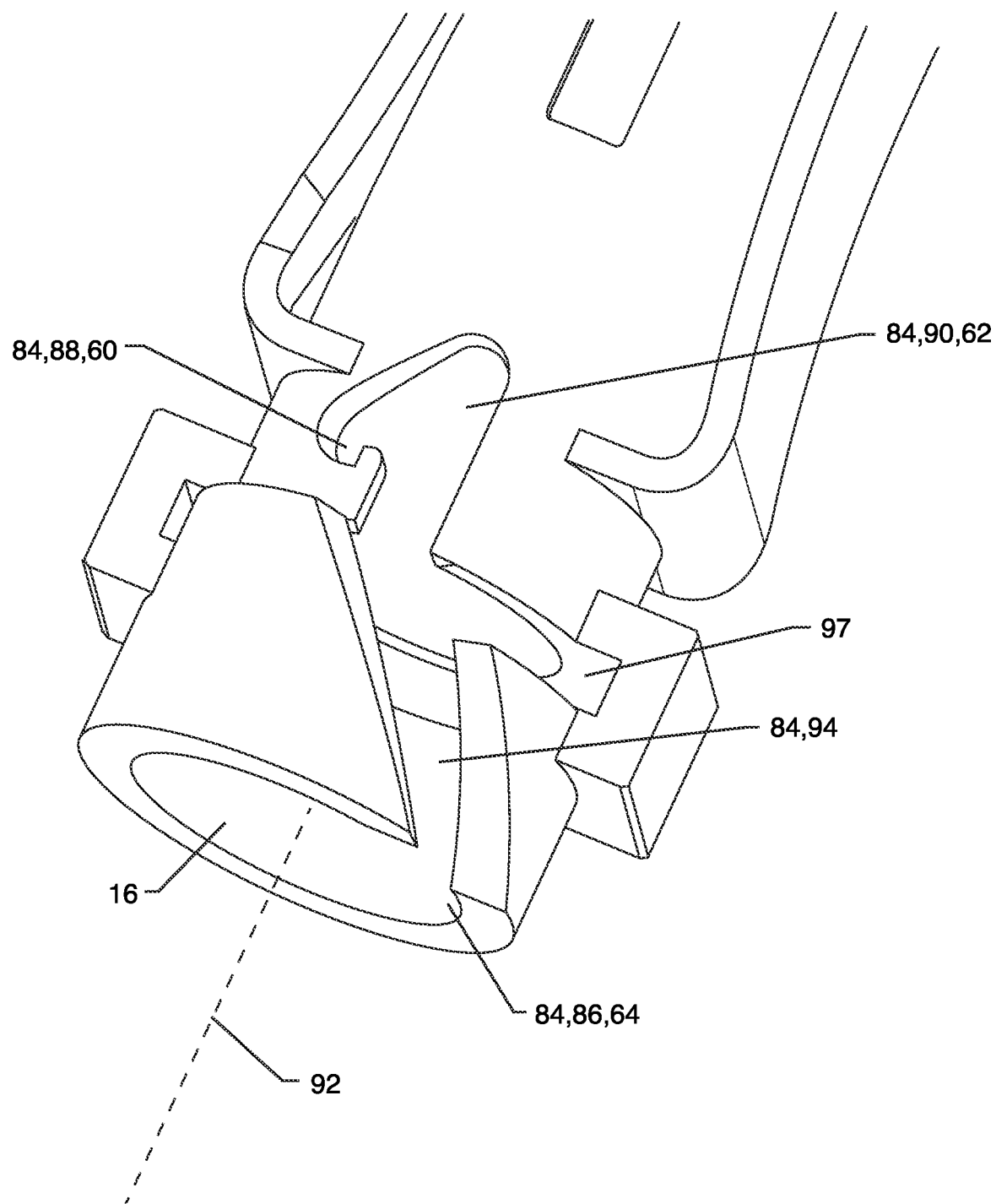
FIG. 25 is an enlarged perspective view of the novel slot formed in the housing.

A housing 12 is attached to the proximal base end of the hollow needle, the housing 12 having an open distal end 16 opposite the proximal base end of the hollow needle. The button 56 is still non-movably attached to the plunger and extends outside of the housing. The housing includes a new and novel slot 84 which can be best seen in FIG. 25. The new slot 84 extends from a slot open end 86 to a slot closed end 88 with a slot turn 90 there between. The slot open end 86 is located at the open distal end 16 of the housing 12. At least a portion of the slot 94 extending from the slot open end 86 to the slot turn 90 is non-linear with respect to the longitudinal axis 92 of the hollow needle. As can be seen in FIG. 25, the non-linear slot portion 94 is twisted or curved as one moves along the longitudinal axis 92. The slot turn 90 then changes direction of the slot 84 between the slot open end 86 and the slot closed end 88.

Figure 27:
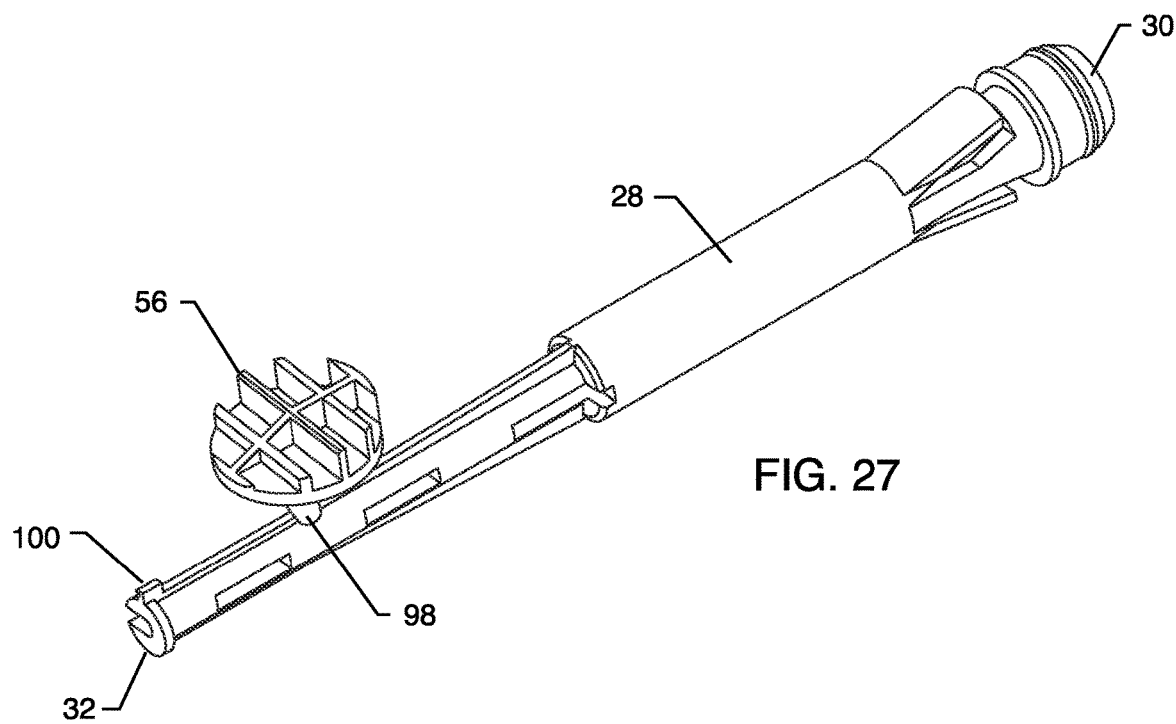
FIG. 27 is a perspective view of another embodiment of a plunger now with a rotation coupling feature.
Figure 28:
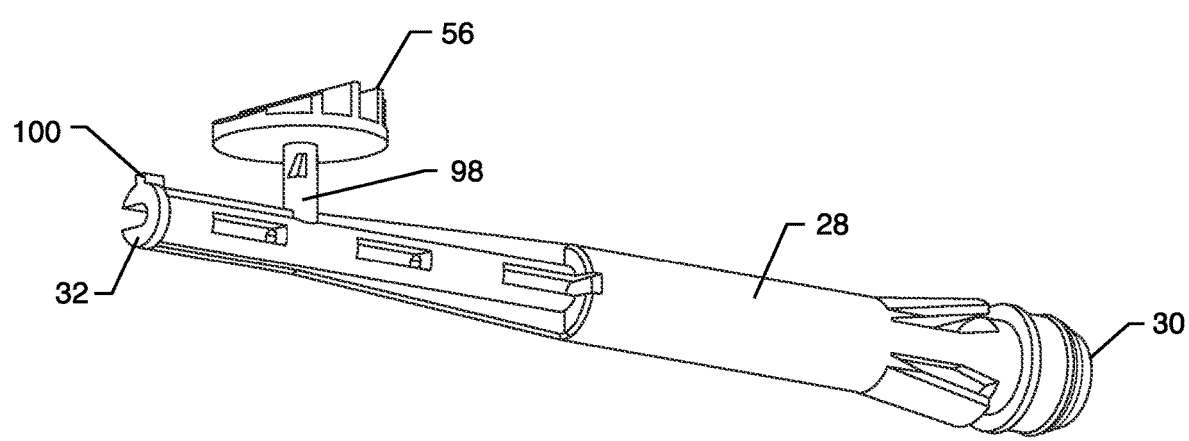
FIG. 28 is a bottom perspective view of the plunger depicted in FIG. 27.

As best seen in FIGS. 27 and 28, the plunger 28 moves with the button 56 and a portion of the button 98 is configured to be moveable within the slot 84 between the stored position 60, the armed position 62 and the extended position 64. The stored position 60 is when the portion of the button 98 is located at the slot closed end 88. The armed position 62 is when the portion of the button 98 is located at the slot turn 90. The extended position 64 is when the portion of the button 98 is located at and/or past the slot open end 86. The plunger 28 is configured to rotate about the longitudinal axis 92 of the needle as the portion of the button 98 passes through the non-linear portion 94 of the slot.

As best seen in FIGS. 27 and 28, the plunger 28 at the plunger distal end 32 may comprise a male (first) rotation coupling feature 100. This rotation coupling feature 100 can take on many shapes and forms and is herein represented as a tab or extension. Now turning to FIGS. 29 and 30, the catheter 50 at the proximal connection end 54 comprises a female (second) rotation coupling feature 102. Similarly, the rotation coupling feature 102 can take on many shapes and forms and is herein represented as a slot. Note, that it is understood by those skilled in the art that the male and female portions could be switched between the plunger and the catheter. The male 100 and female 102 rotation coupling features are configured to releasably and rotatably engage one another and move the catheter in unison with the plunger as the plunger rotates about the longitudinal axis of the needle as the portion of the button 98 passes through the non-linear portion 94 of the slot 84.

Figure 26A:
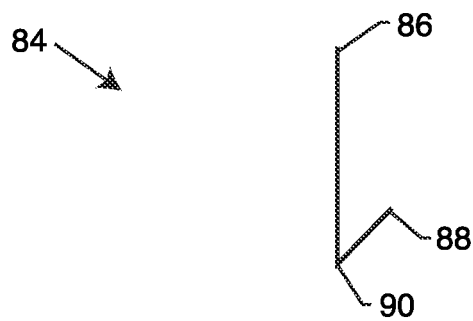
FIG. 26A is a simplified representation of one embodiment of a slot formed into the housing that corresponds to the embodiments shown in FIGS. 1-18.

The plunger and/or the catheter may include various means for rotatably coupling the plunger and the catheter in rotational unison as the plunger rotates as it moves from the armed position to the extended position. Many of these different means are shown in FIGS. 26. To begin with, FIGS. 26A through 26E are simplified representations of the slots 84. FIG. 26A is the previous slot shown in FIGS. 1-16. As one can see and understand the slot in FIG. 26A did not rotate the plunger or catheter as it was extending.

Figure 26B:
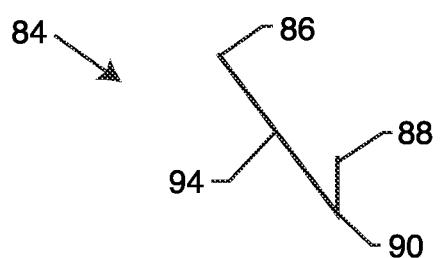
FIG. 26B is a simplified representation of one embodiment of the novel slot formed into the housing that corresponds to the embodiments shown in FIGS. 19-25.

FIG. 26B shows one embodiment of the path the slot 84 may take. In this embodiment the slot closed end 88 is straight whereas the non-linear portion of the slot 94 is angled. This angle creates the rotation when the plunger extends.

Figure 26C:
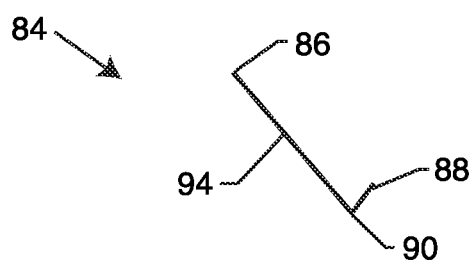
FIG. 26C is another embodiment of the novel slot.

FIG. 26C is another embodiment of the path the slot 84 may take. In this embodiment the slot is angled about both ends of the slot turn 90.

Figure 26D:
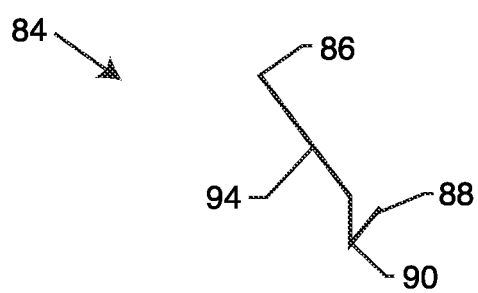
FIG. 26D is another embodiment of the novel slot.

FIG. 26D is yet another embodiment of the path the slot 84 may take. In this embodiment the non-linear portion 94 is not uniform and can make its own turn. This FIG. 26D most closely resembles the slot path 84 shown in FIG. 25.

Figure 26E:
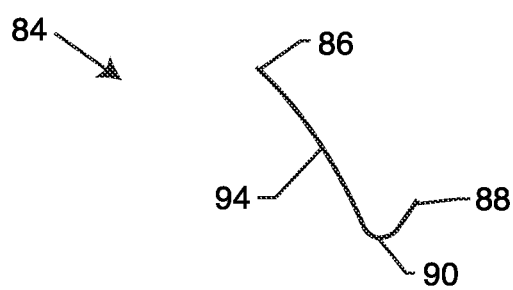
FIG. 26E is another embodiment of the novel slot.

FIG. 26E is yet another embodiment of the path the slot 84 may take. In this embodiment the path 84 is more smoothed and transitions in gradual increments, which is the opposite of how FIGS. 26A-D are more angled and abrupt. As can be seen my one skilled in the art, there are a multitude of different slot paths 84 that are possible, as this disclosure is not intended to limit it to just any one slot path design. However, the commonality between the new and novel embodiments shown in FIGS. 26B-26E are that the non-linear portion 94 creates a rotation of the plunger as the plunger extends outward. This in turn rotates and turns the catheter.

Figure 20:
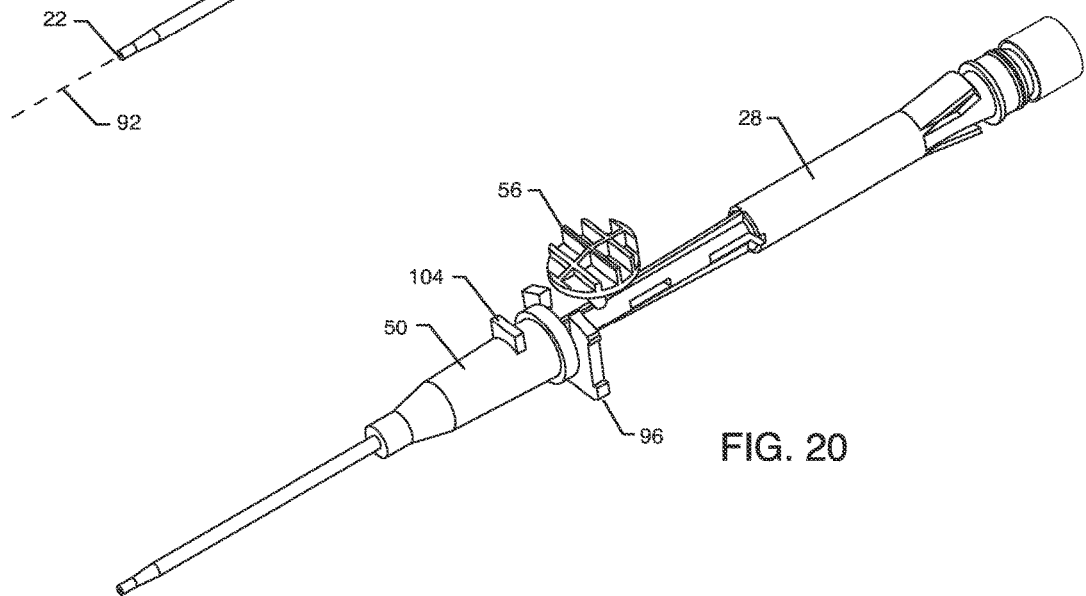
FIG. 20 is the same perspective of the structure of FIG. 19 now with the housing removed.
Figure 21:
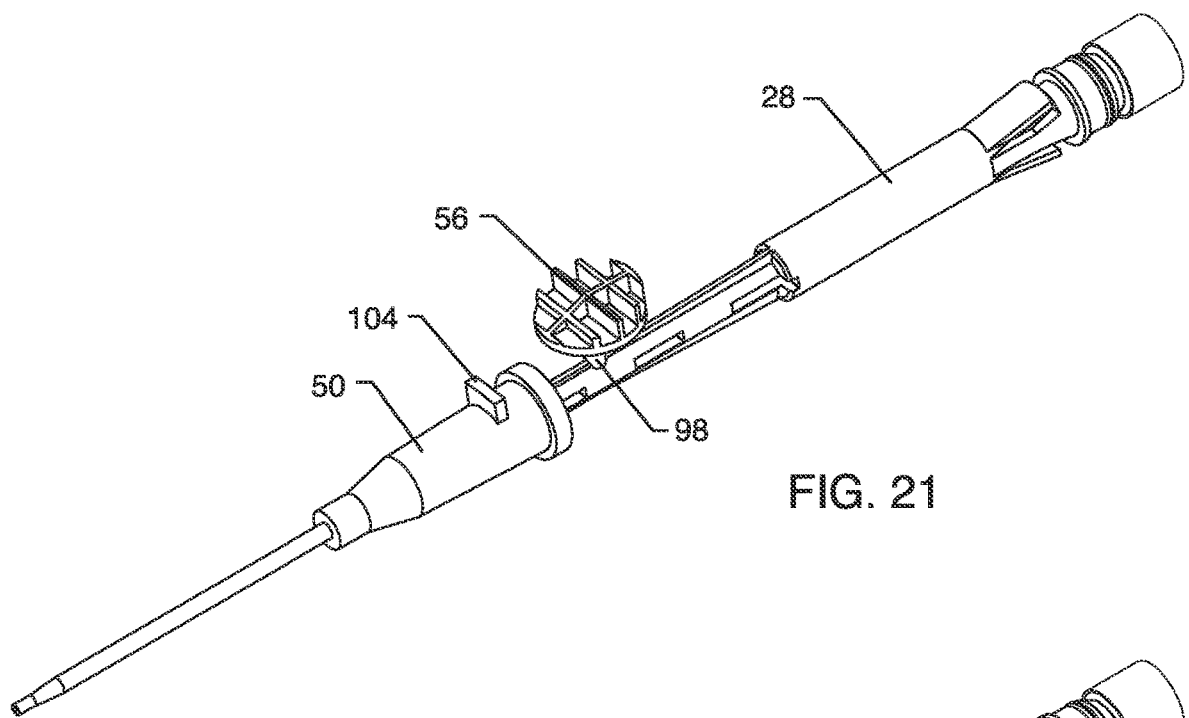
FIG. 21 is the same perspective of the structure of FIG. 20 now with the clip removed.
Figure 23:
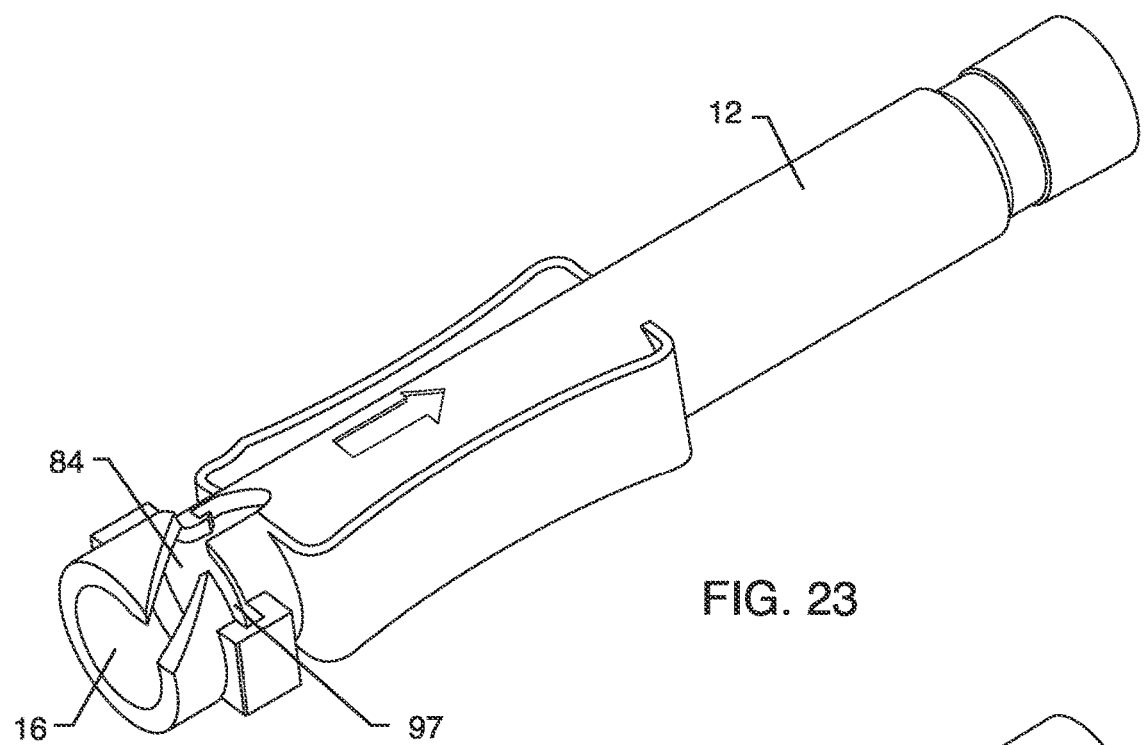
FIG. 23 is a perspective view of the housing depicted in FIG. 19.
Figure 24:
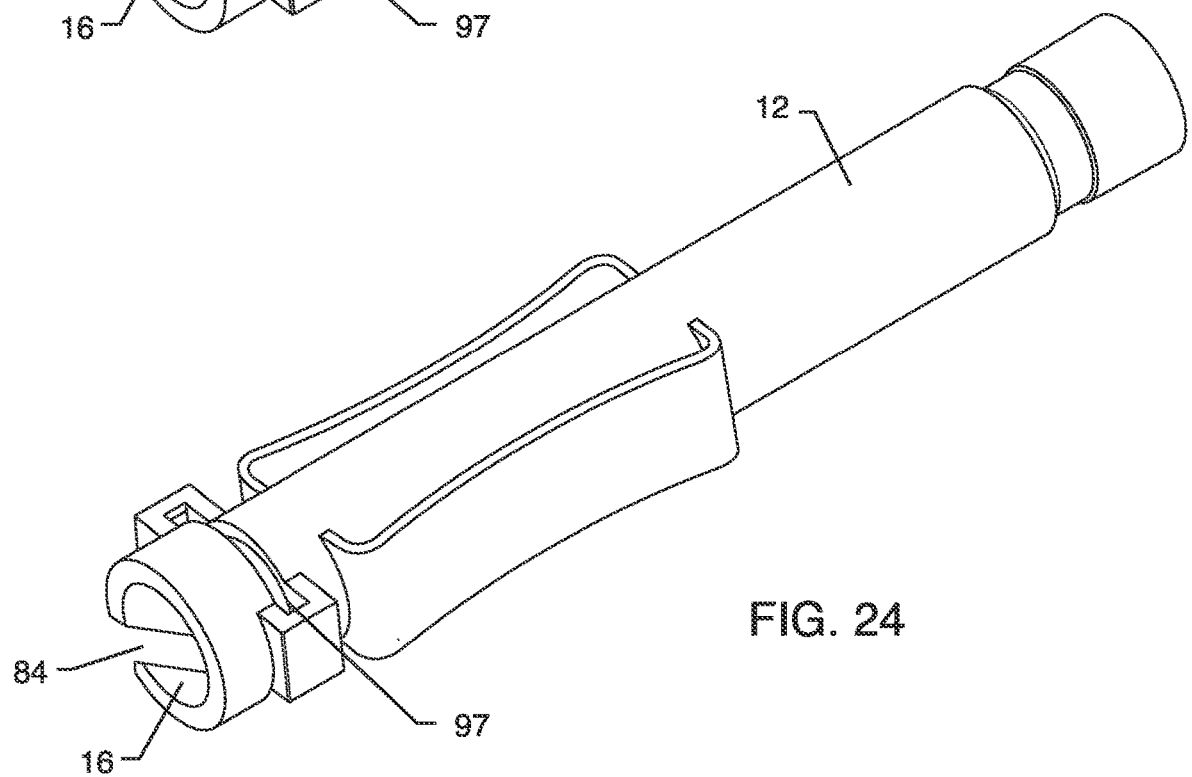
FIG. 24 is a bottom perspective view of the housing depicted in FIG. 23.

As best seen in FIGS. 19 and 20, when installing the plunger 28 into the housing, the clip 96 is removed. Removing the clip 96 allows the plunger 28 to be installed. Then, installing the clip 96 into the clip slot 97 prevents the plunger 28 from coming too far out and keeps the plunger captured at least partially within the housing 12. The clip slot 97 is best seen in FIGS. 23 and 24.

Figure 29:
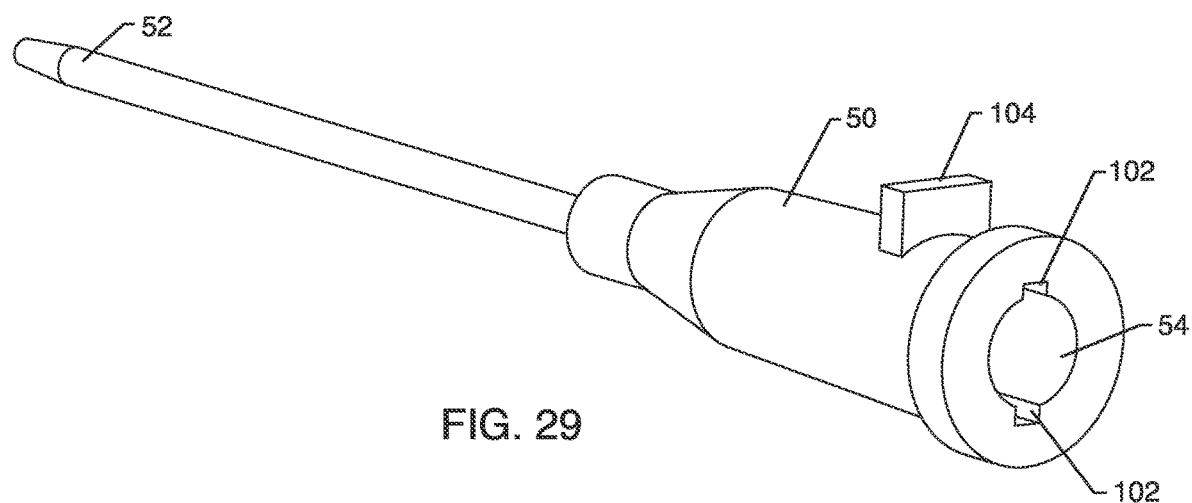
FIG. 29 is a perspective view of another embodiment of a catheter now with a rotation coupling feature.
Figure 30:
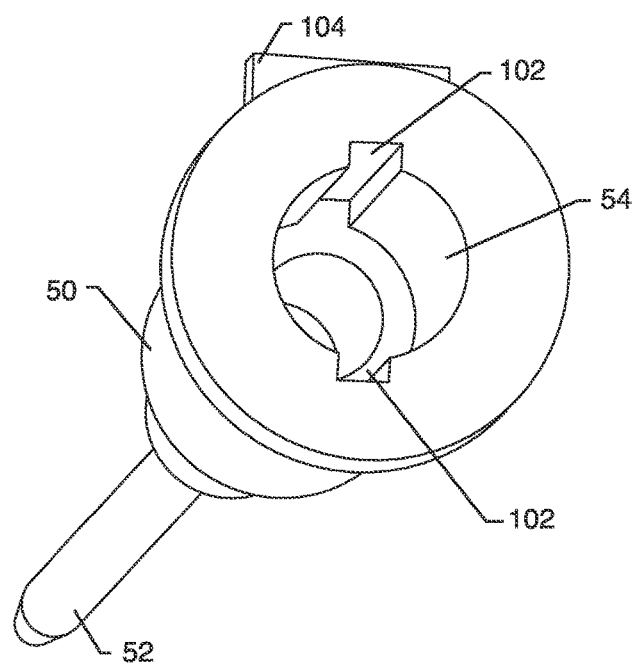
FIG. 30 is a rear perspective view of the catheter depicted in FIG. 29.
Figure 31:
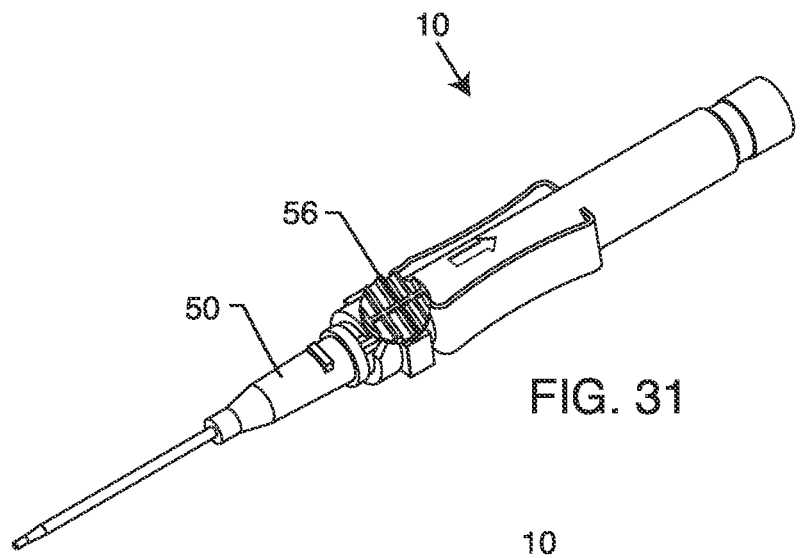
FIG. 31 is a perspective view of the catheter insertion device of FIGS. 19-30 now showing the beginning of the catheter insertion.
Figure 32:
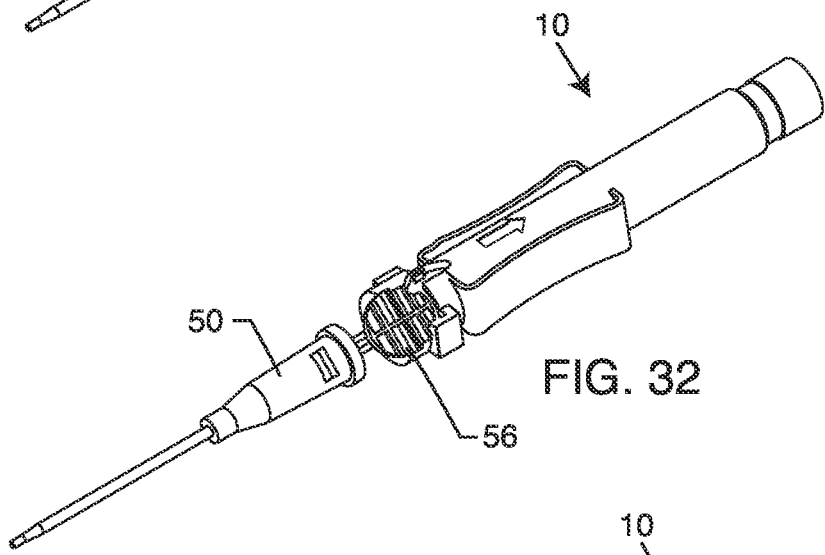
FIG. 32 is the same view as FIG. 31, now showing the catheter advancing and starting to rotate.
Figure 33:
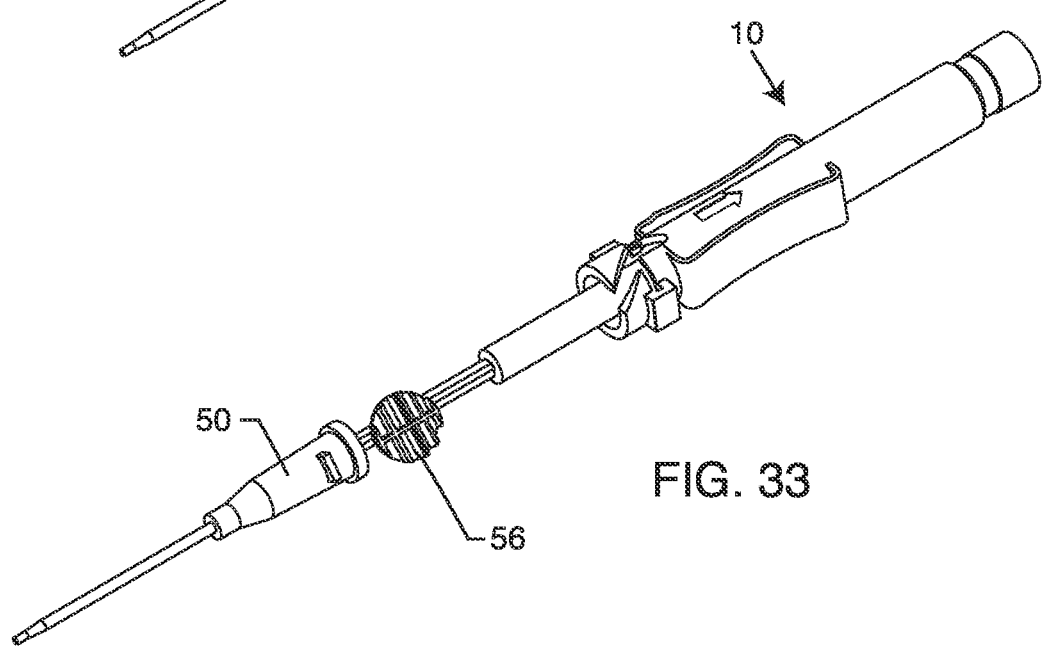
FIG. 33 is the same view as FIGS. 31 and 32, now showing the catheter advancing further and rotating a further amount

In FIGS. 29 and 30 one can see the tab 104 formed on the catheter 50. Then in FIGS. 31 to 33, one can see the rotation of the tab 104 such that it is easy to identify that the catheter 50 has rotated. Without such tab 104 it would be hard to visually identify whether the catheter 50 rotated or did not rotate.

Previously in this specification it was taught that when the seals are placed between two surfaces for a long period of time they would tend to stick and hold their mating surfaces together. Accordingly, in previous embodiments it was taught that the seals in the stored state should not be in contact with both mating surfaces and rather the user would arm the device by pulling backwards on the button to engage the seals just before use. However, the inventors have further improved on the previous designs such that now the seals can be stored in a state where they are contacting both mating surfaces. Accordingly, an exemplary embodiment of a catheter insertion device (10) is best seen in FIGS. 34-60. Many of the structures and numerals of this new embodiment are carried over from the previous embodiments taught herein, so the inventor will not repeat every detail again for the sake of brevity.

Referring again to FIGS. 34-60, a hollow needle 20 has a distal skin-piercing end 22 opposite a proximal needle end 24. The hollow needle defines a channel 26 in fluidic and/or pneumatic communication between the distal skin-piercing end and the proximal needle end. When the needle enters under the skin, various bodily fluids, body tissue or gas can enter the needle, thus is more accurate as claimed to describe this as fluidic and/or pneumatic communication. However, it is mostly blood that enters the needle once it pierces a vein or artery. As taught previously, the skin and other body tissue can be considered to be impermeable, such that a vacuum formed inside the present invention is maintained until the needle punctures a vein or artery.

A proximal needle end is attached to a needle base 76. A plunger 28 is slidably disposed over at least a portion of the hollow needle, wherein the distal skin-piercing end of the hollow needle extends through a plunger distal end 32. The plunger has a plunger proximal end 30 opposite the plunger distal end. A compression spring 48 is disposed concentric with and over at least a second portion of the hollow needle. The compression spring mechanically engages directly and/or indirectly between at least a portion of the needle base and a portion of the plunger. The compression spring biases (pushes/forces) the plunger away from the needle base.

A catheter 50 is slidably disposed over at least a third portion of the hollow needle, wherein the distal skin-piercing end of the hollow needle extends through a distal insertion end 52 of the catheter. As previously taught, the distal insertion end of the catheter is flexible and can comfortably remain inserted into the patient after the needle is removed. Accordingly, the catheter includes the distal insertion end opposite a proximal connection end 54, where this proximal connection end can then be attached to various intravenous solutions or medications as needed. A catheter surface 68 is configured to be contactable by the plunger distal end when the plunger moves in a forward direction.

To help define the present invention and as taught previously, a longitudinal axis 92 may be defined as extending along the hollow needle, the needle base, the plunger, the compression spring and the catheter. In this new embodiment, the plunger is configured to move between a stored position, an armed position and an extended position. The plunger now just rotates about the longitudinal axis between the stored position and armed position, and the plunger now just translates along the longitudinal axis between the armed position and the extended position. As will be explained later, this new and novel motion overcomes the tendency of the seals to stick to their mating surfaces.

An expandable chamber 34 is in fluidic and/or pneumatic communication with the channel of the hollow needle by an aperture 38 in the needle base. The expandable chamber is configured to increase in volume as the plunger moves towards the distal skin-piercing end of the hollow needle. The expandable chamber is at least partially delimited by the needle base and the plunger proximal end 30.

Figure 39:
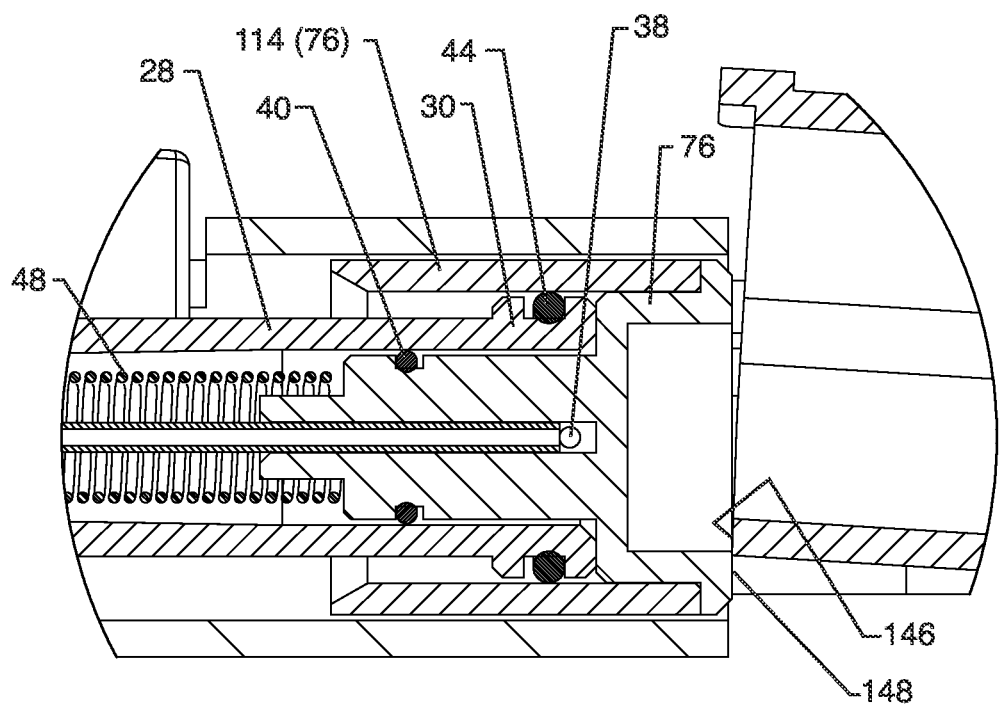
FIG. 39 is an enlarged sectional view taken along lines 39-39 of FIG. 37.
Figure 40:
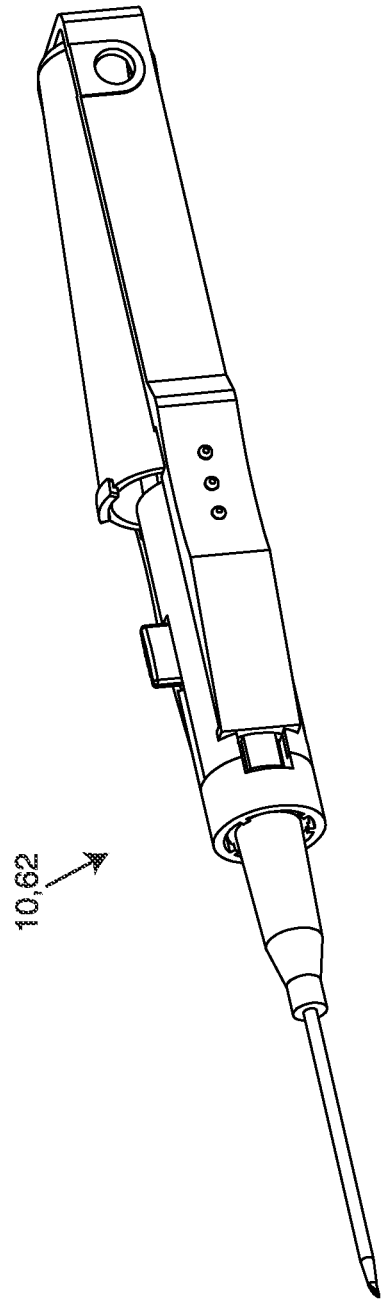
FIG. 40 is a perspective view similar to FIG. 34 now showing the button and plunger in the armed position.
Figure 41:
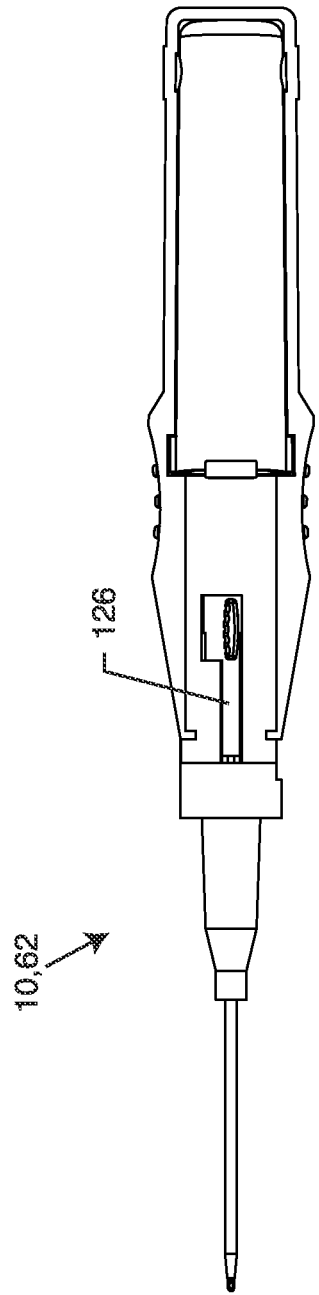
FIG. 41 is a top view of the structure of FIG. 40.

Referring more specifically to FIG. 39, one can see that the vacuum chamber 34 has essentially a zero volume (very little volume) but now a housing sleeve 114 is used. As previous taught, the expandable chamber has a substantially zero volume when the plunger is in the stored and/or armed position such that a vacuum can be formed. As the plunger moves forward, the vacuum chamber is formed by the surfaces of the plunger that are between the needle base and the housing sleeve. A first circumferential seal 40 of the expandable chamber is disposed between the needle base and the plunger, where the first circumferential seal is configured to seal the needle base to the plunger for a distance when the plunger moves away from the needle base. Likewise, a second circumferential seal 44 of the expandable chamber is disposed between the plunger and either of the main housing 116 or a housing sleeve 114. The second circumferential seal is configured to seal the housing or the housing sleeve to the plunger for the distance when the plunger moves away from the needle base.

When looking at FIG. 39, it is understood that the housing sleeve is a separately manufactured part that is then attached to the needle base. The housing sleeve can be bonded, glued, snap fit, interference fit or otherwise attached to the needle base. However, it will also be understood that the housing sleeve can be formed as part of the needle base itself into a single component. Additionally, the housing sleeve could be eliminated and the second seal could seal between the plunger and the main housing 116.

In the embodiments shown herein, the needle base, the plunger and the compression spring are at least partially disposed within the main housing 116 in the stored position. Now, the main housing may include a front housing 110 and a rear housing 112. As shown herein, the front housing is fixedly attached to a front portion 122 of the main housing. The rear housing is pivotably attached to a rear portion 124 of the main housing. The front housing may be a separately manufactured part in relation to the main housing and the rear housing may be a separately manufactured part in relation to the main housing. Alternatively, the front housing and rear housing may be formed integrally as part of the main housing, but this overly complicates the molding process. Therefore, as shown in this embodiment the front and rear housings are separately manufactured parts.

Figure 50:
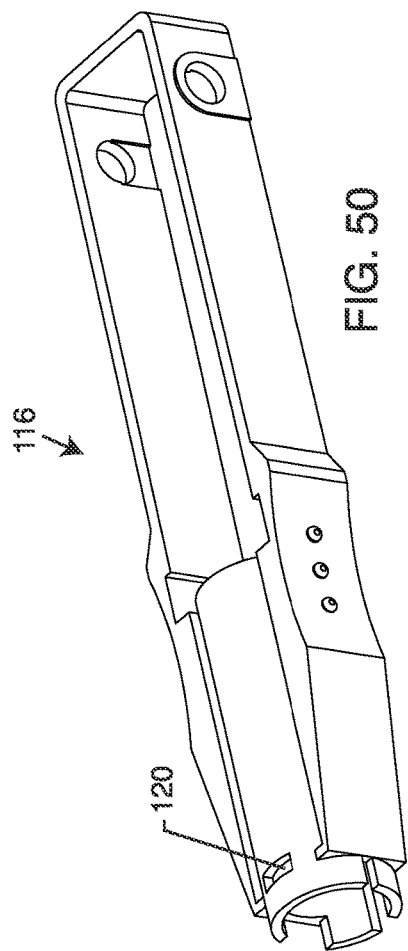
FIG. 50 is a perspective view of just the main housing.
Figure 51:
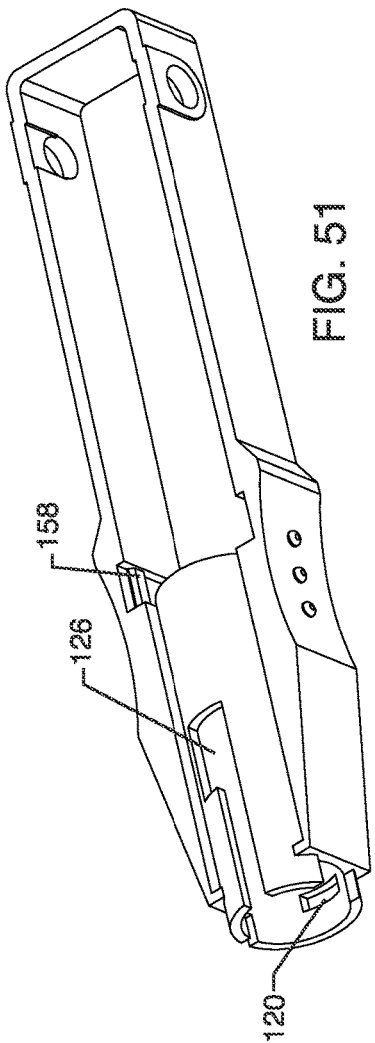
FIG. 51 is another perspective view of the main housing showing the opposite side in relation to FIG. 50.
Figure 53:
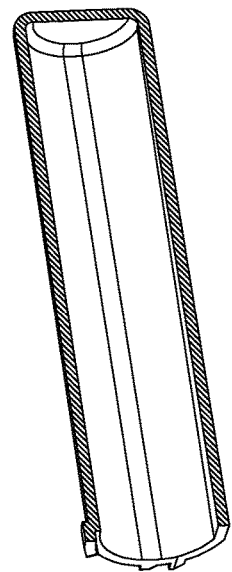
FIG. 53 is a sectional perspective view of the structure of FIG. 52 taken along lines 53-53.

To simplify assembly, the front housing is attached to the main housing by the use of a flexural snap feature 118 formed in the front housing, which is best seen in FIG. 57, that locks to a recess feature 120 formed in the main housing, that is best seen in FIG. 50. The flexural snap feature 118 takes advantage of the elasticity of the plastic material the front housing is made from. The flexural snap feature 118 has three of its sides removed such that it can flex about its attachment point. This allows the snap edge to flex out of the way and then lock into the recess feature 120 of the main housing. It will be understood by those skilled in the art that a wide variety of flexural snap features could be devised as this teaching is not intended to limit it just to the embodiment shown and taught herein. Furthermore, the recess feature and flexural snap feature could be swapped such that recess feature is formed as part of the front housing and likewise the flexural snap feature is formed as part of the main housing. It is also noted herein that all of the parts taught herein, excluding the needle itself (made from metal), are made from polymers (plastics) that have some amount of flex and give, such that flexural snaps and similar features may be utilized.

Figure 34:
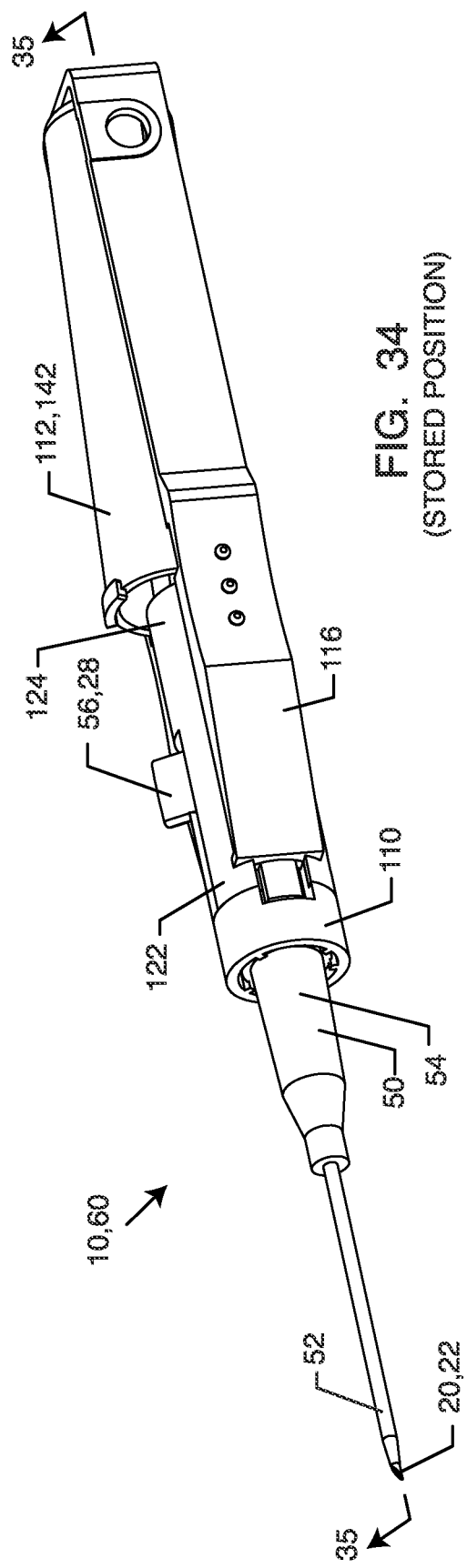
FIG. 34 is a perspective view of an exemplary catheter insertion device of the present invention in the stored position now including a L-shaped slot formed in the housing that allows the plunger to rotate to remove stiction between the seals and their mating surfaces.
Figure 35:
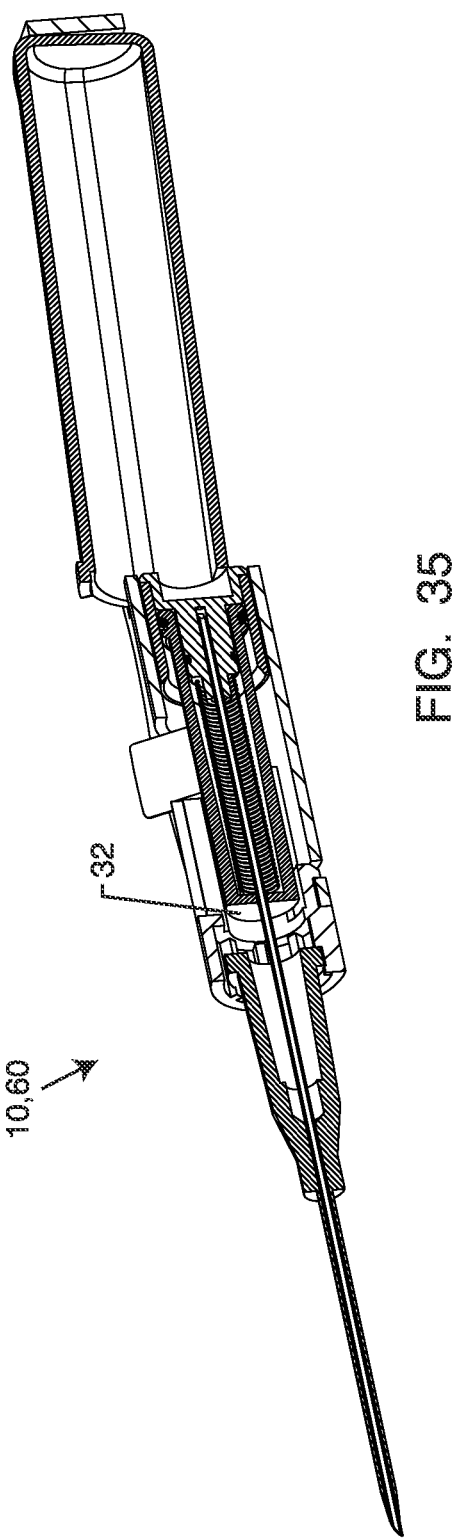
FIG. 35 is a sectional perspective view of the structure of FIG. 34 taken along lines 35-35.
Figure 36:
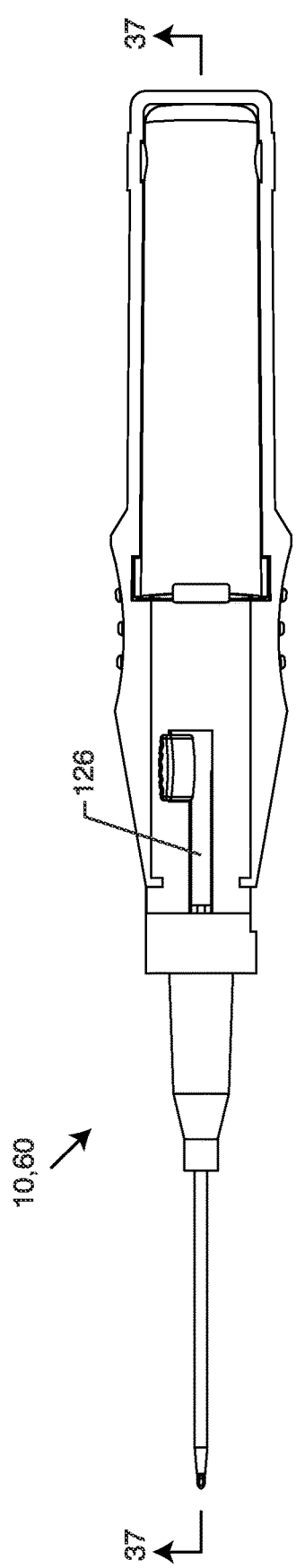
FIG. 36 is a top view of the structure of FIG. 34.
Figure 37:
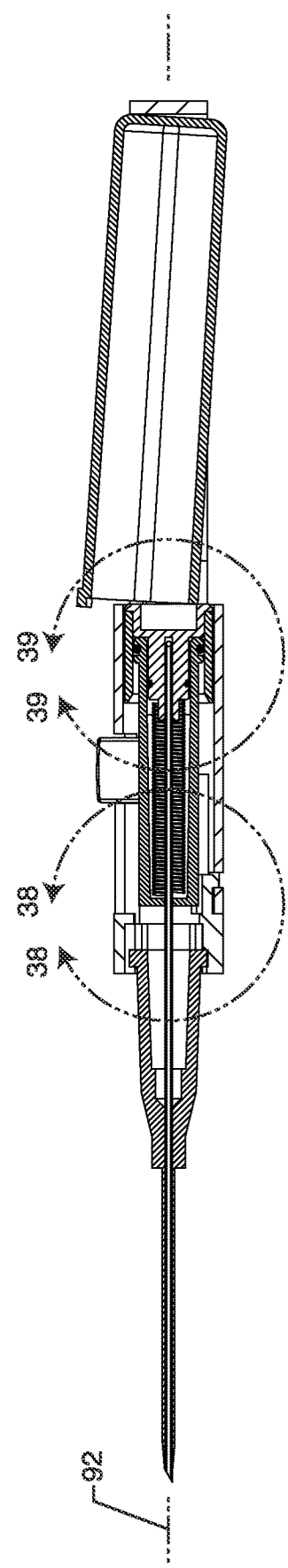
FIG. 37 is a sectional side view taken along the lines 37-37 of FIG. 36.

As shown in FIG. 34, in the stored position the catheter is temporarily captured at the proximal connection end by the front housing with an interference fit. When the plunger advances it then pushes the catheter outwardly from the interference fit and into the patient's vein or artery.

The plunger best shown in FIGS. 54-55 has a button 56 that is non-movably attached to the plunger and extends outwardly beyond the housing as shown in FIG. 34. As taught previously, the button is configured to be manipulated by the user. However, the motion of the button is now different with respect to the previously taught embodiments. This is because the main housing and/or front housing includes an L-shaped slot 126, wherein the button of the plunger extends through and is movable within the L-shaped slot between the stored position, the armed position and the extended position. One is also directed to FIG. 60 that has a simplified representation of the L-shaped slot 126. In the stored position (FIGS. 34-39) the button is located at a distal lower end 128 of the L-shaped slot. In the armed position (FIGS. 40-41) the button is located at a corner 130 of the L-shaped slot. In the extended position (FIGS. 42-49) the button is located at a distal upper end 132 of the L-shaped slot.

The button moves within the L-shaped slot between the distal lower end and the corner as it rotates about the longitudinal axis moving between the stored position and the armed position. The seals overtime may become sticky and have partially attached to their mating surfaces. By having the user rotate the plunger from the stored to armed position, this stickiness is now overcome. Now the present invention can function appropriately without the need to pull the backwards by the user. This also results in a simplified motion for the user. After the distal skin-piercing end of the needle is punctures under the skin the user simply rotates the button and can start advancing the needle. Once the needle punctures a vein or artery, the button moves within the L-shaped slot between the corner and the distal upper end as it translates along the longitudinal axis moving between the armed position and the extended position. The plunger translates along the longitudinal axis when a vacuum formed in the expandable chamber by the compression spring pushing the plunger away from the needle base is released by a fluid and/or a gas entering the channel of the hollow needle at the distal skin-piercing end.

Figure 38:
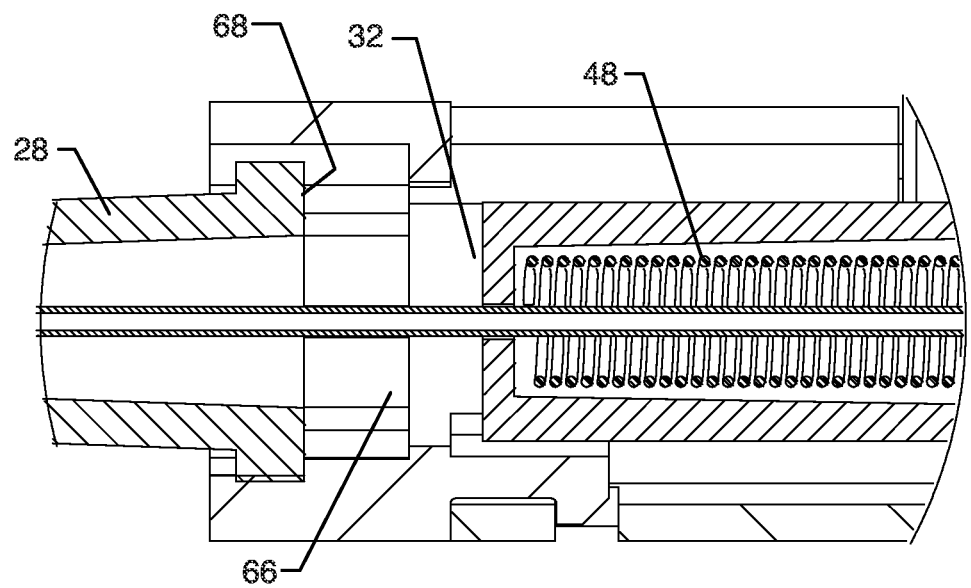
FIG. 38 is an enlarged sectional view taken along lines 38-38 of FIG. 37.

It is also noted herein, when referring to FIG. 38, in the stored position a gap 66 may exists between the proximal connection end of the catheter and the plunger distal end. This gap allows the plunger to start to move forward a set distance to establish the vacuum in the vacuum chamber and also to gain momentum once a vein or artery is reached. Then, when the plunger comes into contact with the catheter, the momentum of the plunger helps to overcome the interference fit of the catheter to the front and/or main housing.

Figure 49:
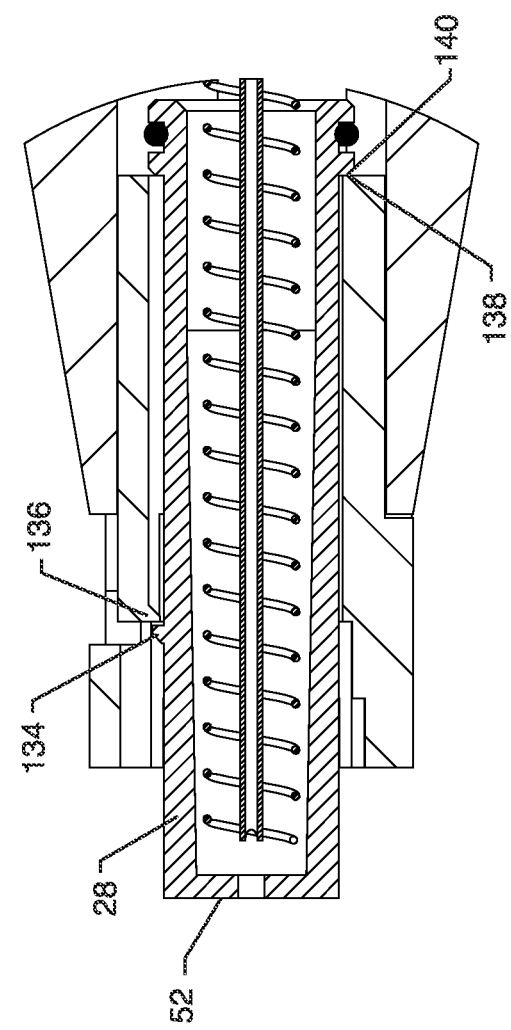
FIG. 49 is an enlarged sectional view of the structure of FIG. 48 taken along lines 49-49.

Referring again to FIG. 54, the plunger may include an outwardly extending tab 134 configured to be captured by a flexural lock feature 136 seen in FIG. 49 formed in the front housing when the plunger is in the extended position thereby preventing the plunger moving backwards into the armed position after it has moved forward into the extended position. As is understood by those skilled in the art, many variations of the tab 134 and lock 136 may be devised, as this teaching is not intended to be limited to the specific embodiment taught herein. Furthermore, the tab and lock may be reversed to reside on the opposite part as previously discussed.

As best seen in FIG. 49, in the extended position a portion 138 of the plunger may contact a portion 140 of the front housing and/or main housing thereby preventing the plunger from moving furthermore forwards beyond the front portion of the main housing. Once in the extended position, the plunger is prevented from moving forwards by the portions 138 and 140 and prevented from moving backwards by the tab 134 and lock 136.

Figure 44:
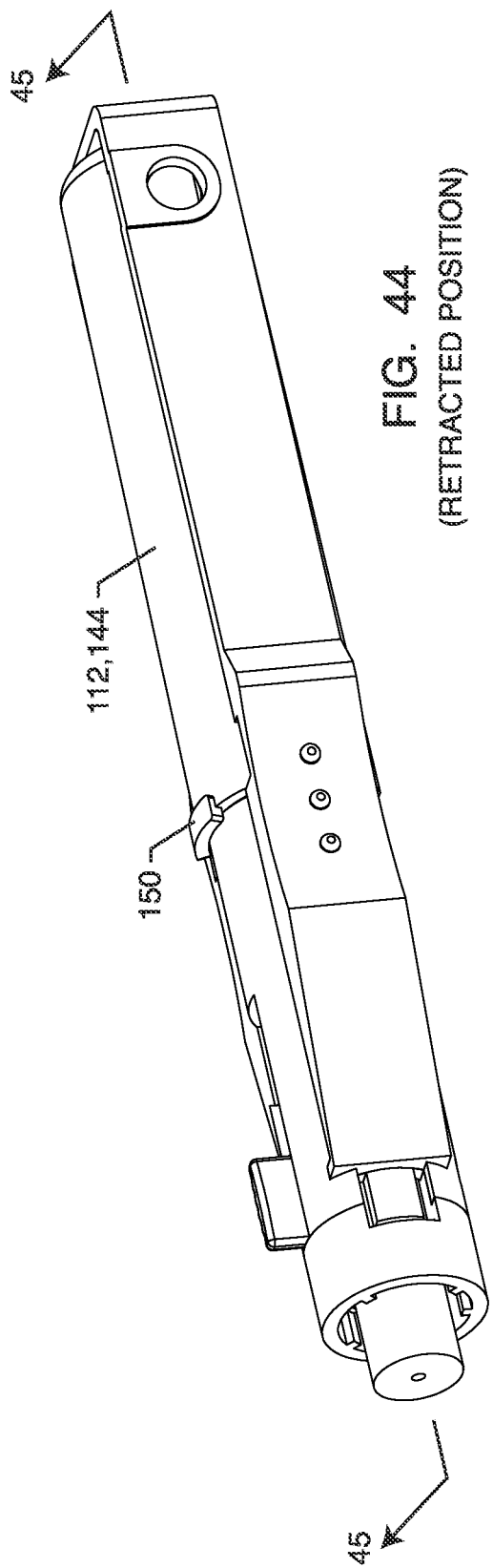
FIG. 44 is a perspective view similar to FIG. 34 now showing the needle retracted position where the needle is retracted into the rear housing by aligning the rear housing with the main housing.
Figure 45:
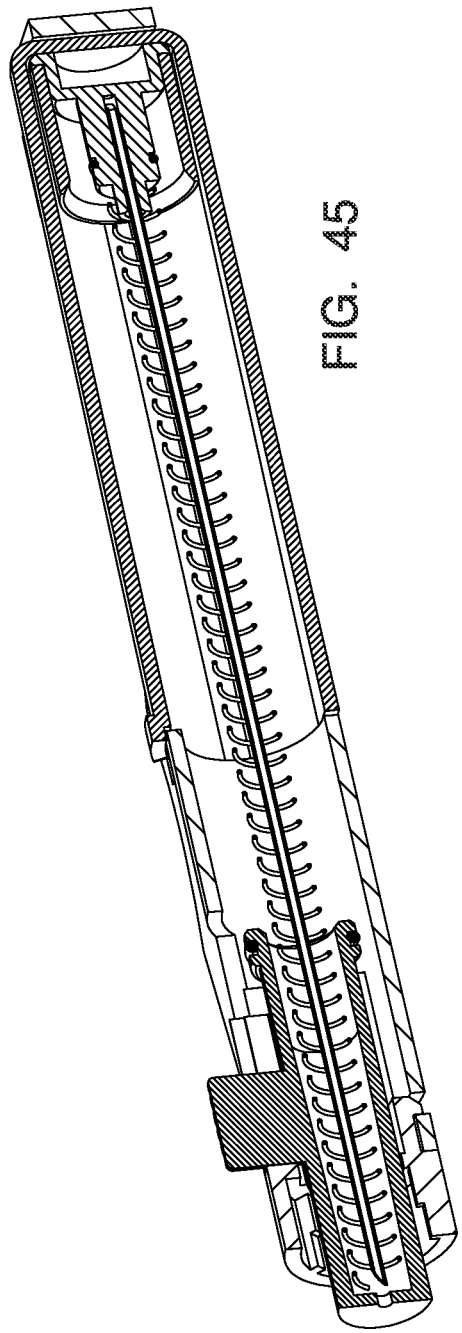
FIG. 45 is a sectional perspective view of the structure of FIG. 44 taken along lines 45-45.
Figure 46:
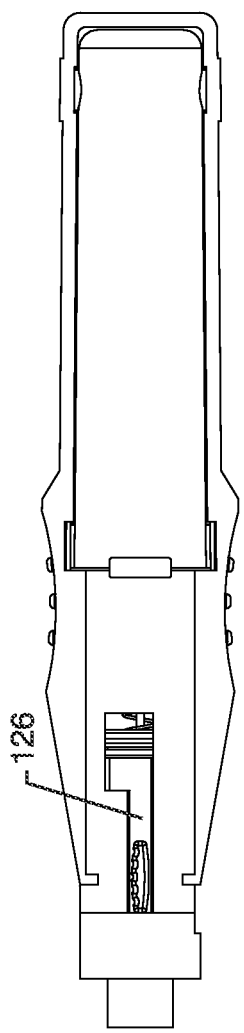
FIG. 46 is a top view of the structure of FIG. 44.
Figure 47:
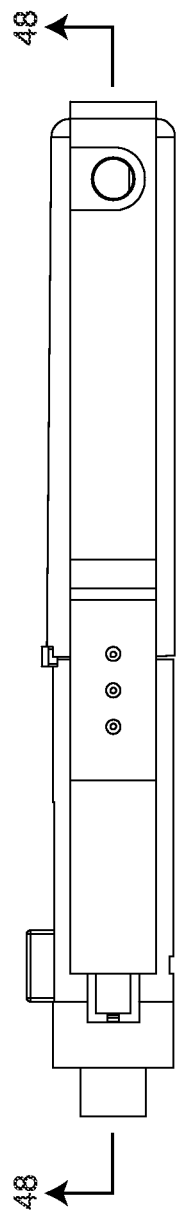
FIG. 47 is a side view of the structure of FIG. 46.
Figure 48:
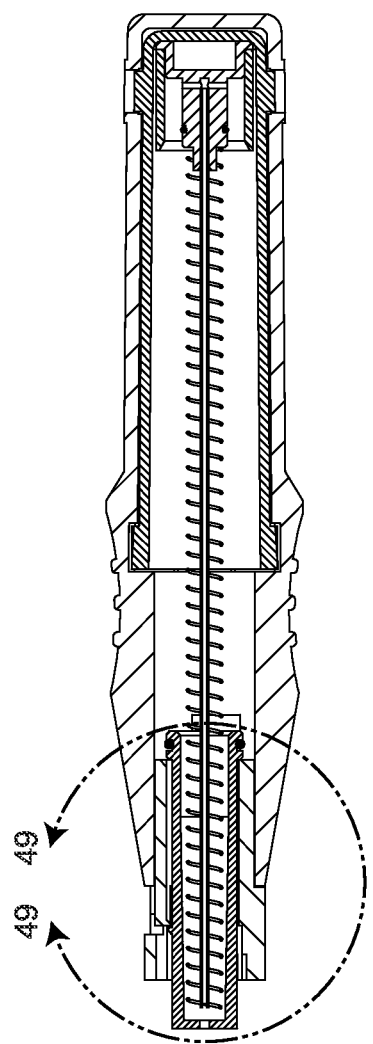
FIG. 48 is a sectional view of the structure of FIG. 47 taken along lines 48-48.

Referring now to FIGS. 42-45, the rear housing 142 may be movable from a needle start position 142 (FIGS. 42-43) to a needle retracted position 144 (FIGS. 44-45). As best shown in FIGS. 42-43 and even in FIG. 39 in the needle start position a portion 146 of the rear housing abuts a portion 148 of the needle base preventing the compression spring from moving the needle base backwards towards and inside the rear housing. As best shown in FIGS. 44-45, in the needle retracted position the rear housing has pivoted down until the stop 150 hits the main housing, and now the portion of the rear housing no longer abuts the portion of the needle base and the needle base and hollow needle are moved by the compression spring backwards into the rear housing wherein the distal skin-piercing end of the hollow needle is retracted within the plunger and/or front housing, thereby preventing the distal skin-piercing end of the hollow needle from inadvertent punctures.

Figure 52:
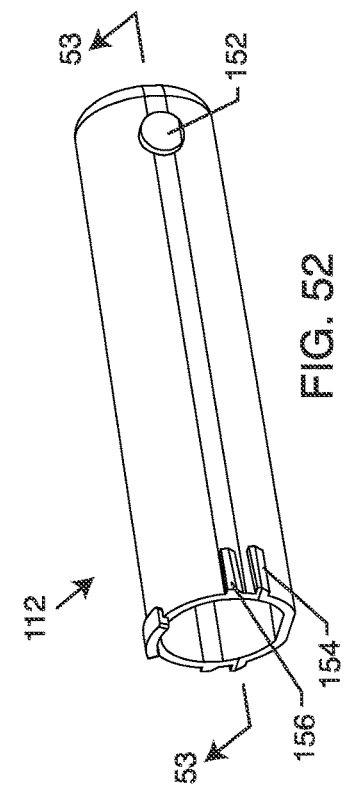
FIG. 52 is a perspective view of just the rear housing.

As shown herein, the rear housing 112 is configured to rotate about the pivot 152 that is captured within the main housing. As best seen in FIG. 52, a first stop 154 on the rear housing is designed to abut a ridge 158 formed in the main housing. The ridge 158 keeps the rear housing pivoted up while in stored for transport such that the rear housing stays in the needle start position. Then, after the catheter has been inserted and the needle should be retracted, the user will apply enough force to overcome the ridge by the first stop such that the ridge then falls between the first stop and a second stop 156. Now the ridge of the rear housing is secured in place and is unlikely to pivot back out. The stop 150 also prevents the rear housing from pivoting further. At this point the needle is retracted and the present invention will not inadvertently puncture someone.

It is noted herein that the same compression spring that moved the plunger forward is also utilized to move the needle and the needle base backwards. However, it is understood that two different compression springs could have been used to accomplish the same functionality.

It is also noted herein, that the rear housing pivots, but could have been designed to translate, rotate or move in a different manner such that the needle base would be held for catheter insertion and then released backwards into the rear housing after catheter insertion.

Furthermore, it will also be understood by those skilled in the art that an additional button could have been used movably attached to the main housing now with a nonmovable rear housing, such that once the additional button was pressed, it allowed the needle base to move backwards.

Furthermore again, one skilled in the art will also understand that the first button 56 attached to the plunger in the stored position, could be devised to prevent the rear housing from pivoting downward (or moving) to release the needle base backwards. This embodiment (not shown) would prevent the rear housing from being pivoted before the present invention was used to insert a catheter.

Figure 61:
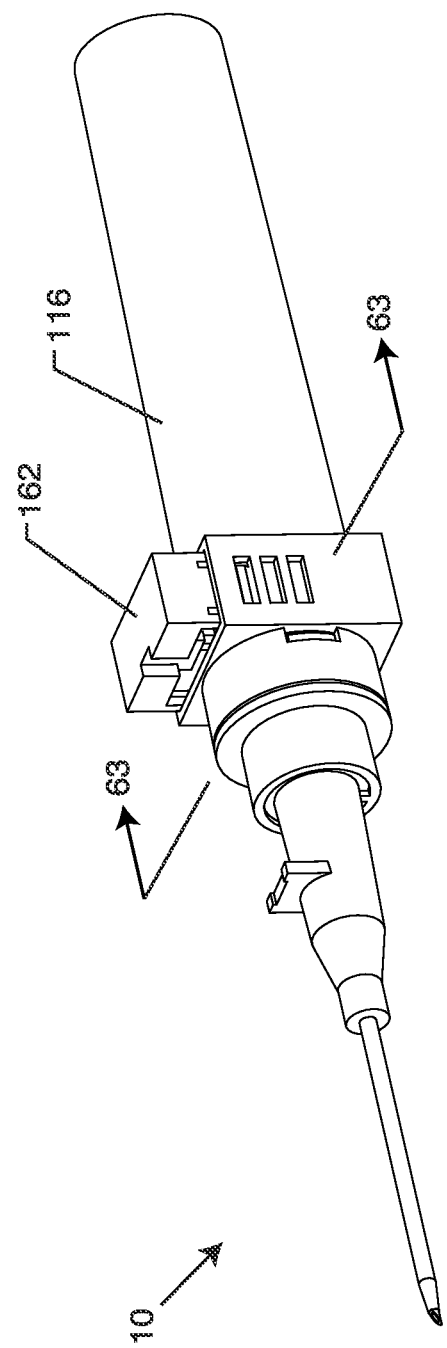
FIG. 61 is a perspective view of an exemplary catheter insertion device of the present invention in the stored position now including depressable button that control the plunger extension and needle retraction.
Figure 62:
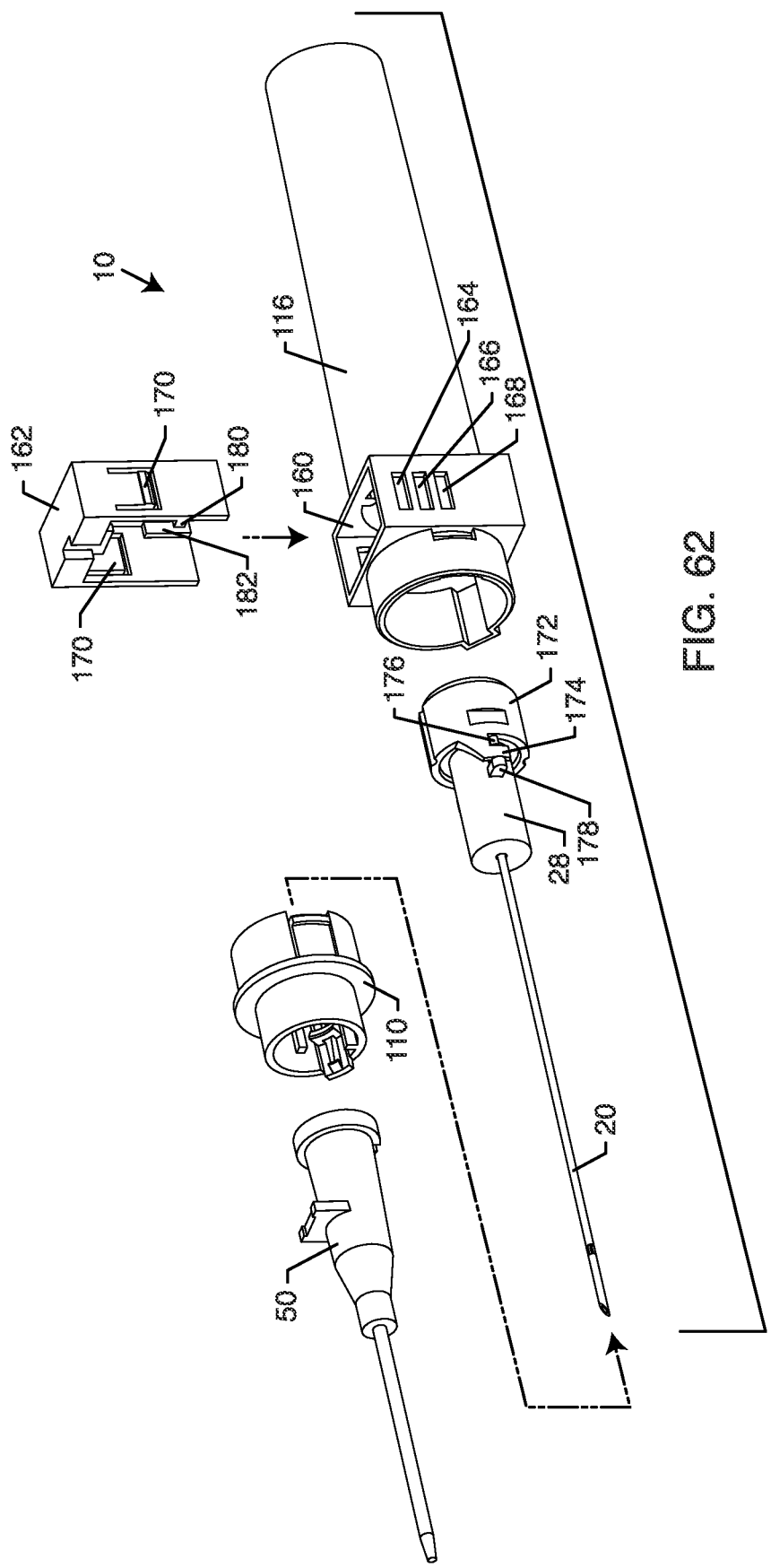
FIG. 62 is an exploded perspective view of the structure of FIG. 61.
Figure 63:
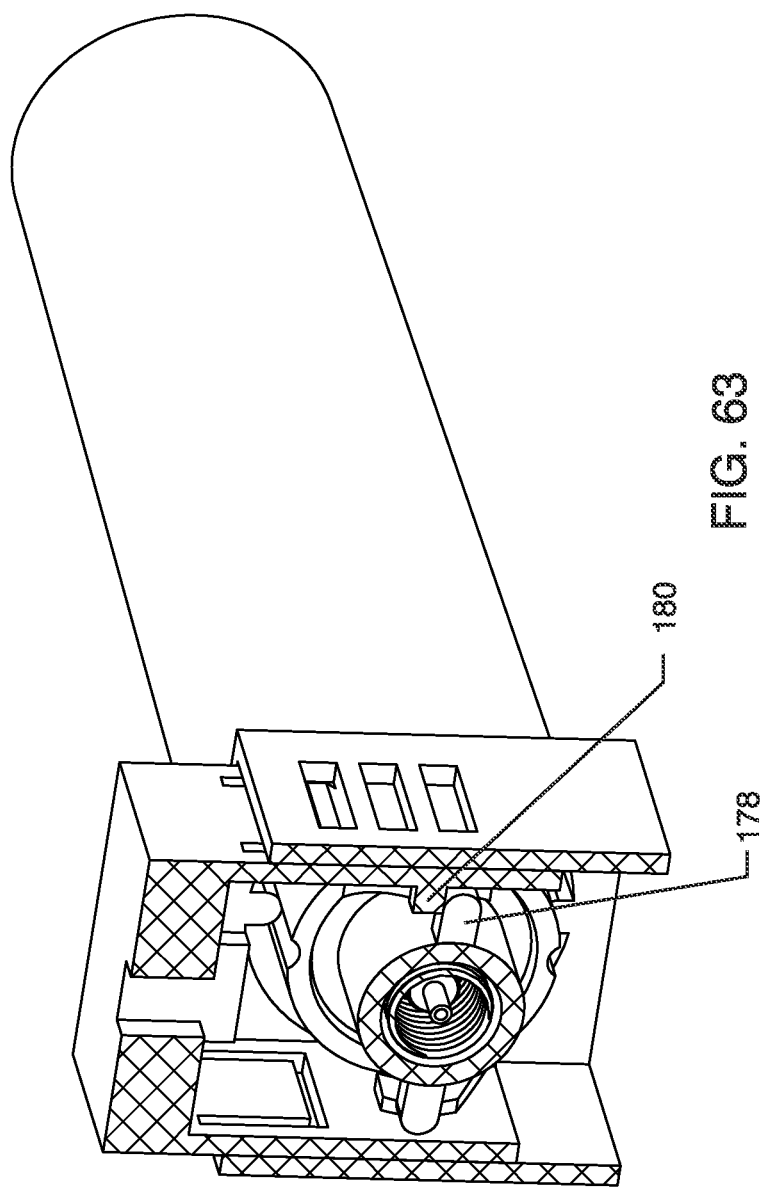
FIG. 63 is a sectional perspective view of the structure of FIG. 62 taken along lines 63-63.

FIGS. 61-63 Illustrate yet another embodiment of the present invention that is different in some ways from the embodiments previously shown and discussed herein. In this embodiment, the rear housing 112 is formed as part of the main housing 166, such that just the main housing 116 is now shown. However, it will be understood by those skilled in the art that the rear housing portion could be separately manufactured and then attached to the main housing.

The main housing has a slot 160 for a button 162 to translate within. On one or each side of the slot 160 there are three recess features 164, 166, 168. The button 160 has a flexural snap feature 170 formed on either one or both sides of the button. As previously described, the flexural snap feature is designed to engage into each of the three recess features 164, 166 and 168. In the stored position the flexural snap feature 170 is located in the top recess feature 164.

A plunger catch 172 can lock into and fixedly attach to the main housing 116. The plunger catch does not rotate within the main housing but rather is fixed relative to the main housing. The plunger catch has an extension 174 (i.e. retaining slot) that is configured to retain the plunger from moving forward or backward because the plunger has a first extension 176 and can also have a second extension 178. It can be seen in FIG. 62 that the extension 174 on the plunger catch retains the plunger extensions 176 and 178 from moving forwards or backwards.

When the button is pushed by the user from the first recess feature 164 to the second recess feature 166, a portion 180 of the button contacts the plunger and rotates the plunger such that the extensions 174 and 176/178 no longer abut. This then allows the compression spring to advance the plunger and catheter forward as previously described due the loss of vacuum inside the expandable chamber. This is best seen in FIG. 63 where one can see how the portion 180 of the button rotates the plunger when the button is depressed.

Then, when the button is pushed even further by the user from the second recess feature 166 to the third recess feature 168, the needle base can now move backwards into the rear of the main housing. This is facilitated because the button was keeping the needle base from moving backwards by an extension 182 that then moves out of the path of the needle base when the button is in the third recess feature 168.

Further improvements of the present invention are now shown in FIGS. 64A and 64B. FIG. 64A and FIG. 64B are of the same structure, where in FIG. 64A the plunger is in the stored position and in FIG. 64A the plunger 28 has moved forward a distance to the armed position.

The inventors have discovered that when the seal 44 (and possibly seal 40) is kept in a compressed state for a long period of time such as during storage, that the seal (such as an O-ring) may either start to deform (morph or take a permanent deformation) into the sidewalls it is compressed against and/or start to stick to the various sidewalls over time. Then, when the device needs to be used, it can require more force than usual to break out of this stuck or sticky state.

To alleviate and/or reduce this state of being stuck (i.e. stiction), the inventors have created an O-ring compression relief (anti-compression-set pocket) 190. When looking at FIGS. 64A and 65B, one can see that the generally hollow housing 12 includes an annularly-shaped seal relief 190 disposed on an inside surface 192 of the generally hollow housing. In FIG. 64A, the second circumferential seal 44 in the stored position is aligned along the longitudinal axis 92 with the annularly-shaped seal relief 190 such that the second circumferential seal is not in contact with the generally hollow housing. Therefore, even if the seal 44 is stored for a long period of time, this seal 44 does not tend to be deformed and/or stick to the generally hollow housing 12.

One can also see that the inside cylindrical surface of the generally hollow housing goes from a first inside surface 192 to an angled (or possibly smooth) transition surface 194 to then a (smaller diameter) second inside surface 196. The point of the transition surface 194 is to help make the transition from surface 192 to surface 196 free from problems such that the seal will not hang or catch on the transition. As shown here, the transition surface 194 is angled, but could be smoothed further with filets or the like such that it is a free flowing curvature to prevent any catching from the seal 44 as it moves past and engages the transition surface 194.

Not shown herein, but also understood by those skilled in the art from reading this teaching, is that this teaching could also be applied to the seal 40 to also prevent any stiction of the first circumferential seal 40 to the plunger 28. A second annularly shaped relief could be devised on the inside wall of the plunger, however this may then require a two part plunger to create such an undercut feature as currently presented. Alternatively, for a single part construction, one skilled in the art could machine this second annularly-shaped seal relief with a specially shaped drill and cutting bit that was designed to be placed inside the plunger to machine said seal relief. As can be seen, there are multiple ways for those skilled in the art to create this second annularly-shaped seal relief.

Although several embodiments have been described in detail for purposes of illustration, various modifications may be made to each without departing from the scope and spirit of the invention. Accordingly, the invention is not to be limited, except as by the appended claims.

What is claimed is:

1. A catheter insertion device, comprising:
   a hollow needle having a distal skin-piercing end opposite a proximal needle end, the hollow needle defining a channel in fluidic and/or pneumatic communication between the distal skin-piercing end and the proximal needle end;
   a needle base, wherein the proximal needle end is attached to the needle base;
   a plunger slidably disposed over at least a portion of the hollow needle, wherein the distal skin-piercing end of the hollow needle extends through a plunger distal end, the plunger having a plunger proximal end opposite the plunger distal end;
   a compression spring disposed concentric with and over at least a second portion of the hollow needle, the compression spring mechanically engaged directly and/or indirectly between at least a portion of the needle base and a portion of the plunger, the compression spring biasing the plunger away from the needle base;
   a catheter slidably disposed over at least a third portion of the hollow needle, wherein the distal skin-piercing end of the hollow needle extends through a distal insertion end of the catheter, the catheter comprising the distal insertion end opposite a proximal connection end, wherein a catheter surface is configured to be contactable by the plunger distal end when the plunger moves in a forward direction;

an expandable chamber in fluidic and/or pneumatic communication with the channel of the hollow needle by an aperture in the needle base, the expandable chamber at least partially delimited by the needle base and the plunger proximal end, wherein the expandable chamber is configured to increase in volume as the plunger moves towards the distal skin-piercing end of the hollow needle;

wherein a longitudinal axis is defined as extending along the hollow needle, the needle base, the plunger, the compression spring and the catheter, wherein the plunger is configured to move between a stored position, an armed position and an extended position, wherein the plunger at least rotates about the longitudinal axis between the stored position and armed position, and wherein the plunger at least translates along the longitudinal axis between the armed position and the extended position;

a generally hollow housing, wherein the needle base, the plunger and the compression spring are at least partially disposed within the generally hollow housing in the stored position;

a first circumferential seal of the expandable chamber disposed between the needle base and the plunger, the first circumferential seal configured to seal the needle base to the plunger for a distance when the plunger moves away from the needle base;

a second circumferential seal of the expandable chamber disposed between the plunger and the generally hollow housing, wherein the second circumferential seal is configured to seal the generally hollow housing to the plunger for the distance when the plunger moves away from the needle base; and wherein the generally hollow housing includes an annularly-shaped seal relief formed as an inside surface of the generally hollow housing, wherein the second circumferential seal in the stored position is aligned along the longitudinal axis with the annularly-shaped seal relief where the second circumferential seal is not in contact with the inside surface of the generally hollow housing.

2. The catheter insertion device of claim 1, wherein the inside surface is adjacent to a transition surface which is adjacent to a second inside surface, wherein the inside surface has a larger diameter in comparison to the second inside surface.

3. The catheter insertion device of claim 2, wherein the catheter is temporarily captured at the proximal connection end by the generally hollow housing with an interference fit.

4. The catheter insertion device of claim 3, including a button non-movably attached to the plunger and extending outwardly beyond the generally hollow housing, wherein the button is configured to be manipulated by the user.

5. The catheter insertion device of claim 4, wherein the generally hollow housing includes an L-shaped slot, wherein the button of the plunger extends through and is movable within the L-shaped slot between the stored position, the armed position and the extended position, wherein in the stored position the button is located at a distal lower end of the L-shaped slot, wherein in the armed position the button is located at a corner of the L-shaped slot, and wherein in the extended position the button is located at a distal upper end of the L-shaped slot.

6. The catheter insertion device of claim 5, wherein the button moves within the L- shaped slot between the distal lower end and the corner as the button rotates about the longitudinal axis moving between the stored position and the armed position, and wherein the button moves within the L-shaped slot between the corner and the distal upper end as the button translates along the longitudinal axis moving between the armed position and the extended position.

7. The catheter insertion device of claim 6, wherein the plunger translates along the longitudinal axis when a vacuum formed in the expandable chamber by the compression spring pushing the plunger away from the needle base is released by a fluid and/or a gas entering the channel of the hollow needle at the distal skin-piercing end.

8. The catheter insertion device of claim 7, wherein in the stored position a gap exists between the proximal connection end of the catheter and the plunger distal end.

9. The catheter insertion device of claim 8, wherein the plunger includes an outwardly extending tab configured to be captured by a flexural lock feature formed in the generally hollow housing when the plunger is in the extended position preventing the plunger moving backwards into the armed position.

10. The catheter insertion device of claim 9, wherein in the extended position a portion of the plunger contacts a portion of the generally hollow housing preventing the plunger from moving furthermore forwards beyond a front portion of the generally hollow housing.

11. The catheter insertion device of claim 10, wherein the expandable chamber comprises a substantially zero volume when the plunger is in the stored position.

12. The catheter insertion device of claim 10, wherein the expandable chamber comprises a substantially zero volume when the plunger is in the armed position.

* * * * *